(12) United States Patent
Martin et al.

(10) Patent No.: US 10,450,275 B2
(45) Date of Patent: Oct. 22, 2019

(54) COMPOUNDS AND METHODS FOR TREATING CANCER, NEUROLOGICAL DISORDERS, ETHANOL WITHDRAWAL, ANXIETY, DEPRESSION, AND NEUROPATHIC PAIN

(71) Applicant: Board of Regents, The University of Texas System, Austin, TX (US)

(72) Inventors: Stephen F. Martin, Austin, TX (US); James J. Sahn, Austin, TX (US); Luisa Scott, Austin, TX (US); Jonathan Thomas Pierce-Shimomura, Round Rock, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 0 days.

(21) Appl. No.: 14/978,204

(22) Filed: Dec. 22, 2015

(65) Prior Publication Data

US 2016/0280657 A1 Sep. 29, 2016

Related U.S. Application Data

(63) Continuation of application No. PCT/US2014/046730, filed on Jul. 15, 2014.
(Continued)

(51) Int. Cl.
*C07D 401/00* (2006.01)
*C07D 221/22* (2006.01)
(Continued)

(52) U.S. Cl.
CPC ......... *C07D 221/24* (2013.01); *C07D 223/16* (2013.01); *C07D 401/06* (2013.01); *C07D 403/04* (2013.01); *C07D 403/06* (2013.01); *C07D 405/04* (2013.01); *C07D 405/06* (2013.01); *C07D 405/12* (2013.01); *C07D 405/14* (2013.01); *A61K 31/496* (2013.01)

(58) Field of Classification Search
CPC .. C07D 221/22; C07D 221/26; C07D 401/04; C07D 403/04
USPC .............................................. 546/97; 544/361
See application file for complete search history.

(56) References Cited

U.S. PATENT DOCUMENTS

| | | |
|---|---|---|
| 3,887,686 A | 6/1975 | Merz et al. |
| 4,861,760 A | 8/1989 | Mazuel et al. |
| | (Continued) | |

FOREIGN PATENT DOCUMENTS

| | | |
|---|---|---|
| EP | 0 415 634 A2 | 3/1991 |
| EP | 0 415 634 A3 | 3/1991 |
| | (Continued) | |

OTHER PUBLICATIONS

Burkhard et al. "Synthesis and Structural analysis of a new class of azaspiro[3,3]hepatanes as building blocks for medicinal chemistry," Organic Letters, 2010, vol. 12, No. 9, pp. 1944-1947.*
(Continued)

*Primary Examiner* — Shengjun Wang
(74) *Attorney, Agent, or Firm* — Parker Highlander PLLC

(57) ABSTRACT

Provided herein, inter alia, are compounds and methods of treating diseases including cancer, neurological disease, alcohol withdrawal, depression and anxiety, and neuropathic pain.

14 Claims, 18 Drawing Sheets

Related U.S. Application Data

(60) Provisional application No. 61/846,234, filed on Jul. 15, 2013.

(51) Int. Cl.

| | | |
|---|---|---|
| *A61K 31/497* | (2006.01) | |
| *C07D 221/24* | (2006.01) | |
| *C07D 223/16* | (2006.01) | |
| *C07D 405/14* | (2006.01) | |
| *C07D 401/06* | (2006.01) | |
| *C07D 403/04* | (2006.01) | |
| *C07D 403/06* | (2006.01) | |
| *C07D 405/04* | (2006.01) | |
| *C07D 405/06* | (2006.01) | |
| *C07D 405/12* | (2006.01) | |
| *A61K 31/496* | (2006.01) | |

(56) References Cited

U.S. PATENT DOCUMENTS

| | | |
|---|---|---|
| 4,911,920 A | 3/1990 | Jani et al. |
| 5,212,162 A | 5/1993 | Missel et al. |
| 5,354,758 A | 10/1994 | Lawson et al. |
| 5,403,841 A | 4/1995 | Lang et al. |
| 2011/0269791 A1 | 11/2011 | Peters et al. |

FOREIGN PATENT DOCUMENTS

| | | |
|---|---|---|
| WO | WO-96/05309 A2 | 2/1996 |
| WO | WO-96/05309 A3 | 2/1996 |
| WO | WO-2009/063061 A2 | 5/2009 |
| WO | WO-2009/063061 A3 | 5/2009 |
| WO | WO-2013/029057 A2 | 2/2013 |
| WO | WO-2013/029057 A3 | 2/2013 |
| WO | WO-2013/029057 A4 | 2/2013 |

OTHER PUBLICATIONS

PubChem CID 44825925, 2010 (Year: 2010).*

Coe, J.W. et al. (Mar. 2011). "Syntheses of the opioid substructures 1,2,3,4,5,6-hexahydro-2,6-methano-3-benzazocine and 2,3,4,5-tetrahydro-1,5-methano-1H-2-benzazepine," *Tetrahedron Letters* 52(9):953-954.

International Search Report dated Jan. 2, 2015, for PCT Application No. PCT/US2014/046730, filed on Jul. 15, 2014, 5 pages.

Mazzocchi, P.H. et al. (Apr. 1981). "Synthesis and pharmacological properties of 1,2,3,4,5,6-hexahydro-1,6-methano-2-benzazocines," *J Med Chem* 24(4):457-462.

Mokotoff, M. et al. (Aug. 1970). "Azabicyclo chemistry II. Synthesis of 1,5-methano-2,3,4,5-tetrahydro-1H-2-benzazepines. B-norbenzomorphans," *Journal of Heterocyclic Chemistry* 7(4):773-778.

PubChem Compound CID 70613730, created Dec. 1, 2012, located at <https://pubchem.ncbi.nlm.nih.gov/summary/summary.cgi?cid=70613730&from=compound>, last visited Feb. 28, 2017, 12 pages.

Sahn, J.J. et al. (May 20, 2011, e-published Apr. 22, 2011). "Facile and unified approach to skeletally diverse, privileged scaffolds," *Org Lett* 13(10):2590-2593.

Sahn, J.J. et al. (Sep. 10, 2012, e-published Aug. 20, 2012). "Expedient synthesis of norbenzomorphan library via multicomponent assembly process coupled with ring-closing reactions," *ACS Comb Sci* 14(9):496-502.

Sunderhaus, J.D. et al. (Sep. 15, 2009). "Synthesis of Diverse Heterocyclic Scaffolds via Tandem Additions to Imine Derivatives and Ring-Forming Reactions," *Tetrahedron* 65(330):6454-6469.

Written Opinion dated Jan. 2, 2015, for PCT Application No. PCT/US2014/046730, filed on Jul. 15, 2014, 5 pages.

Sahn et al., "Norbenzomorphan Framework as a Novel Scaffold for Generating Sigma 2 Receptor/PGRMC1 Subtype-Selective Ligands," *ChemMedChem*, 11:556-561, 2016.

Sahn et al., "Norbenzomorphan Scaffold: Chemical Tool for Modulating Sigma Receptor-Subtype Selectivity," *ACS Med. Chem. Lett.*, 8:455-460, 2017.

Sahn et al., "Sigma 2 Receptor/Tmem97 Agonist Produce Long Lasting Antineuropathic Pain Effects in Mice," *ACS Chemical Neuroscience*, 8:1801-1811, 2017.

Yi et al., "Small molecule modulator of Sigma 2 Receptor is neuroprotective and reduces cognitive deficits and neuroinflammation in experimental models of Alzheimer's disease," *J. of Neurochemistry*, 140:561-575, 2017.

* cited by examiner

FIG. 2A
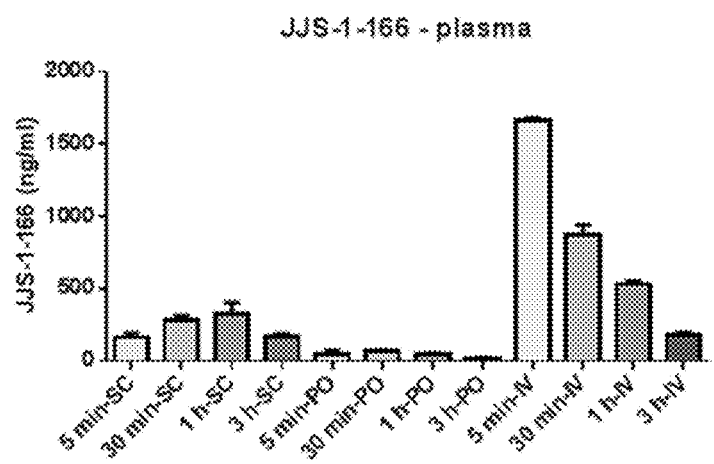
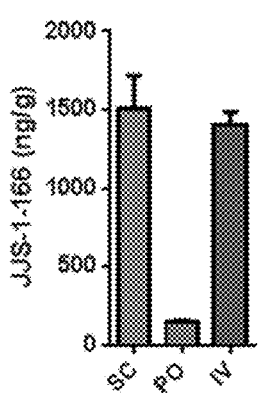
FIG. 2B
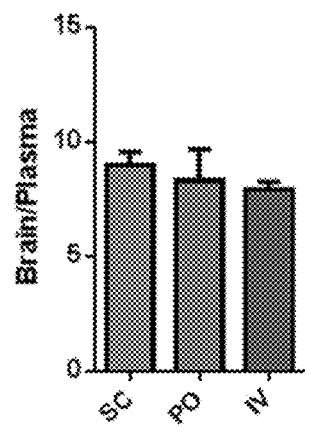
FIG. 2C

| Drug | Route | Area under curve (mean) | Average of area for IV | (%) Bioavailability |
|---|---|---|---|---|
| JJS-1-166 | SC | 44618 | | 45 |
| JJS-1-166 | PO | 7046 | | 7 |
| JJS-1-166 | IV | 99529 | 99529 | 100 |
| JJS-3-264 | SC | 13295 | | 55 |
| JJS-3-264 | PO | 3698 | | 15 |
| JJS-3-264 | IV | 24068 | 24068 | 100 |

FIG. 6

| entry | scaffold | coupling agent | product | yield (%) |
|---|---|---|---|---|
| 1 | 18{1} | 19{1} | 20{1,1} | 75 |
| 2 | 18{1} | 19{2} | 20{1,2} | 88 |
| 3 | 18{1} | 19{5} | 20{1,5} | 60 |
| 4 | 18{2} | 19{1} | 20{2,1} | 72 |
| 5 | 18{2} | 19{2} | 20{2,2} | 97 |
| 6 | 18{2} | 19{3} | 20{2,3} | 67 |
| 7 | 18{2} | 19{4} | 20{2,4} | 66 |
| 8 | 18{2} | 19{6} | 20{2,6} | 98 |
| 9 | 18{2} | 19{7} | 20{2,7} | 86 |
| 10 | 18{2} | 19{8} | 20{2,8} | 94 |
| 11 | 18{2} | 19{9} | 20{2,9} | 89 |
| 12 | 18{2} | 19{10} | 20{2,10} | 94 |
| 13 | 18{2} | 19{11} | 20{2,11} | 73 |
| 14 | 18{3} | 19{2} | 20{3,2} | 69 |
| 15 | 18{3} | 19{7} | 20{3,7} | 88 |
| 16 | 18{3} | 19{8} | 20{3,8} | 86 |
| 17 | 18{3} | 19{6} | 20{3,6} | 82 |

FIG. 11

| entry | free amine | functionalizing agent | product | yield (%) |
|---|---|---|---|---|
| 1 | 22{2} | 24{1} | 25{2,1} | 72 |
| 2 | 22{2} | 24{9} | 27{2,9} | 88 |
| 3 | 22{2} | 24{10} | 27{2,10} | 40 |
| 4 | 22{2} | 24{11} | 27{2,11} | 71 |
| 5 | 22{2} | 24{12} | 27{2,12} | 95 |
| 6 | 22{2} | 24{24} | 29{2,24} | 87 |
| 7 | 22{2} | 24{25} | 29{2,25} | 77 |
| 8 | 22{2} | 24{26} | 29{2,26} | 68 |
| 9 | 22{2} | 24{37} | 31{2,37} | 74 |
| 10 | 22{2} | 24{38} | 31{2,38} | 88 |
| 11 | 22{2} | 24{40} | 36{2,40} | 81 |
| 12 | 23{2,11} | 24{9} | 28{2,11,9} | 80 |
| 13 | 23{2,11} | 24{10} | 28{2,11,10} | 98 |
| 14 | 23{2,11} | 24{13} | 28{2,11,13} | 55 |
| 15 | 23{2,11} | 24{14} | 28{2,11,14} | 98 |
| 16 | 23{2,11} | 24{18} | 28{2,11,18} | 74 |
| 17 | 23{2,11} | 24{19} | 28{2,11,19} | 56 |
| 18 | 23{2,11} | 24{24} | 30{2,11,24} | 59 |
| 19 | 23{2,11} | 24{29} | 30{2,11,29} | 57 |
| 20 | 23{2,11} | 24{30} | 34{2,11,30} | 53 |
| 21 | 23{2,11} | 24{31} | 34{2,11,31} | 72 |
| 22 | 23{2,11} | 24{32} | 34{2,11,32} | 53 |
| 23 | 23{2,11} | 24{33} | 34{2,11,33} | 80 |
| 24 | 23{2,11} | 24{34} | 34{2,11,34} | 70 |
| 25 | 23{2,11} | 24{35} | 34{2,11,35} | 98 |
| 26 | 23{2,6} | 24{15} | 28{2,6,15} | 91 |
| 27 | 23{2,6} | 24{17} | 28{2,6,17} | 85 |
| 28 | 23{2,6} | 24{27} | 30{2,6,27} | 61 |
| 29 | 23{2,7} | 24{7} | 26{2,7,7} | 75 |
| 30 | 23{2,7} | 24{8} | 26{2,7,8} | 87 |
| 31 | 23{2,8} | 24{2} | 26{2,8,2} | 77 |
| 32 | 23{2,8} | 24{9} | 28{2,8,9} | 53 |
| 33 | 23{2,8} | 24{10} | 28{2,8,10} | 86 |
| 34 | 23{2,8} | 24{16} | 28{2,8,16} | 51 |
| 35 | 23{2,8} | 24{28} | 30{2,8,28} | 62 |
| 36 | 23{2,8} | 24{39} | 32{2,8,39} | 55 |

FIG. 11 CONT'D

| entry | free amine | functionalizing agent | product | yield (%) |
|---|---|---|---|---|
| 1 | 22{2} | 24{1} | 25{2,1} | 72 |
| 2 | 22{2} | 24{9} | 27{2,9} | 88 |
| 3 | 22{2} | 24{10} | 27{2,10} | 40 |
| 4 | 22{2} | 24{11} | 27{2,11} | 71 |
| 5 | 22{2} | 24{12} | 27{2,12} | 95 |
| 6 | 22{2} | 24{24} | 29{2,24} | 87 |
| 7 | 22{2} | 24{25} | 29{2,25} | 77 |
| 8 | 22{2} | 24{26} | 29{2,26} | 68 |
| 9 | 22{2} | 24{37} | 31{2,37} | 74 |
| 10 | 22{2} | 24{38} | 31{2,38} | 88 |
| 11 | 22{2} | 24{40} | 36{2,40} | 81 |
| 12 | 23{2,11} | 24{9} | 28{2,11,9} | 80 |
| 13 | 23{2,11} | 24{10} | 28{2,11,10} | 98 |
| 14 | 23{2,11} | 24{13} | 28{2,11,13} | 55 |
| 15 | 23{2,11} | 24{14} | 28{2,11,14} | 98 |
| 16 | 23{2,11} | 24{18} | 28{2,11,18} | 74 |
| 17 | 23{2,11} | 24{19} | 28{2,11,19} | 56 |
| 18 | 23{2,11} | 24{24} | 30{2,11,24} | 59 |
| 19 | 23{2,11} | 24{29} | 30{2,11,29} | 57 |
| 20 | 23{2,11} | 24{30} | 34{2,11,30} | 53 |
| 21 | 23{2,11} | 24{31} | 34{2,11,31} | 72 |
| 22 | 23{2,11} | 24{32} | 34{2,11,32} | 53 |
| 23 | 23{2,11} | 24{33} | 34{2,11,33} | 80 |
| 24 | 23{2,11} | 24{34} | 34{2,11,34} | 70 |
| 25 | 23{2,11} | 24{35} | 34{2,11,35} | 98 |
| 26 | 23{2,6} | 24{15} | 28{2,6,15} | 91 |
| 27 | 23{2,6} | 24{17} | 28{2,6,17} | 85 |
| 28 | 23{2,6} | 24{27} | 30{2,6,27} | 61 |
| 29 | 23{2,7} | 24{7} | 26{2,7,7} | 75 |
| 30 | 23{2,7} | 24{8} | 26{2,7,8} | 87 |
| 31 | 23{2,8} | 24{2} | 26{2,8,2} | 77 |
| 32 | 23{2,8} | 24{9} | 28{2,8,9} | 53 |
| 33 | 23{2,8} | 24{10} | 28{2,8,10} | 86 |
| 34 | 23{2,8} | 24{16} | 28{2,8,16} | 51 |
| 35 | 23{2,8} | 24{28} | 30{2,8,28} | 62 |
| 36 | 23{2,8} | 24{39} | 32{2,8,39} | 55 |

COMPOUNDS AND METHODS FOR TREATING CANCER, NEUROLOGICAL DISORDERS, ETHANOL WITHDRAWAL, ANXIETY, DEPRESSION, AND NEUROPATHIC PAIN

CROSS-REFERENCES TO RELATED APPLICATIONS

This application is a continuation application of International Application No. PCT/US2014/046730, filed Jul. 15, 2014, which claims the benefit of U.S. Provisional Application No. 61/846,234, filed Jul. 15, 2013. The disclosure of each of the prior applications is considered part of and is incorporated by reference in the disclosure of this application.

STATEMENT AS TO RIGHTS TO INVENTIONS MADE UNDER FEDERALLY SPONSORED RESEARCH AND DEVELOPMENT

This invention was made with Government support under grant number P41GM086192 awarded by the National Institutes of Health. The Government has certain rights in the invention.

BACKGROUND OF THE INVENTION

Alzheimer's Disease is one of the most common dementia among older adults. As many as 5.3 million people in the United States are living with Alzheimer's, with that number expected to grow to 14 million by 2050. ALS is one of the most common neuromuscular diseases for which there is currently no cure.

Cancer is a leading cause of death around the world, according to the World Health Organization. Cases of cancer doubled globally between 1975 and 2000, will double again by 2020, and will nearly triple by 2030. There were an estimated 12 million new cancer diagnoses and more than seven million deaths worldwide this year.

Substance abuse is a significant health problem in the USA, as well as in other countries, and is estimated to cost society over 1 billion dollars per year. There are currently very limited pharmacotherapies to treat substance abuse.

Sigma receptors are transmembrane proteins expressed in many tissues and have been implicated in, for example, cardiovascular function, substance abuse, and cancer. Many known sigma receptor ligands lack either sigma subtype selectivity or general selectivity.

It is desirable to have new therapeutics effective at treating these diseases. Provided herein are solutions to these and other problems in the art.

BRIEF SUMMARY OF THE INVENTION

Provided herein are compositions and methods useful as pharmaceutical agents. In one aspect is a compound having the formula:

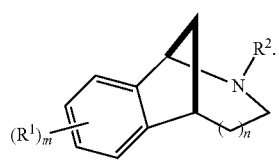

(I)

$R^1$ is hydrogen, halogen, $-N_3$, $-CF_3$, $-CCl_3$, $-CBr_3$, $-Cl_3$, $-CN$, $-C(O)R^3$, $-OR^3$, $-NR^3R^{3.4}$, $-C(O)OR^3$, $-C(O)NR^3R^{3.4}$, $-NO_2$, $-SR^3$, $-S(O)_{n1}R^3$, $-S(O)_{n1}OR^3$, $-S(O)_{n1}NR^3R^{3.4}$, $-NNR^3R^{3.4}$, $-ONR^3R^{3.4}$, $-NHC(O)NHNR^3R^{3.4}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^2$ is hydrogen, halogen, $-N_3$, $-CF_3$, $-CCl_3$, $-CBr_3$, $-Cl_3$, $-CN$, $-C(O)R^4$, $-OR^4$, $-NR^4R^{4.4}$, $-C(O)OR^4$, $-C(O)NR^4R^{4.4}$, $-NO_2$, $-SR^4$, $-S(O)_{n2}R^4$, $-S(O)_{n2}OR^4$, $-S(O)_{n2}NR^4R^{4.4}$, $-NHNR^4R^{4.4}$, $-ONR^4R^{4.4}$, $-NHC(O)NHNR^4R^{4.4}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. The symbols n1 and n2 are independently 1 or 2. The symbol m is 1, 2, 3 or 4. The symbol n is 1 or 2. $R^3$, $R^{3.4}$, $R^4$, $R^{4.4}$ are independently hydrogen, oxo, halogen, $-CF_3$, $-CN$, $-OH$, $-NH_2$, $-COOH$, $-CONH_2$, $-NO_2$, $-SH$, $-S(O)_2Cl$, $-S(O)_3H$, $-S(O)_4H$, $-S(O)_2NH_2$, $-NHNH_2$, $-ONH_2$, $-NHC(O)NHNH_2$, $-NHC(O)NH_2$, $-NHS(O)_2H$, $-NHC(O)H$, $-NHC(O)-OH$, $-NHOH$, $-OCF_3$, $-OCHF_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Provided herein are pharmaceutical compositions. In one aspect is a pharmaceutical composition that includes a compound described herein, a pharmaceutically acceptable excipient, and a pharmaceutically acceptable salt.

Also provided here are methods of treating a disease. In one aspect is a method of treating cancer in a subject in need thereof by administering an effective amount of a compound described herein. In another aspect is a method of treating neurodegenerative disease in a subject in need thereof by administering an effective amount of a compound described herein. In still another aspect is a method of treating ethanol withdrawal in a subject in need thereof by administering an effective amount of a compound described herein. In yet another aspect is a method of treating anxiety or depression in a subject in need thereof by administering an effective amount of a compound described herein. In still yet another aspect is a method of treating neuropathic pain in a subject in need thereof by administering an effective amount of a compound described herein.

Further provided herein are methods of inhibiting or antagonizing a sigma 1 or sigma 2 receptor. In one aspect is a method of inhibiting/antagonizing a sigma 2 receptor by contacting a sigma 2 receptor with a compound described herein, thereby inhibiting the sigma 2 receptor. In another aspect is a method of inhibiting a sigma 1 receptor by contacting a sigma 1 receptor with a compound described herein, thereby inhibiting said sigma 1 receptor.

Provided herein are methods of activating or agonizing a sigma 1 or sigma 2 receptor. In one aspect is a method of activating/agonizing a sigma 2 receptor by contacting a sigma 2 receptor with a compound described herein, thereby activating the sigma 2 receptor. In another aspect is a method of activating a sigma 1 receptor by contacting a sigma 1 receptor with a compound described herein, thereby activating the sigma 1 receptor.

BRIEF DESCRIPTION OF THE DRAWINGS

FIG. 2. 3 hours after subcutaneous (SC) administration of JJS-1-166, a brain concentration of 1500 ng/dL was achieved.

FIG. 6. 3 day brain clearance study. A C57Bl/6j mouse was treated with 10 mg/kg JJS-1-166. After 3 days, the level of JJS-1-166 in the brain was assessed to ensure that all or a majority of the drug had been cleared.

FIG. 11. N-functionalization of scaffolds 22 and 23.

DETAILED DESCRIPTION OF THE INVENTION

Figure 1:
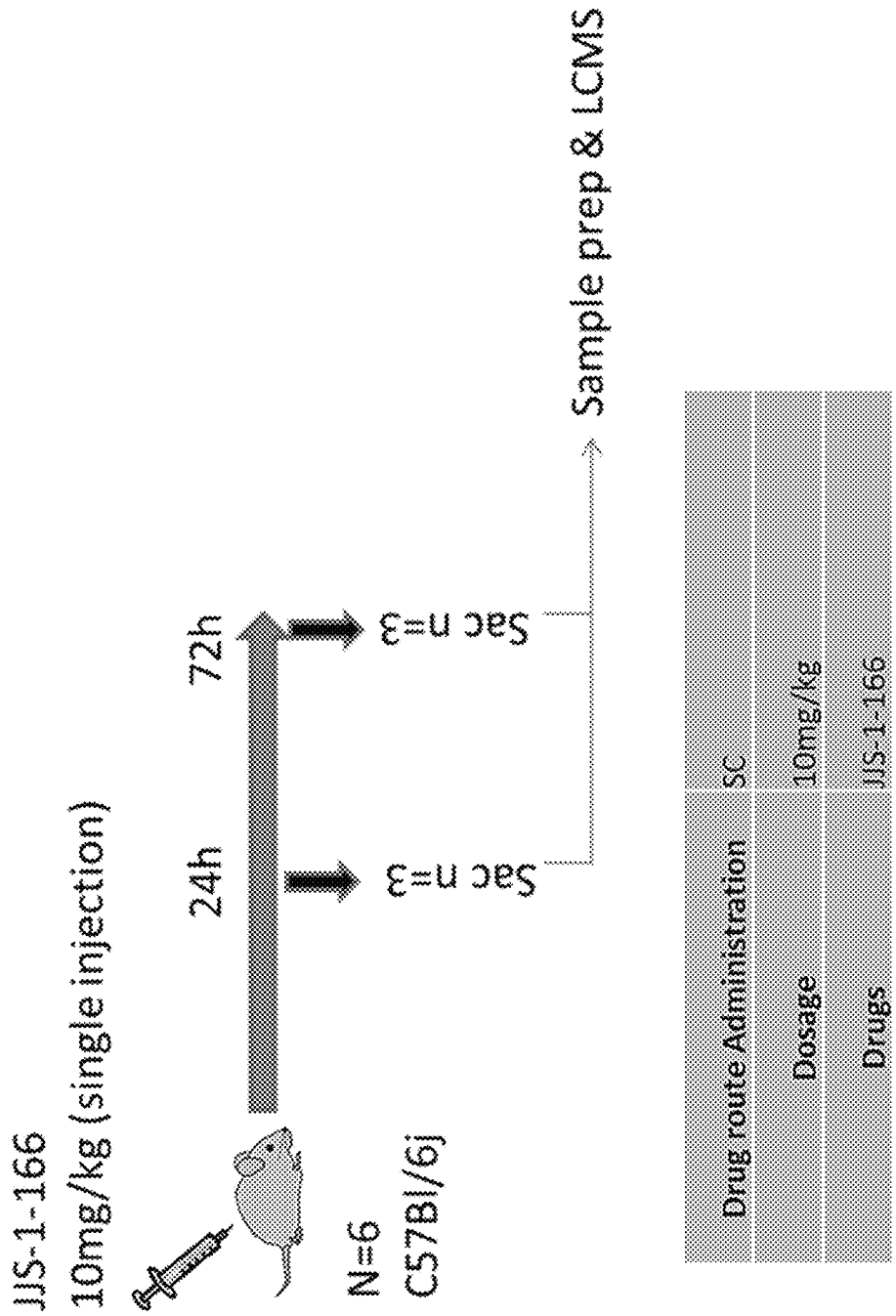
FIG. 1. Nine C57Bl/6j male mice (2-3 months old). Prior to PK evaluation, 3 animals were dosed with vehicle and were used to identify the standard curve using liquid chromatography-mass spectrometry (LC-MS) and as controls. Animals were randomized into 3 groups (n=3 per group). One group dosed Intravenously (IV), one group orally (PO), and one group subcutaneously (SC) with 10 mg/kg of the compound. From each animal blood will be collected 5 times: baseline (before the single dose); 5 minute; 30 minute; 1 hour; 3 hour after the single dose of the compound. (The first 4 collections are retro-orbital and the last one is terminal together with collection of the brain. Brain and blood will be flash frozen in liquid nitrogen and kept in −80° C. for later analysis. The concentration of compounds in the blood samples and brain tissues will be measured using LC-MS method.)
Figure 3A:
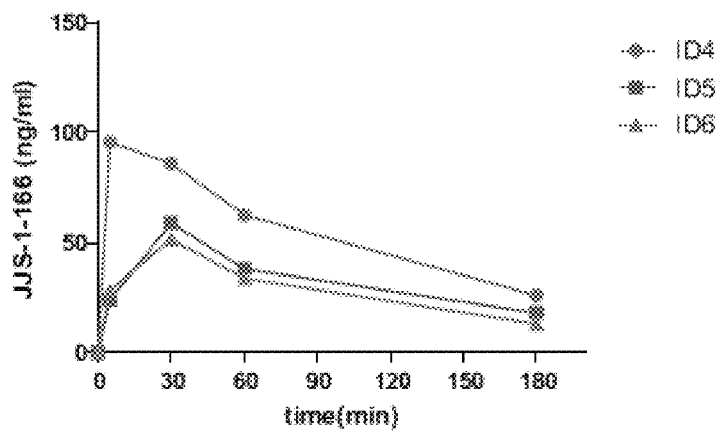
FIG. 3. 1 hour after SC administration of JJS-1-166, a plasma concentration ($C_{max}$) of greater than 300 ng/dL was achieved. 30 min after oral (PO) administration of JJS-1-166, a plasma concentration ($C_{max}$) of greater than 60 ng/dL was achieved. 5 minutes after intravenous (IV) administration of JJS-1-166, a plasma concentration ($C_{max}$) of greater than 1500 ng/dL was achieved.
Figure 3B:
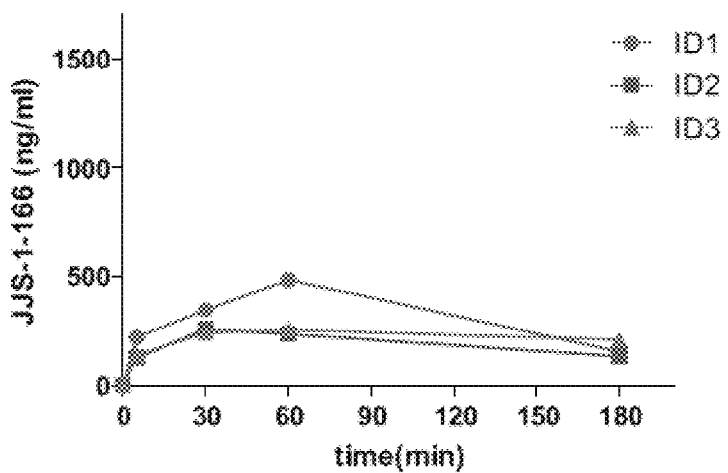
Figure 3C:
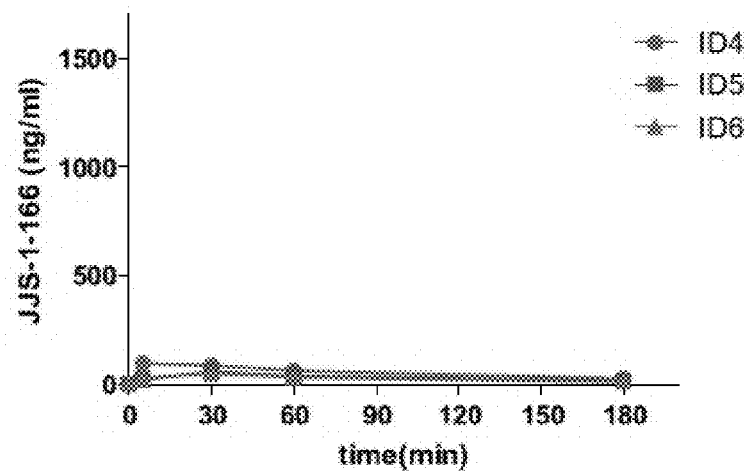
Figure 3D:
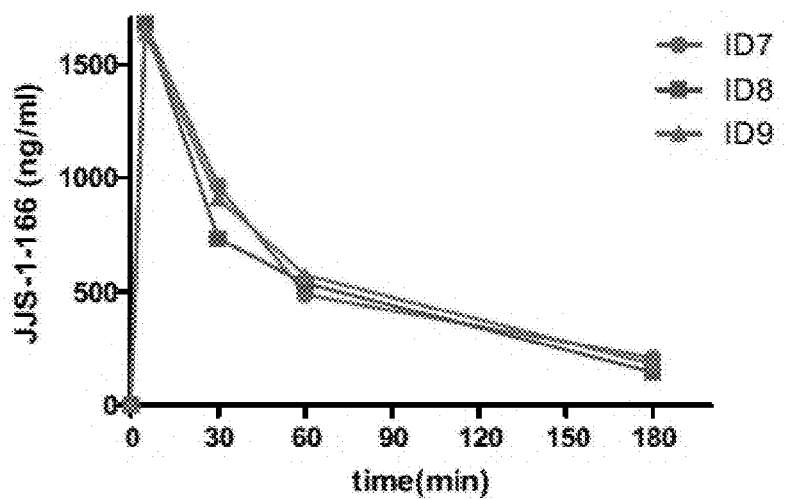
Figure 3E:
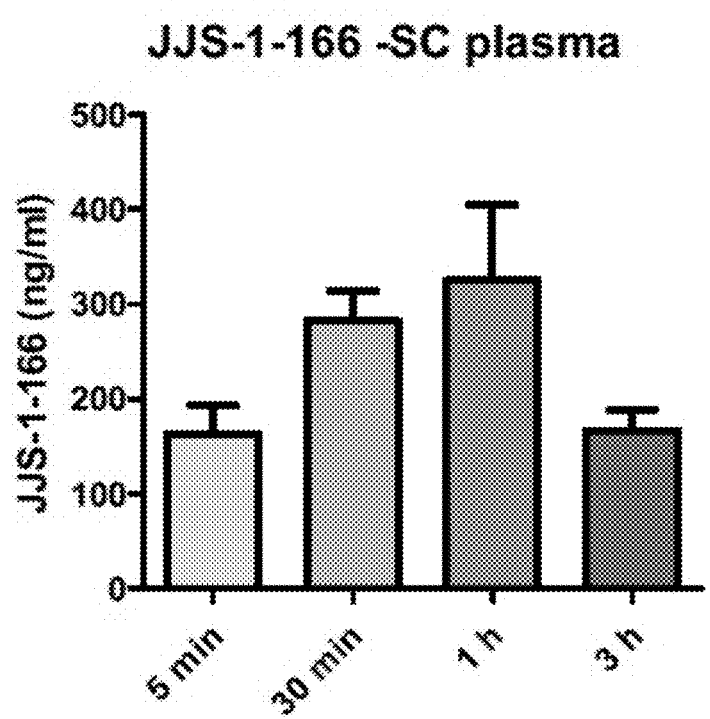
Figure 3F:
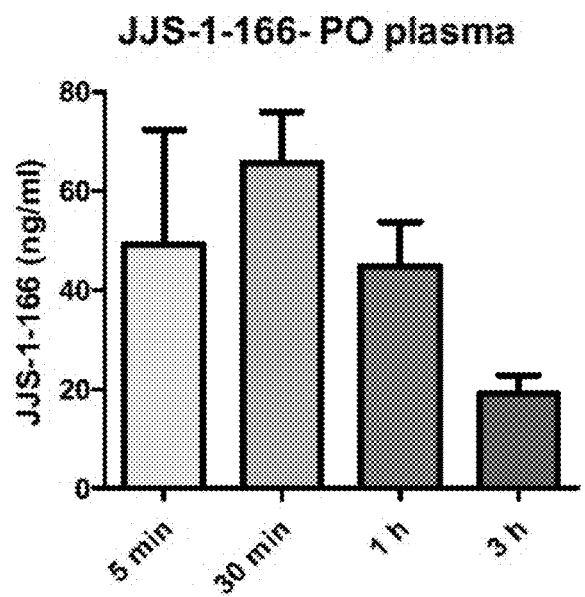
Figure 3G:
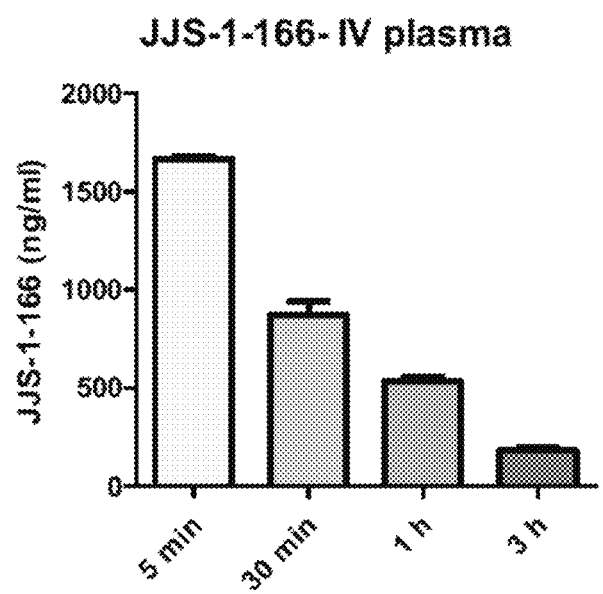
Figure 4A:
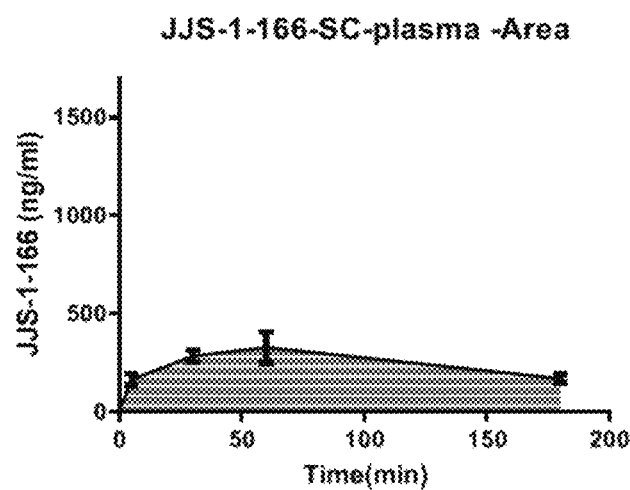
FIG. 4. Detectable plasma levels of JJS-1-166 were maintained for greater than 150 minutes after SC, OP, and IV administration.
Figure 4B:
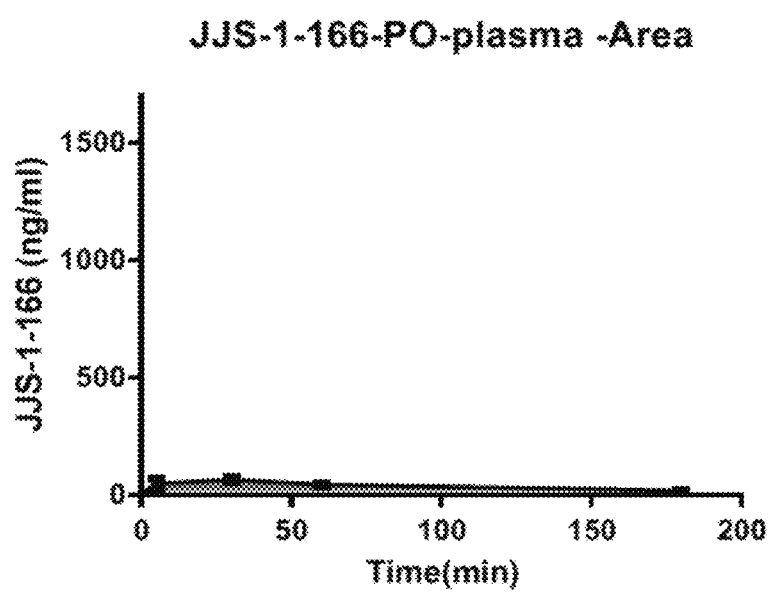
Figure 4C:
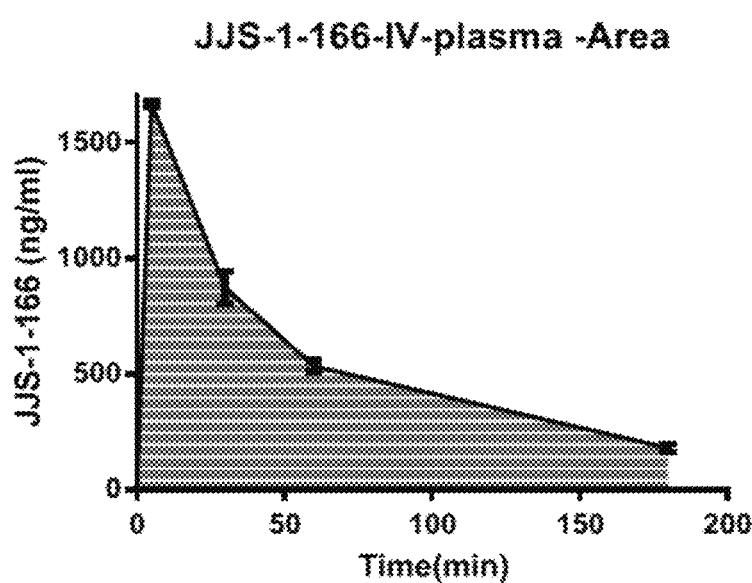
Figure 5A:
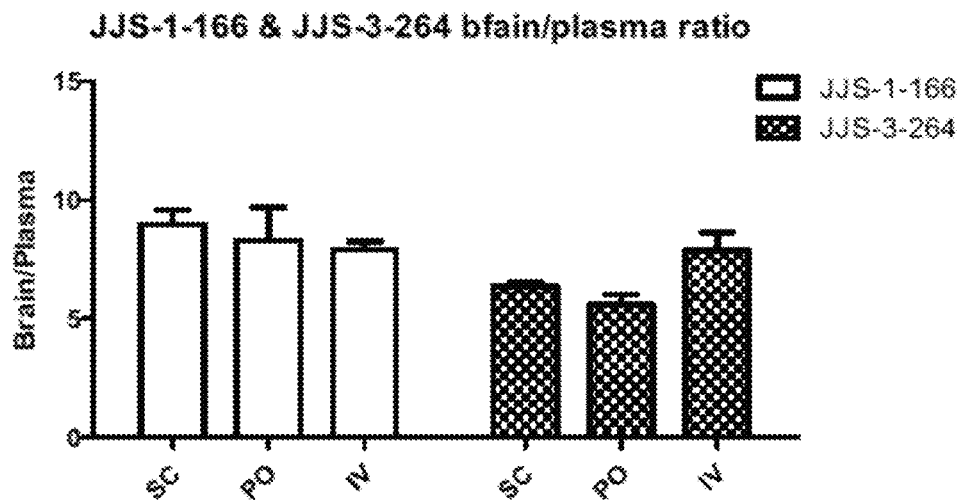
FIG. 5. A high level of brain exposure was achieved with SC administration of JJS-1-166 (3 hours). Relative to the area under the curve for IV administration, SC and OP bioavailability of JJS-1-166 are 45% and 7%, respectively.
Figure 5B:
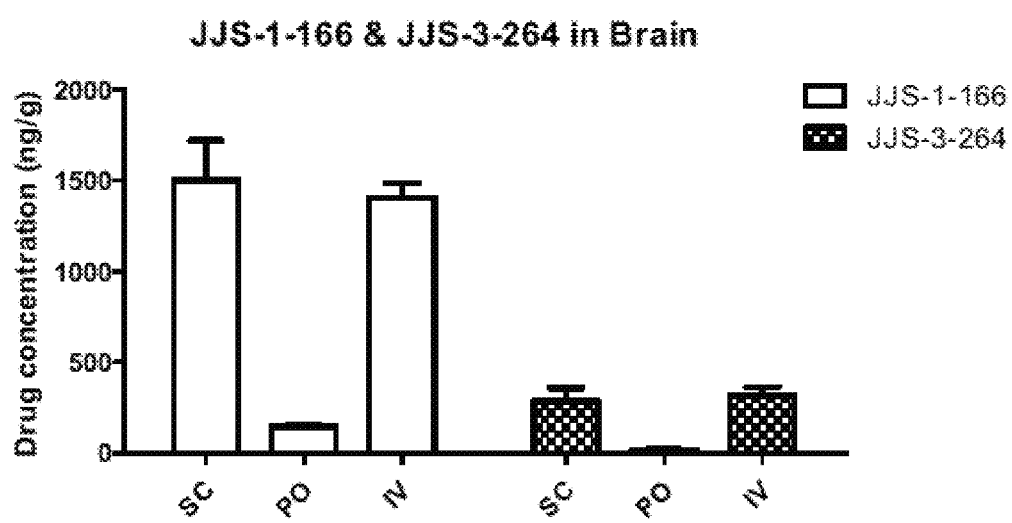
Figure 5C:
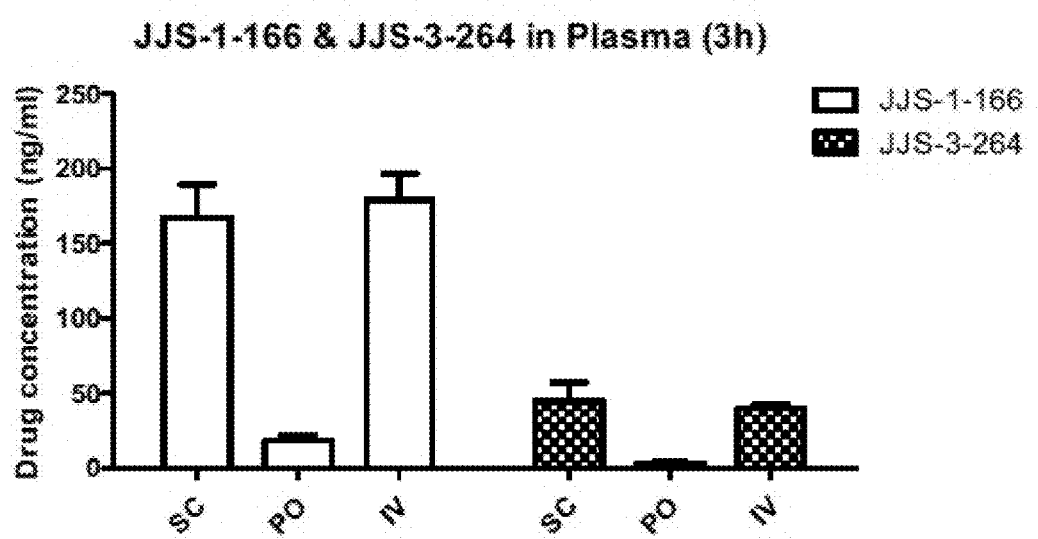
Figure 7A:
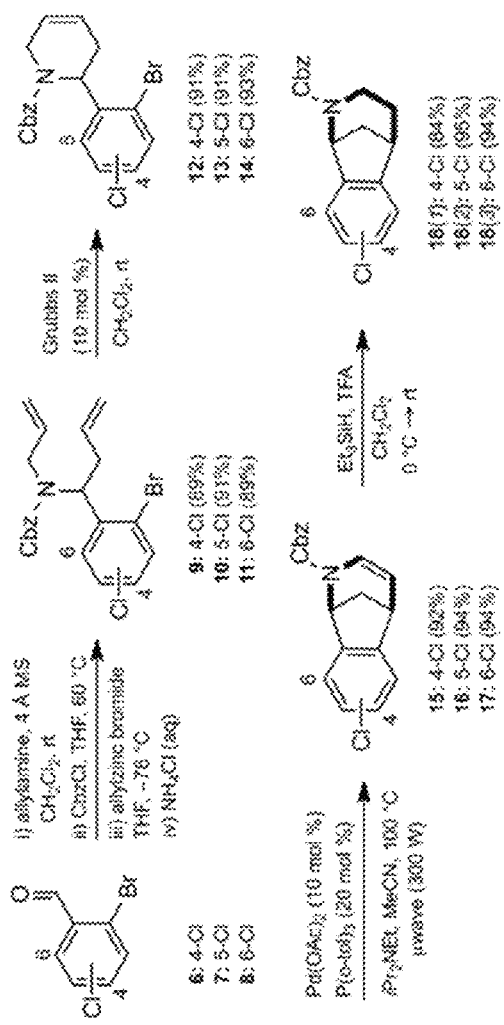
FIG. 7. Compounds 18, 20 and 21 can be prepared following the schemes shown in FIG. 1.
Figure 7B:
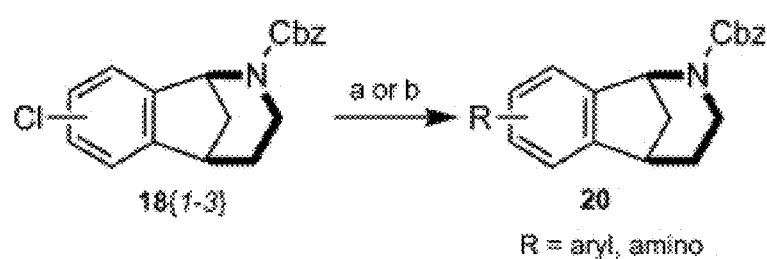
Figure 7C:
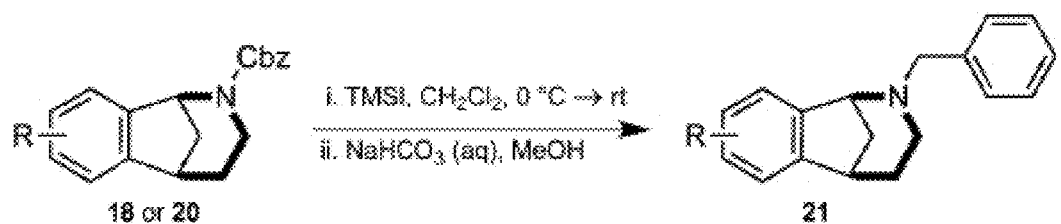
Figure 8A:
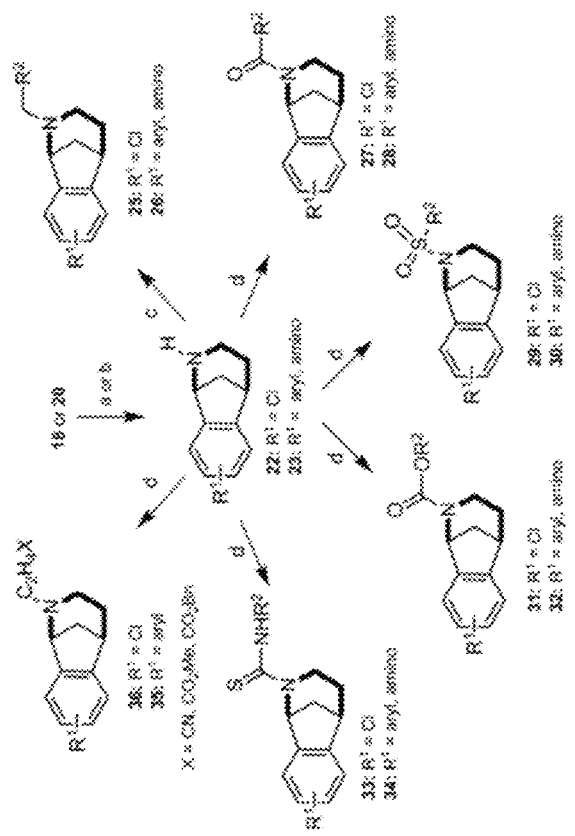
FIG. 8. Compounds 22-40 can be prepared following the schemes shown in FIG. 2.
Figure 8B:
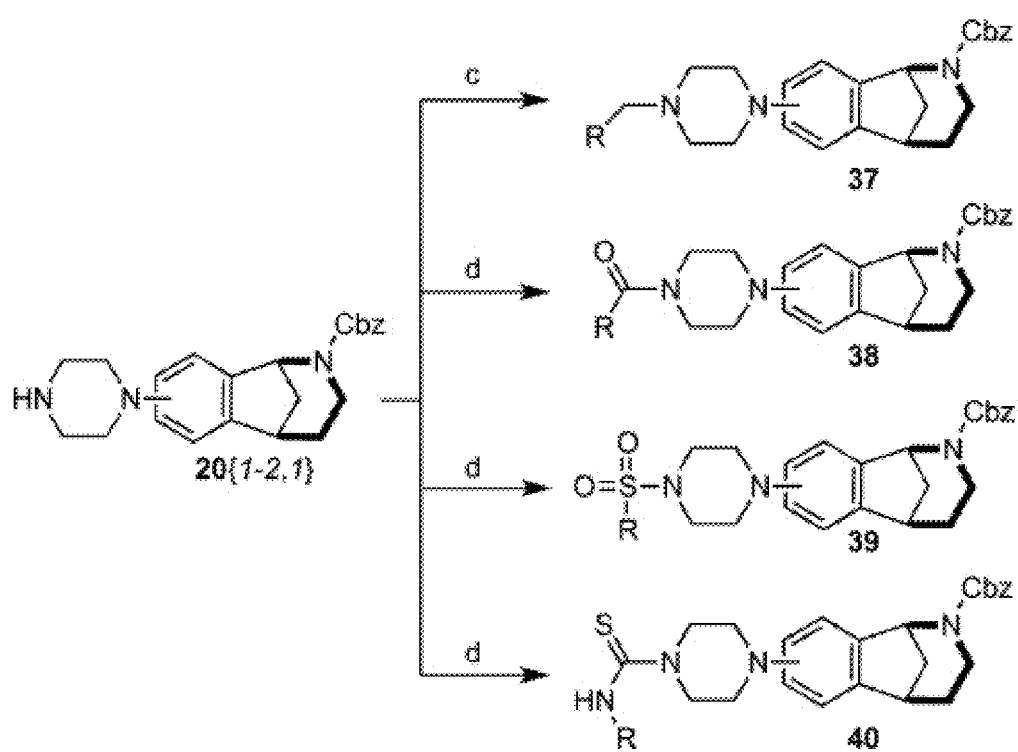
Figure 9:
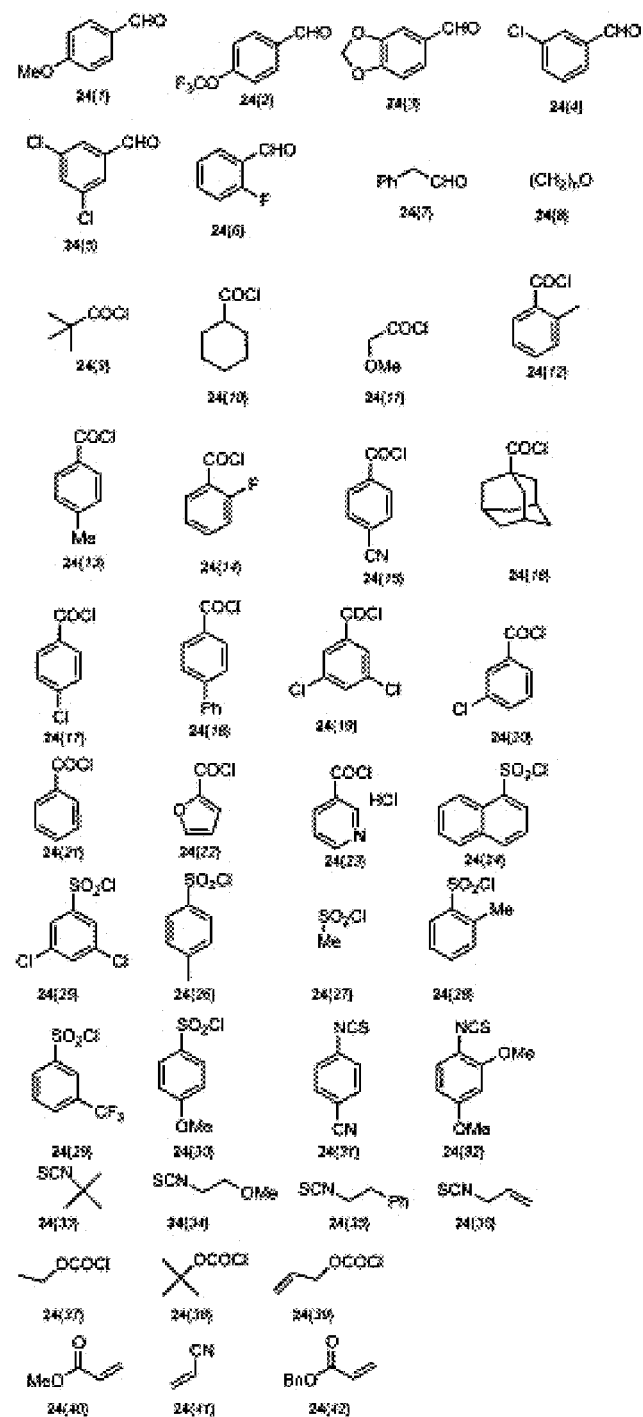
FIG. 9. Exemplary N-functionalizing agents that can be used to synthesize compounds 27-40.
Figure 10:
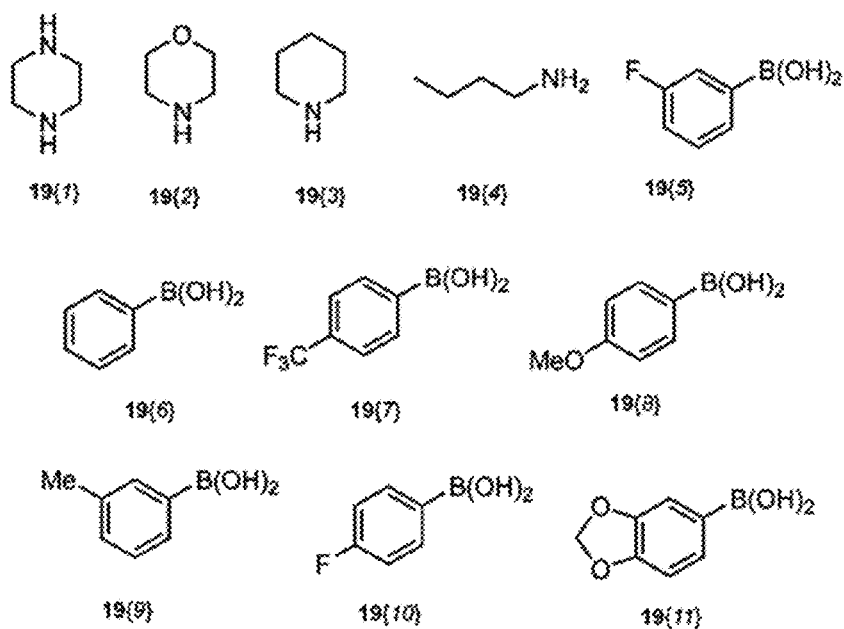
FIG. 10. Exemplary cross-coupling reactions with compound 18 and reagents.

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include mono-, di- and multivalent radicals, having the number of carbon atoms designated (i.e., $C_1$-$C_{10}$ means one to ten carbons). Alkyl is an uncyclized chain. Examples of saturated hydrocarbon radicals include, but are not limited to, groups such as methyl, ethyl, n-propyl, isopropyl, n-butyl, t-butyl, isobutyl, sec-butyl, (cyclohexyl)methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—).

The term "alkylene," by itself or as part of another substituent, means, unless otherwise stated, a divalent radical derived from an alkyl, as exemplified, but not limited by, —CH$_2$CH$_2$CH$_2$CH$_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable straight or branched chain, or combinations thereof, including at least one carbon atom and at least one heteroatom selected from the group consisting of O, N, P, Si, and S, and wherein the nitrogen and sulfur atoms may optionally be oxidized, and the nitrogen heteroatom may optionally be quaternized. The heteroatom(s) O, N, P, S, B, As, and Si may be placed at any interior position of the heteroalkyl group or at the position at which the alkyl group is attached to the remainder of the molecule. Heteroalkyl is an uncyclized chain. Examples include, but are not limited to: —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, —CH=CH—N(CH$_3$)—CH$_3$, —O—CH$_3$, —O—CH$_2$—CH$_3$, and —CN. Up to two or three heteroatoms may be consecutive, such as, for example, —CH$_2$—NH—OCH$_3$ and —CH$_2$—O—Si(CH$_3$)$_3$.

Similarly, the term "heteroalkylene," by itself or as part of another substituent, means, unless otherwise stated, a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Cycloalkyl and heterocycloalkyl are not aromatic. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$)alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, naphthyl, pyrrolyl, pyrazolyl, pyridazinyl, triazinyl, pyrimidinyl, imidazolyl, pyrazinyl, purinyl, oxazolyl, isoxazolyl, thiazolyl, furyl, thienyl, pyridyl, pyrimidyl, benzothiazolyl, benzoxazoyl benzimidazolyl, benzofuran, isobenzofuranyl, indolyl, isoindolyl, benzothiophenyl, isoquinolyl, quinoxalinyl, quinolyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. A heteroaryl group substituent may be a —O-bonded to a ring heteroatom nitrogen.

A "fused ring aryl-heterocycloalkyl" is an aryl fused to a heterocycloalkyl. A "fused ring heteroaryl-heterocycloalkyl" is a heteroaryl fused to a heterocycloalkyl. A "fused ring heterocycloalkyl-cycloalkyl" is a heterocycloalkyl fused to a cycloalkyl. A "fused ring heterocycloalkyl-heterocycloalkyl" is a heterocycloalkyl fused to another heterocycloalkyl. Fused ring aryl-heterocycloalkyl, fused ring heteroaryl-heterocycloalkyl, fused ring heterocycloalkyl-cycloalkyl, or fused ring heterocycloalkyl-heterocycloalkyl may each independently be unsubstituted or substituted with one or more of the substituents described herein. Fused ring aryl-heterocycloalkyl, fused ring heteroaryl-heterocycloalkyl, fused ring heterocycloalkyl-cycloalkyl, or fused ring heterocycloalkyl-heterocycloalkyl may each independently be named according to the size of each of the fused rings. Thus, for example, 6,5 aryl-heterocycloalkyl fused ring describes a 6 membered aryl moiety fused to a 5 membered heterocycloalkyl. Spirocyclic rings are two or more rings wherein adjacent rings are attached through a single atom. The individual rings within spirocyclic rings may be identical or different. Individual rings in spirocyclic rings may be substituted or unsubstituted and may have different substituents from other individual rings within a set of spirocyclic rings. Possible substituents for individual rings within spirocyclic rings are the possible substituents for the same ring when not part of spirocyclic rings (e.g. substituents for cycloalkyl or heterocycloalkyl rings). Spirocylic rings may be substituted or unsubstituted cycloalkyl, substituted or unsubstituted cycloalkylene, substituted or unsubstituted heterocycloalkyl or substituted or unsubstituted heterocycloalkylene and individual rings within a spirocyclic ring group may be any of the immediately previous list, including having all rings of one type (e.g. all rings being substituted heterocycloalkylene wherein each ring may be the same or different substituted heterocycloalkylene). When referring to a spirocyclic ring system, heterocyclic spirocyclic rings means a spirocyclic rings wherein at least one ring is a heterocyclic ring and wherein each ring may be a different ring. When referring to a spirocyclic ring system, substituted spirocyclic rings means that at least one ring is substituted and each substituent may optionally be different.

The term "oxo," as used herein, means an oxygen that is double bonded to a carbon atom.

The term "thio," as used herein, means a sulfur that is single or double bonded to carbon, or single bonded to another sulfur.

Each of the above terms (e.g., "alkyl," "heteroalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C (O)NR"R''', —NR"C(O)₂R', —NR—C(NR'R"R''')=NR'''', —NR—C(NR'R")=NR''', —S(O)R', —S(O)₂R', —S(O)₂NR'R", —NRSO₂R', —NR'NR"R''', —ONR'R", —NR'C(O)NR"NR'''R'''', —CN, —NO₂, —NR'SO₂R", —NR'C(O)R", —NR'C(O)—OR", —NR'OR", in a number ranging from zero to (2m'+1), where m' is the total number of carbon atoms in such radical. R, R', R", R''', and R'''' each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound of the invention includes more than one R group, for example, each of the R groups is independently selected as are each R', R", R''', and R'''' group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF₃ and —CH₂CF₃) and acyl (e.g., —C(O)CH₃, —C(O)CF₃, —C(O)CH₂OCH₃, and the like).

Similar to the substituents described for the alkyl radical, substituents for the aryl and heteroaryl groups are varied and are selected from, for example: —OR', —NR'R", —SR', -halogen, —SiR'R"R''', —OC(O)R', —C(O)R', —CO₂R', —CONR'R", —OC(O)NR'R", —NR"C(O)R', —NR'—C(O)NR"R''', —NR"C(O)₂R', —NR—C(NR'R"R''')=NR'''', —NR—C(NR'R")=NR''', —S(O)R', —S(O)₂R', —S(O)₂NR'R", —NRSO₂R', —NR'NR"R''', —ONR'R", —NR'C(O)NR"NR'''R'''', —CN, —NO₂, —R', —N₃, —CH(Ph)₂, fluoro(C₁-C₄)alkoxy, and fluoro(C₁-C₄)alkyl, —NR'SO₂R", —NR'C(O)R", —NR'C(O)—OR", —NR'OR", in a number ranging from zero to the total number of open valences on the aromatic ring system; and where R', R", R''', and R'''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound of the invention includes more than one R group, for example, each of the R groups is independently selected as are each R', R", R''', and R'''' groups when more than one of these groups is present.

Substituents for rings (e.g. cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one more more floating substituents (including, but not limited to, points of attachment to the remainder of the molecule), the floating substituents may be bonded to the heteroatoms. Where the ring heteroatoms are shown bound to one or more hydrogens (e.g. a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH₂)$_r$—B—, wherein A and B are independently —CRR'—, —O—, —NR—, —S—, —S(O)—, —S(O)₂—, —S(O)₂NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'— (C"R"R''')$_d$—, where s and d are independently integers of from 0 to 3, and X' is —O—, —NR'—, —S—, —S(O)—, —S(O)₂—, or —S(O)₂NR'—. The substituents R, R', R", and R''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include, oxygen (O), nitrogen (N), sulfur (S), phosphorus (P), Boron (B), Arsenic (As), and silicon (Si).

A "substituent group," as used herein, means a group selected from the following moieties:

(A) oxo, halogen, —CF₃, —CN, —OH, —NH₂, —COOH, —CONH₂, —NO₂, —SH, —SO₂Cl, —SO₃H, —SO₄H, —SO₂NH₂, —NHNH₂, —ONH₂, —NHC(O)NHNH₂, —NHC(O) NH₂, —NHSO₂H, —NHC(O)H, —NHC(O)—OH, —NHOH, —OCF₃, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, and heteroaryl, substituted with at least one substituent selected from:

(i) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, —NHC(O) NH$_2$, —NHSO$_2$H, —NHC(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, and heteroaryl, substituted with at least one substituent selected from:

(a) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, —NHC(O) NH$_2$, —NHSO$_2$H, —NHC(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, or heteroaryl, substituted with at least one substituent selected from: oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O) NHNH$_2$, —NHC(O) NH$_2$, —NHSO$_2$H, —NHC(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, and unsubstituted heteroaryl.

A "size-limited substituent" or "size-limited substituent group," as used herein, means a group selected from all of the substituents described above for a "substituent group," wherein each substituted or unsubstituted alkyl is a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_3$-C$_8$ cycloalkyl, and each substituted or unsubstituted heterocycloalkyl is a substituted or unsubstituted 3 to 8 membered heterocycloalkyl.

A "lower substituent" or "lower substituent group," as used herein, means a group selected from all of the substituents described above for a "substituent group," wherein each substituted or unsubstituted alkyl is a substituted or unsubstituted C$_1$-C$_8$ alkyl, each substituted or unsubstituted heteroalkyl is a substituted or unsubstituted 2 to 8 membered heteroalkyl, each substituted or unsubstituted cycloalkyl is a substituted or unsubstituted C$_3$-C$_7$ cycloalkyl, and each substituted or unsubstituted heterocycloalkyl is a substituted or unsubstituted 3 to 7 membered heterocycloalkyl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_3$-C$_8$ cycloalkyl, and/or each substituted or unsubstituted heterocycloalkyl is a substituted or unsubstituted 3 to 8 membered heterocycloalkyl. In some embodiments of the compounds herein, each substituted or unsubstituted alkylene is a substituted or unsubstituted C$_1$-C$_{20}$ alkylene, each substituted or unsubstituted heteroalkylene is a substituted or unsubstituted 2 to 20 membered heteroalkylene, each substituted or unsubstituted cycloalkylene is a substituted or unsubstituted C$_3$-C$_8$ cycloalkylene, and/or each substituted or unsubstituted heterocycloalkylene is a substituted or unsubstituted 3 to 8 membered heterocycloalkylene.

In some embodiments, each substituted or unsubstituted alkyl is a substituted or unsubstituted C$_1$-C$_8$ alkyl, each substituted or unsubstituted heteroalkyl is a substituted or unsubstituted 2 to 8 membered heteroalkyl, each substituted or unsubstituted cycloalkyl is a substituted or unsubstituted C$_3$-C$_7$ cycloalkyl, and/or each substituted or unsubstituted heterocycloalkyl is a substituted or unsubstituted 3 to 7 membered heterocycloalkyl. In some embodiments, each substituted or unsubstituted alkylene is a substituted or unsubstituted C$_1$-C$_8$ alkylene, each substituted or unsubstituted heteroalkylene is a substituted or unsubstituted 2 to 8 membered heteroalkylene, each substituted or unsubstituted cycloalkylene is a substituted or unsubstituted C$_3$-C$_7$ cycloalkylene, and/or each substituted or unsubstituted heterocycloalkylene is a substituted or unsubstituted 3 to 7 membered heterocycloalkylene.

Certain compounds of the present invention possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present invention. The compounds of the present invention do not include those which are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center.

Therefore, single stereochemical isomers as well as enantiomeric and diastereomeric mixtures of the present compounds, generally recognized as stable by those skilled in the art, are within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of this invention.

The compounds of the present invention may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$), or carbon-14 ($^{14}C$). All isotopic variations of the compounds of the present invention, whether radioactive or not, are encompassed within the scope of the present invention.

The symbol "$\sim\!\sim\!\sim$" denotes the point of attachment of a chemical moiety to the remainder of a molecule or chemical formula.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls.

Moreover, where a moiety is substituted with an R substituent, the group may be referred to as "R-substituted." Where a moiety is R-substituted, the moiety is substituted with at least one R substituent and each R substituent is optionally different. Where a particular R group is present in the description of a chemical genus (such as Formula (I)), a decimal symbol may be used to distinguish each appearance of that particular R group. For example, where multiple $R^{13}$ substituents are present, each $R^{13}$ substituent may be distinguished as $R^{13.1}$, $R^{13.2}$, $R^{13.3}$, $R^{13.4}$, etc., wherein each of $R^{13.1}$, $R^{13.2}$, $R^{13.3}$, $R^{13.4}$, etc. is defined within the scope of the definition of $R^{13}$ and optionally differently.

Description of compounds of the present invention is limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The term "pharmaceutically acceptable salts" is meant to include salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science,* 1977, 66, 1-19). Certain specific compounds of the present invention contain both basic and acidic functionalities that allow the compounds to be converted into either base or acid addition salts.

Thus, the compounds of the present invention may exist as salts, such as with pharmaceutically acceptable acids. The present invention includes such salts. Examples of such salts include hydrochlorides, hydrobromides, sulfates, methanesulfonates, nitrates, maleates, acetates, citrates, fumarates, tartrates (e.g., (+)-tartrates, (−)-tartrates, or mixtures thereof including racemic mixtures), succinates, benzoates, and salts with amino acids such as glutamic acid. These salts may be prepared by methods known to those skilled in the art.

The neutral forms of the compounds are preferably regenerated by contacting the salt with a base or acid and isolating the parent compound in the conventional manner. The parent form of the compound differs from the various salt forms in certain physical properties, such as solubility in polar solvents.

In addition to salt forms, the present invention provides compounds, which are in a prodrug form. Prodrugs of the compounds described herein include those compounds that readily undergo chemical or enzymatic changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

As used herein, the term "salt" refers to acid or base salts of the compounds used in the methods of the present invention. Illustrative examples of acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts.

The terms "treating", or "treatment" refers to any indicia of success in the treatment or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. The term "treating" and conjugations thereof, include prevention of an injury, pathology, condition, or disease.

An "effective amount" is an amount sufficient to accomplish a stated purpose (e.g. achieve the effect for which it is administered, treat a disease, reduce enzyme activity, increase enzyme activity, reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound being employed. The dose administered to a patient, in the context of the present invention should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached.

Dosage amounts and intervals can be adjusted individually to provide levels of the administered compound effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is effective to treat the clinical symptoms demonstrated by the particular patient. This planning should involve the careful choice of active compound by considering factors such as compound potency, relative bioavailability, patient body weight, presence and severity of adverse side effects, preferred mode of administration and the toxicity profile of the selected agent.

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects. In embodiments, a control is the measurement of the activity of a protein in the absence of a compound as described herein (including embodiments and examples).

"Contacting" is used in accordance with its plain ordinary meaning and refers to the process of allowing at least two distinct species (e.g. chemical compounds including biomolecules or cells) to become sufficiently proximal to react, interact or physically touch. It should be appreciated; however, the resulting reaction product can be produced directly from a reaction between the added reagents or from an intermediate from one or more of the added reagents which can be produced in the reaction mixture.

The term "contacting" may include allowing two species to react, interact, or physically touch, wherein the two species may be a compound as described herein and a protein or enzyme. In some embodiments contacting includes allowing a compound described herein to interact with a protein or enzyme that is involved in a signaling pathway.

As defined herein, the term "inhibition", "inhibit", "inhibiting", and "antagonizing" the like in reference to a protein-inhibitor interaction means negatively affecting (e.g. decreasing) the activity or function of the protein relative to the activity or function of the protein in the absence of the inhibitor. In embodiments inhibition refers to reduction of a disease or symptoms of disease. In embodiments, inhibition refers to a reduction in the activity of a particular protein or nucleic acid target. Thus, inhibition includes, at least in part, partially or totally blocking stimulation, decreasing, preventing, or delaying activation, or inactivating, desensitizing, or down-regulating signal transduction or enzymatic activity or the amount of a protein.

The terms "activation", "activate", "activating", and "agonizing" and the like refer to positively affecting (e.g. increasing) the activity or function of the protein relative to the activity or function of the protein in the absence of the activator. Activation may include, at least in part, partially or totally increasing stimulation, increasing or enabling activation, or activating, sensitizing, or up-regulating signal transduction or enzymatic activity or the amount of a protein decreased in a disease. Activation may include, at least in part, partially or totally increasing stimulation, increasing or enabling activation, or activating, sensitizing, or up-regulating signal transduction or enzymatic activity or the amount of a protein that may modulate the level of another protein or increase cell survival.

The term "modulator" refers to a composition that increases or decreases the level of a target molecule or the function of a target molecule or the physical state of the target of the molecule.

The term "modulate" is used in accordance with its plain and ordinary meaning and refers to the act of changing or varying one or more properties. "Modulation" refers to the process of changing or varying one or more properties. For example, a modulator of a target protein changes by increasing or decreasing a property or function of the target molecule or the amount of the target molecule. A modulator of a disease decreases a symptom, cause, or characteristic of the targeted disease.

"Selective" or "selectivity" or the like of a compound refers to the compound's ability to discriminate between molecular targets. "Specific", "specifically", "specificity", or the like of a compound refers to the compound's ability to cause a particular action, such as inhibition, to a particular molecular target with minimal or no action to other proteins in the cell.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethylcellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

As used herein, the term "administering" means oral administration, administration as a suppository, topical contact, intravenous, parenteral, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc.

The compositions disclosed herein can be delivered by transdermally, by a topical route, formulated as applicator sticks, solutions, suspensions, emulsions, gels, creams, ointments, pastes, jellies, paints, powders, and aerosols. Oral preparations include tablets, pills, powder, dragees, capsules, liquids, lozenges, cachets, gels, syrups, slurries, suspensions, etc., suitable for ingestion by the patient. Solid form preparations include powders, tablets, pills, capsules, cachets, suppositories, and dispersible granules. Liquid form preparations include solutions, suspensions, and emulsions, for example, water or water/propylene glycol solutions. The compositions of the present invention may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes. The compositions disclosed herein can also be delivered as microspheres for slow release in the body. For example, microspheres can be administered via intradermal injection of drug-containing microspheres, which slowly release subcutaneously (see Rao, *J. Biomater Sci. Polym. Ed.* 7:623-645, 1995; as biodegradable and injectable gel formulations (see, e.g., Gao *Pharm. Res.* 12:857-863, 1995); or, as microspheres for oral administration (see, e.g., Eyles, *J. Pharm. Pharmacol.* 49:669-674, 1997). The formulations of the compositions of the present invention can be delivered by the use of liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions of the present invention into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989). The compositions can also be delivered as nanoparticles.

Pharmaceutical compositions may include compositions wherein the active ingredient (e.g. compounds described herein, including embodiments or examples) is contained in a therapeutically effective amount, i.e., in an amount effective to achieve its intended purpose. The actual amount effective for a particular application will depend, inter alia, on the condition being treated. When administered in methods to treat a disease, such compositions will contain an amount of active ingredient effective to achieve the desired result, e.g., modulating the activity of a target molecule, and/or reducing, eliminating, or slowing the progression of disease symptoms.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated, kind of concurrent treatment, complications from the disease being treated or other health-related problems. Other therapeutic regimens or agents can be used in conjunction with the methods and compounds of Applicants' invention. Adjustment and manipulation of established dosages (e.g., frequency and duration) are well within the ability of those skilled in the art.

The compounds and complexes described herein can be used in combination with one another, with other active drugs known to be useful in treating a disease (e.g. anti-cancer drugs) or with adjunctive agents that may not be effective alone, but may contribute to the efficacy of the active agent.

By "co-administer" it is meant that a composition described herein is administered at the same time, just prior to, or just after the administration of one or more additional therapies, for example an anticancer agent as described herein. The compound of the invention can be administered alone or can be co-administered to the patient. Co-administration is meant to include simultaneous or sequential administration of the compound individually or in combination (more than one compound or agent). Thus, the preparations can also be combined, when desired, with other active substances (e.g. anticancer agents).

Co-administration includes administering one active agent (e.g. a compound described herein or an anti-cancer agent) within 0.5, 1, 2, 4, 6, 8, 10, 12, 16, 20, or 24 hours of a second active agent (e.g. a compound described herein or an anti-cancer agent). Also contemplated herein, are embodiments, where co-administration includes administering one active agent (e.g. a compound herein) within 0.5, 1, 2, 4, 6, 8, 10, 12, 16, 20, or 24 hours of a second active agent (e.g. a compound described herein or an anti-cancer agent). Co-administration includes administering two active agents simultaneously, approximately simultaneously (e.g., within about 1, 5, 10, 15, 20, or 30 minutes of each other), or sequentially in any order. Co-administration can be accomplished by co-formulation, i.e., preparing a single pharmaceutical composition including both active agents. The active agents can be formulated separately. The active and/or adjunctive agents may be linked or conjugated to one another. The compounds and complexes described herein may be combined with treatments for cancer, when administered to a subject in need thereof, such as chemotherapy or radiation therapy.

The term "associated" or "associated with" in the context of a substance or substance activity or function associated with a disease means that the disease is caused by (in whole or in part), a symptom of the disease is caused by (in whole or in part) the substance or substance activity or function, or a side-effect of the compound (e.g. toxicity) is caused by (in whole or in part) the substance or substance activity or function.

"Patient," "subject," "patient in need thereof," and "subject in need thereof" are herein used interchangeably and refer to a living organism suffering from or prone to a disease or condition that can be treated by administration of a pharmaceutical composition as provided herein. Non-limiting examples include humans, other mammals, bovines, rats, mice, dogs, monkeys, goat, sheep, cows, deer, and other non-mammalian animals. A patient may be human.

"Disease" or "condition" refer to a state of being or health status of a patient or subject capable of being treated with the compounds or methods provided herein. Disease as used herein may refer to cancer, a neurodegenerative disease, alcohol withdrawal, depression, anxiety, or neuropathic pain.

As used herein, the term "neurodegenerative disease" refers to a disease or condition in which the function of a subject's nervous system becomes impaired. Examples of neurodegenerative diseases that may be treated with a compound or method described herein include Alexander's disease, Alper's disease, Alzheimer's disease, Amyotrophic lateral sclerosis, Ataxia telangiectasia, Batten disease (also known as Spielmeyer-Vogt-Sjogren-Batten disease), Bovine spongiform encephalopathy (BSE), Canavan disease, Cockayne syndrome, Corticobasal degeneration, Creutzfeldt-Jakob disease, frontotemporal dementia, Gerstmann-Straussler-Scheinker syndrome, Huntington's disease, HIV-associated dementia, Kennedy's disease, Krabbe's disease, kuru, Lewy body dementia, Machado-Joseph disease (Spinocerebellar ataxia type 3), Multiple sclerosis, Multiple System Atrophy, Narcolepsy, Neuroborreliosis, Parkinson's disease, Pelizaeus-Merzbacher Disease, Pick's disease, Primary lateral sclerosis, Prion diseases, Refsum's disease, Sandhoffs disease, Schilder's disease, Subacute combined degeneration of spinal cord secondary to Pernicious Anaemia, Schizophrenia, Spinocerebellar ataxia (multiple types with varying characteristics), Spinal muscular atrophy, Steele-Richardson-Olszewski disease, Tabes *dorsalis*, drug-induced Parkinsonism, progressive supranuclear palsy, corticobasal degeneration, multiple system atrophy, Idiopathic Parkinson's disease, Autosomal dominant Parkinson disease, Parkinson disease, familial, type 1 (PARK1), Parkinson disease 3, autosomal dominant Lewy body (PARK3), Parkinson disease 4, autosomal dominant Lewy body (PARK4), Parkinson disease 5 (PARK5), Parkinson disease 6, autosomal recessive early-onset (PARK6), Parkinson disease 2, autosomal recessive juvenile (PARK2), Parkinson disease 7, autosomal recessive early-onset (PARK7), Parkinson disease 8 (PARK8), Parkinson disease 9 (PARK9), Parkinson disease 10 (PARK10), Parkinson disease 11 (PARK11), Parkinson disease 12 (PARK12), Parkinson disease 13 (PARK13), or Mitochondrial Parkinson's disease. Neurological disease as used herein may refer to Alzheimer's disease or ALS.

As used herein, the term "cancer" refers to all types of cancer, neoplasm, or malignant or benign tumors found in mammals, including leukemia, carcinomas and sarcomas. Exemplary cancers include acute myeloid leukemia ("AML"), chronic myelogenous leukemia ("CML"), and cancer of the brain, breast, triple-negative breast cancer, pancreas, colon, liver, kidney, lung, non-small cell lung, melanoma, ovary, sarcoma, and prostate. Additional examples include, cervix cancers, stomach cancers, head & neck cancers, uterus cancers, mesothelioma, metastatic bone cancer, Medulloblastoma, Hodgkin's Disease, Non-Hodgkin's Lymphoma, multiple myeloma, neuroblastoma, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, and neoplasms of the endocrine and exocrine pancreas.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). The murine leukemia model is widely accepted as being predictive of in vivo anti-leukemic activity. It is believed that a compound that tests positive in the P388 cell assay will generally exhibit some level of anti-leukemic activity regardless of the type of leukemia being treated. Accordingly, the present invention includes a method of treating leukemia, including treating acute myeloid leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, and undifferentiated cell leukemia.

The term "sarcoma" generally refers to a tumor which is made up of a substance like the embryonic connective tissue and is generally composed of closely packed cells embedded in a fibrillar or homogeneous substance. Sarcomas which can be treated with a combination of antineoplastic thiol-binding mitochondrial oxidant and an anticancer agent include a chondrosarcoma, fibrosarcoma, lymphosarcoma, melanosarcoma, myxosarcoma, osteosarcoma, Abernethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, and telangiectaltic sarcoma.

The term "melanoma" is taken to mean a tumor arising from the melanocytic system of the skin and other organs. Melanomas which can be treated with a combination of antineoplastic thiol-binding mitochondrial oxidant and an anticancer agent include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, and superficial spreading melanoma.

The term "carcinoma" refers to a malignant new growth made up of epithelial cells tending to infiltrate the surrounding tissues and give rise to metastases. Exemplary carcinomas which can be treated with a combination of antineoplastic thiol-binding mitochondrial oxidant and an anticancer agent include, for example, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypemephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, and carcinoma villosum.

"Anti-cancer agent" is used in accordance with its plain and ordinary meaning and refers to a composition (e.g. compound, drug, antagonist, inhibitor, modulator) having antineoplastic properties or the ability to inhibit the growth or proliferation of cells. An anti-cancer agent may be a chemotherapeutic agent. An anti-cancer agent may be an agent approved by the FDA or similar regulatory agency of a country other than the USA, for treating cancer.

Examples of anti-cancer agents include, but are not limited to, MEK (e.g. MEK1, MEK2, or MEK1 and MEK2) inhibitors (e.g. XL518, CI-1040, PD035901, selumetinib/AZD6244, GSK1120212/trametinib, GDC-0973, ARRY-162, ARRY-300, AZD8330, PD0325901, U0126, PD98059, TAK-733, PD318088, AS703026, BAY 869766), alkylating agents (e.g., cyclophosphamide, ifosfamide, chlorambucil, busulfan, melphalan, mechlorethamine, uramustine, thiotepa, nitrosoureas, nitrogen mustards (e.g., mechloroethamine, cyclophosphamide, chlorambucil, meiphalan), ethylenimine and methylmelamines (e.g., hexamethlymelamine, thiotepa), alkyl sulfonates (e.g., busulfan), nitrosoureas (e.g., carmustine, lomusitne, semustine, streptozocin), triazenes (decarbazine)), anti-metabolites (e.g., 5-azathioprine, leucovorin, capecitabine, fludarabine, gemcitabine, pemetrexed, raltitrexed, folic acid analog (e.g., methotrexate), or pyrimidine analogs (e.g., fluorouracil, floxouridine, Cytarabine), purine analogs (e.g., mercaptopurine, thioguanine, pentostatin), etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds (e.g. cisplatin, oxaloplatin, carboplatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide), epipodophyllotoxins (e.g., etoposide), antibiotics (e.g., daunorubicin, doxorubicin, bleomycin), enzymes (e.g., L-asparaginase), inhibitors of mitogen-activated protein kinase signaling (e.g. U0126, PD98059, PD184352, PD0325901, ARRY-142886, SB239063, SP600125, BAY 43-9006, wortmannin, or LY294002, Syk inhibitors, mTOR inhibitors, antibodies (e.g., rituxan), gossyphol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib (Gleevec®), geldanamycin, 17-N-Allylamino-17-Demethoxygeldanamycin (17-AAG), flavopiridol, LY294002, bortezomib, trastuzumab, BAY 11-7082, PKC412, PD184352, 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; j asplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B 1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer, Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; iimofosine; interleukin I1 (including recombinant interleukin II, or rIL.sub.2), interferon alfa-2a; interferon alfa-2b; interferon alfa-n1; interferon alfa-n3; interferon beta-1a; interferon gamma-1b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazoie; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride, agents that arrest cells in the G2-M phases and/or modulate the formation or stability of microtubules, (e.g. Taxol™ (i.e. paclitaxel), Taxotere™, compounds comprising the taxane skeleton, Erbulozole (i.e. R-55104), Dolastatin 10 (i.e. DLS-10 and NSC-376128), Mivobulin isethionate (i.e. as CI-980), Vincristine, NSC-639829, Discodermolide (i.e. as NVP-XX-A-296), ABT-751 (Abbott, i.e. E-7010), Altorhyrtins (e.g. Altorhyrtin A and Altorhyrtin C), Spongistatins (e.g. Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (i.e. LU-103793 and NSC-D-669356), Epothilones (e.g. Epothilone A, Epothilone B, Epothilone C (i.e. desoxyepothilone A or dEpoA), Epothilone D (i.e. KOS-862, dEpoB, and desoxyepothilone B), Epothilone E, Epothilone F, Epothilone B N-oxide, Epothilone A N-oxide, 16-aza-epothilone B, 21-aminoepothilone B (i.e. BMS-310705), 21-hydroxyepothilone D (i.e. Desoxyepothilone F and dEpoF), 26-fluoroepothilone, Auristatin PE (i.e. NSC-654663), Soblidotin (i.e. TZT-1027), LS-4559-P (Pharmacia, i.e. LS-4577), LS-4578 (Pharmacia, i.e. LS-477-P), LS-4477 (Pharmacia), LS-4559 (Pharmacia), RPR-112378 (Aventis), Vincristine sulfate, DZ-3358 (Daiichi), FR-182877 (Fujisawa, i.e. WS-9885B), GS-164 (Takeda), GS-198 (Takeda), KAR-2 (Hungarian Academy of Sciences), BSF-223651 (BASF, i.e. ILX-651 and LU-223651), SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (i.e. LY-355703), AC-7739 (Ajinomoto, i.e. AVE-8063A and CS-39.HCl), AC-7700 (Ajinomoto, i.e. AVE-8062, AVE-8062A, CS-39-L-Ser.HCl, and RPR-258062A), Vitilevuamide, Tubulysin A, Canadensol, Centaureidin (i.e. NSC-106969), T-138067 (Tularik, i.e. T-67, TL-138067 and TI-138067), COBRA-1 (Parker Hughes Institute, i.e. DDE-261 and WHI-261), H10 (Kansas State University), H16 (Kansas State University), Oncocidin A1 (i.e. BTO-956 and DIME), DDE-313 (Parker Hughes Institute), Fijianolide B, Laulimalide, SPA-2 (Parker Hughes Institute), SPA-1 (Parker Hughes Institute, i.e. SPIKET-P), 3-IAABU (Cytoskeleton/Mt. Sinai School of Medicine, i.e. MF-569), Narcosine (also known as NSC-5366), Nascapine, D-24851 (Asta Medica), A-105972 (Abbott), Hemiasterlin, 3-BAABU (Cytoskeleton/Mt. Sinai School of Medicine, i.e. MF-191), TMPN (Arizona State University), Vanadocene acetylacetonate, T-138026 (Tularik), Monsatrol, lnanocine (i.e. NSC-698666), 3-IAABE (Cytoskeleton/Mt. Sinai School of Medicine), A-204197 (Abbott), T-607 (Tuiarik, i.e. T-900607), RPR-115781 (Aventis), Eleutherobins (such as Desmethyleleutherobin, Desaetyleleutherobin, Iso-eleutherobin A, and Z-Eleutherobin), Caribaeoside, Caribaeolin, Halichondrin B, D-64131 (Asta Medica), D-68144

(Asta Medica), Diazonamide A, A-293620 (Abbott), NPI-2350 (Nereus), Taccalonolide A, TUB-245 (Aventis), A-259754 (Abbott), Diozostatin, (−)-Phenylahistin (i.e. NSCL-96F037), D-68838 (Asta Medica), D-68836 (Asta Medica), Myoseverin B, D-43411 (Zentaris, i.e. D-81862), A-289099 (Abbott), A-318315 (Abbott), HTI-286 (i.e. SPA-110, trifluoroacetate salt) (Wyeth), D-82317 (Zentaris), D-82318 (Zentaris), SC-12983 (NCI), Resverastatin phosphate sodium, BPR-OY-007 (National Health Research Institutes), and SSR-250411 (Sanofi)), steroids (e.g., dexamethasone), finasteride, aromatase inhibitors, gonadotropin-releasing hormone agonists (GnRH) such as goserelin or leuprolide, adrenocorticosteroids (e.g., prednisone), progestins (e.g., hydroxyprogesterone caproate, megestrol acetate, medroxyprogesterone acetate), estrogens (e.g., diethylstilbestrol, ethinyl estradiol), antiestrogen (e.g., tamoxifen), androgens (e.g., testosterone propionate, fluoxymesterone), antiandrogen (e.g., flutamide), immunostimulants (e.g., *Bacillus* Calmette-Guerin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-*pseudomonas* exotoxin conjugate, etc.), radioimmunotherapy (e.g., anti-CD20 monoclonal antibody conjugated to $^{111}$In, $^{90}$Y, or $^{131}$I, etc.), triptolide, homoharringtonine, dactinomycin, doxorubicin, epirubicin, topotecan, itraconazole, vindesine, cerivastatin, vincristine, deoxyadenosine, sertraline, pitavastatin, irinotecan, clofazimine, 5-nonyloxytryptamine, vemurafenib, dabrafenib, erlotinib, gefitinib, EGFR inhibitors, epidermal growth factor receptor (EGFR)-targeted therapy or therapeutic (e.g. gefitinib (Iressa™), erlotinib (Tarceva™), cetuximab (Erbitux™), lapatinib (Tykerb™), panitumumab (Vectibix™), vandetanib (Caprelsa™), afatinib/BIBW2992, CI-1033/canertinib, neratinib/HKI-272, CP-724714, TAK-285, AST-1306, ARRY334543, ARRY-380, AG-1478, dacomitinib/PF299804, OSI-420/desmethyl erlotinib, AZD8931, AEE788, pelitinib/EKB-569, CUDC-101, WZ8040, WZ4002, WZ3146, AG-490, XL647, PD153035, BMS-599626), sorafenib, imatinib, sunitinib, dasatinib, or the like.

The terms "Chemotherapeutic" and "chemotherapeutic agent" are used in accordance with their plain and ordinary meaning and refer to a chemical composition or compound having antineoplastic properties or the ability to inhibit the growth or proliferation of cells.

"Cancer model organism", as used herein, is an organism exhibiting a phenotype indicative of cancer, or the activity of cancer causing elements, within the organism. A wide variety of organisms may serve as cancer model organisms, and include for example, cancer cells and mammalian organisms such as rodents (e.g. mouse or rat) and primates (such as humans). Cancer cell lines are widely understood by those skilled in the art as cells exhibiting phenotypes or genotypes similar to in vivo cancers. Cancer cell lines as used herein includes cell lines from animals (e.g. mice) and from humans.

The terms "ethanol withdrawal," "alcohol withdrawal," and "alcohol withdrawal syndrome" are used interchangeably herein and refer to diseases associated with and/or symptoms associated cessation of prolonged or excessive alcohol drinking. Symptoms may include, but are not limited to, anxiety, irritability, agitations, tremors, seizures, confusion, tachycardia, and infections.

"Neuropathic pain" is used according to its plain and ordinary meaning and refers to pain, both episodic and chronic, associated with nerve fiber damage, dysfunction, or injury.

The terms "depression" and "anxiety" are used according to their ordinary and common meanings.

The term "sigma 1 receptor" is used according to its ordinary meaning in the art and refers to a transmembrane protein capable of modulating release of calcium and neurotransmitter systems.

A sigma 1 receptor may be expressed in different tissues, and may be concentrated in areas of the central nervous system. Sigma 1 receptors may bind psychotropic drugs with high affinity. Sigma 1 receptors exhibit high affinity for (+)-benzomorphans and are typically classified by the receptor ligand specificity. Biol. Cell (2005) 97, 873-883; Current Pharmaceutical Design, 2012, 18, 884-901; Pharmacol. Ther. 2009 November; 124(2): 195-206.

The term "sigma 2 receptor" is used according to its ordinary meaning in the art and refers to a transmembrane protein capable of modulating release of calcium and neurotransmitter systems. A sigma 2 receptor may be expressed in different tissues, and may be concentrated in areas of the central nervous system. Sigma 2 receptors have lower affinity for the (+)-benzomorphans than Sigma 1 receptors and are implicated in apoptosis of cells. The sigma 2 receptor has been implicated in the treatment of AD. WO 2013/029057. The sigma 2 receptor may be progesterone receptor membrane component 1 (PGRMC1) (GI: 48146103). Mach, R. H. et. al. Nat Commun. 2011 Jul. 5; 2:380

I. Compositions

Provided herein are compositions having the formula:

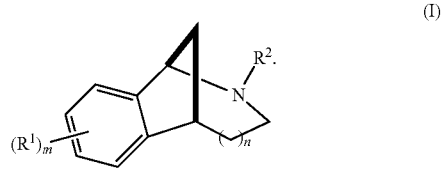

(I)

$R^1$ is hydrogen, halogen, —$N_3$, —$CF_3$, —$CCl_3$, —$CBr_3$, —$CI_3$, —CN, —C(O)$R^3$, —O$R^3$, N$R^3R^{3.4}$ C(O)O$R^3$, —C(O)N$R^3R^{3.4}$, —NO$_2$, —S$R^3$, —S(O)$_{n1}R^3$, —S(O)$_{n1}$O$R^3$, —S(O)$_{n1}$N$R^3R^{3.4}$, —NHN$R^3R^{3.4}$ ON$R^3R^{3.4}$, —NHC(O)NHN$R^3R^{3.4}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^2$ is hydrogen, halogen, —$N_3$, —$CF_3$, —$CCl_3$, —$CBr_3$, —$CI_3$, —CN, —C(O)$R^4$, —O$R^4$, —N$R^4R^{4.4}$, —C(O)O$R^4$, —C(O)N$R^4R^{4.4}$, —NO$_2$, —S$R^4$, —S(O)$_{n2}R^4$, —S(O)$_{n2}$O$R^4$, —S(O)$_{n2}$N$R^4R^{4.4}$, —NHN$R^4R^{4.4}$, —ON$R^4R^{4.4}$, —NHC(O)NHN$R^4R^{4.4}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. The symbols n1 and n2 are independently 1 or 2. The symbol m is 1, 2, 3 or 4. They symbol n is 1 or 2. $R^3$, $R^{3.4}$, $R^4$, $R^{4.4}$ are independently hydrogen, oxo, halogen, —$CF_3$, —CN, —OH, —NH$_2$, —COOH, —CONH$_2$, —NO$_2$, —SH, —S(O)$_2$Cl, —S(O)$_3$H, —S(O)$_4$H, —S(O)$_2$NH$_2$, —NHNH$_2$, —ONH$_2$, —NHC(O)NHNH$_2$, —NHC(O) NH$_2$, —NHS(O)$_2$ H, —NHC(O)H, —NHC(O)—OH, —NHOH, —OCF₃, —OCHF₂, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

The compound of formula (I) may have formula:

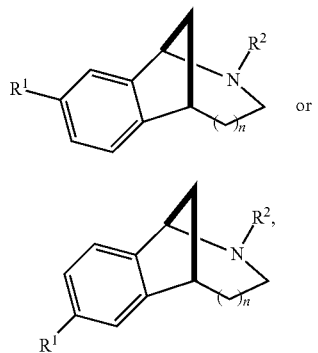

(II)

or (III)

where $R^1$ and $R^2$ are as described herein.

The compound of formula (I) may have the formula:

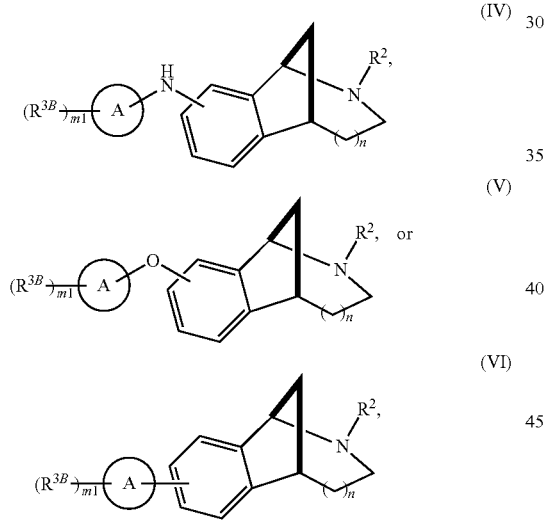

(IV)

(V)

(VI)

where $R^2$, $R^{3B}$, ring A, n, and m1 are as described herein.

The compound of formula (I) may have the formula:

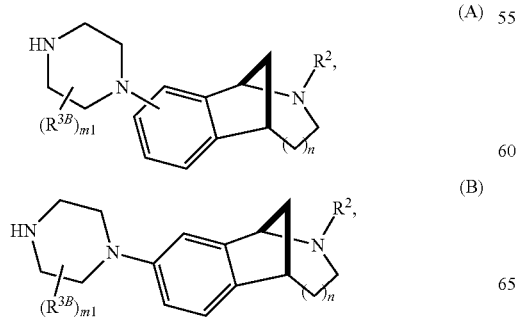

(A)

(B)

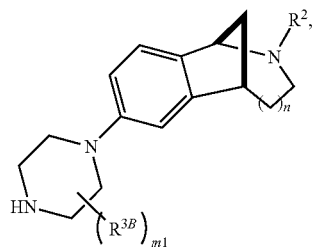

(C)

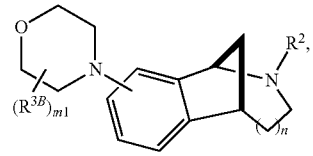

(D)

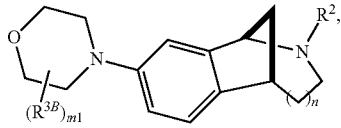

(E)

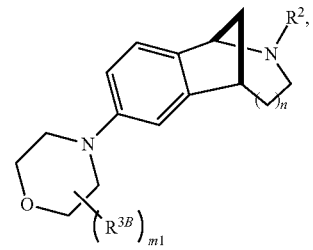

(F)

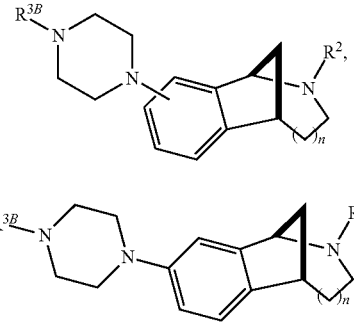

(G)

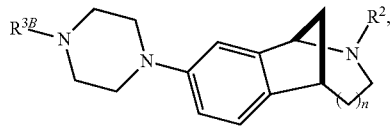

(H)

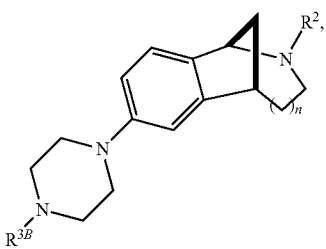

(I)

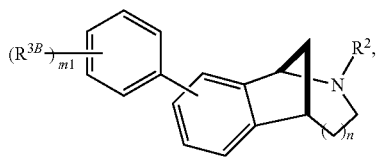

(J)

-continued

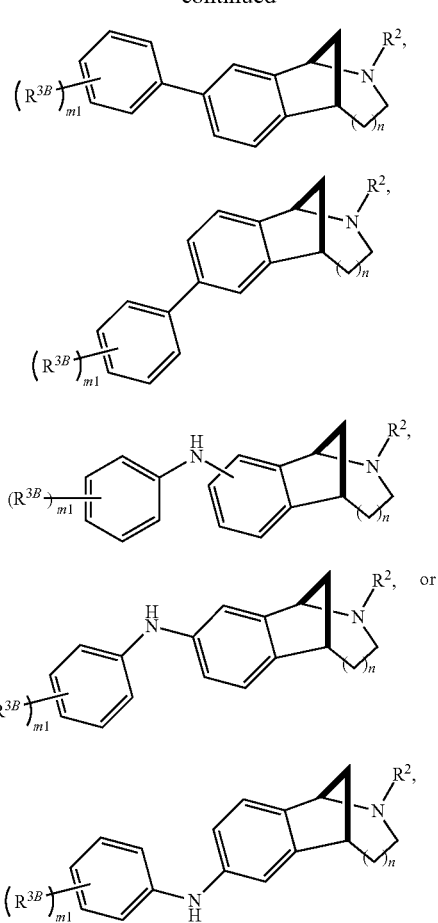

where R, R, n, and m1 are as described herein.

The compound of formula (I) may have the formula:

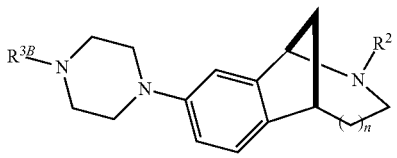

where $R^2$ and $R^{3B}$ are as described herein. $R^{3B}$ of formula (VII) may be substituted or unsubstituted alkyl. $R^{3B}$ of formula (VII) may be substituted or unsubstituted $C_1$-$C_{10}$ alkyl. $R^{3B}$ of formula (VII) may be unsubstituted $C_1$-$C_{10}$ alkyl. $R^{3B}$ of formula (VII) may be substituted $C_1$-$C_{10}$ alkyl. $R^{3B}$ of formula (VII) may be $R^{3C}$-substituted $C_1$-$C_{10}$ alkyl where $R^{3C}$ is as described herein. $R^{3B}$ of formula (VII) may be methyl. $R^2$ of formula (VII) may be —C(O)OR$^4$, where $R^4$ is $R^{4B}$-substituted or unsubstituted aryl, and $R^{4B}$ is halogen, —CF$_3$, —CN, —OH, unsubstituted alkyl, or unsubstituted heteroalkyl. $R^2$ of formula (VII) may be —C(O)OR$^4$, where $R^4$ is $R^{4B}$-substituted or unsubstituted aryl, and $R^{4B}$ is —CF$_3$, —CN, —OH, unsubstituted alkyl, or unsubstituted heteroalkyl. $R^4$ of formula (VII) may be unsubstituted phenyl.

Ring A may be aryl, heteroaryl, cycloalkyl, or heterocycloalkyl. Ring A may be aryl or heterocycloalkyl. Ring A may be aryl. Ring A may be 5 to 7 membered aryl. Ring A may be 5 or 6 membered aryl. Ring A may be 5 membered aryl. Ring A may be 6 membered aryl. Ring A may be heterocycloalkyl. Ring A may be 3 to 10 membered heterocycloalkyl. Ring A may be 3 to 8 membered heterocycloalkyl. Ring A may be 3 to 6 membered heterocycloalkyl. Ring A may be 3 membered heterocycloalkyl. Ring A may be 4 membered heterocycloalkyl. Ring A may be 5 membered heterocycloalkyl. Ring A may be 6 membered heterocycloalkyl.

The symbol n may be 1. The symbol n may be 2. The symbol n1 may be 1. The symbol n1 may be 2. The symbol n2 may be 1. The symbol n2 may be 2. The symbol m may be 1. The symbol m may be 2. The symbol m may be 3. The symbol m may be 4. The symbol m1 may be 0 or 1. The symbol m1 may be 0. The symbol m1 may be 1. The symbol m1 may be 2. The symbol m1 may be 3. The symbol m1 may be 4.

$R^1$ may be substituted or unsubstituted alkyl. $R^1$ may be substituted alkyl. $R^1$ may be unsubstituted alkyl. $R^1$ may be substituted or unsubstituted $C_1$-$C_{20}$ alkyl. $R^1$ may be substituted $C_1$-$C_{20}$ alkyl. $R^1$ may be unsubstituted $C_1$-$C_{20}$ alkyl. $R^1$ may be substituted or unsubstituted $C_1$-$C_{10}$ alkyl. $R^1$ may be substituted $C_1$-$C_{10}$ alkyl. $R^1$ may be unsubstituted $C_1$-$C_{10}$ alkyl. $R^1$ may be substituted or unsubstituted $C_1$-$C_5$ alkyl. $R^1$ may be substituted $C_1$-$C_5$ alkyl. $R^1$ may be unsubstituted $C_1$-$C_5$ alkyl. $R^1$ may be methyl, substituted or unsubstituted ethyl, or substituted or unsubstituted propyl. $R^1$ may be hydrogen. $R^1$ may be methyl.

$R^1$ may be $R^3$-substituted or unsubstituted alkyl. $R^1$ may be $R^3$-substituted alkyl. $R^1$ may be $R^3$-substituted or unsubstituted $C_1$-$C_{20}$ alkyl. $R^1$ may be $R^3$-substituted $C_1$-$C_{20}$ alkyl. $R^1$ may be $R^3$-substituted or unsubstituted $C_1$-$C_{10}$ alkyl. $R^1$ may be $R^3$-substituted $C_1$-$C_{10}$ alkyl. $R^1$ may be $R^3$-substituted or unsubstituted $C_1$-$C_5$ alkyl. $R^1$ may be $R^3$-substituted $C_1$-$C_5$ alkyl. $R^1$ may be methyl, $R^3$-substituted or unsubstituted ethyl, or $R^3$-substituted or unsubstituted propyl.

$R^1$ may be substituted or unsubstituted heteroalkyl. $R^1$ may be substituted heteroalkyl. $R^1$ may be unsubstituted heteroalkyl. $R^1$ may be substituted or unsubstituted 2 to 20 membered heteroalkyl. $R^1$ may be substituted 2 to 20 membered heteroalkyl. $R^1$ may be substituted or unsubstituted 2 to 10 membered heteroalkyl. $R^1$ may be substituted 2 to 10 membered heteroalkyl. $R^1$ may be substituted or unsubstituted 2 to 6 membered heteroalkyl. $R^1$ may be substituted 2 to 6 membered heteroalkyl.

$R^1$ may be $R^3$-substituted or unsubstituted heteroalkyl. $R^1$ may be $R^3$-substituted heteroalkyl. $R^1$ may be $R^3$-substituted or unsubstituted 2 to 20 membered heteroalkyl. $R^1$ may be $R^3$-substituted 2 to 20 membered heteroalkyl. $R^1$ may be $R^3$-substituted or unsubstituted 2 to 10 membered heteroalkyl. $R^1$ may be $R^3$-substituted 2 to 10 membered heteroalkyl. $R^1$ may be $R^3$-substituted or unsubstituted 2 to 6 membered heteroalkyl. $R^1$ may be $R^3$-substituted 2 to 6 membered heteroalkyl.

$R^1$ may be substituted or unsubstituted cycloalkyl. $R^1$ may be substituted cycloalkyl. $R^1$ may be unsubstituted cycloalkyl. $R^1$ may be substituted or unsubstituted 3 to 20 membered cycloalkyl. $R^1$ may be substituted 3 to 20 membered cycloalkyl. $R^1$ may be substituted or unsubstituted 3 to 10 membered cycloalkyl. $R^1$ may be substituted 3 to 10 membered cycloalkyl. $R^1$ may be substituted or unsubstituted 3 to 6 membered cycloalkyl. $R^1$ may be substituted 3 to 6 membered cycloalkyl.

$R^1$ may be $R^3$-substituted or unsubstituted cycloalkyl. $R^1$ may be $R^3$-substituted cycloalkyl. $R^1$ may be $R^3$-substituted or unsubstituted 3 to 20 membered cycloalkyl. $R^1$ may be $R^3$-substituted 3 to 20 membered cycloalkyl. $R^1$ may be $R^3$-substituted or unsubstituted 3 to 10 membered cycloalkyl. $R^1$ may be $R^3$-substituted 3 to 10 membered cycloalkyl. $R^1$ may be $R^3$-substituted or unsubstituted 3 to 6 membered cycloalkyl. $R^1$ may be $R^3$-substituted 3 to 6 membered cycloalkyl.

$R^1$ may be substituted or unsubstituted heterocycloalkyl. $R^1$ may be substituted heterocycloalkyl. $R^1$ may be unsubstituted heterocycloalkyl. $R^1$ may be substituted or unsubstituted 3 to 20 membered heterocycloalkyl. $R^1$ may be substituted 3 to 20 membered heterocycloalkyl. $R^1$ may be substituted or unsubstituted 3 to 10 membered heterocycloalkyl. $R^1$ may be substituted 3 to 10 membered heterocycloalkyl. $R^1$ may be substituted or unsubstituted 3 to 6 membered heterocycloalkyl. $R^1$ may be substituted 3 to 6 membered heterocycloalkyl.

$R^1$ may be $R^3$-substituted or unsubstituted heterocycloalkyl. $R^1$ may be $R^3$-substituted heterocycloalkyl. $R^1$ may be $R^3$-substituted or unsubstituted 3 to 20 membered heterocycloalkyl. $R^1$ may be $R^3$-substituted 3 to 20 membered heterocycloalkyl. $R^1$ may be $R^3$-substituted or unsubstituted 3 to 10 membered heterocycloalkyl. $R^1$ may be $R^3$-substituted 3 to 10 membered heterocycloalkyl. $R^1$ may be $R^3$-substituted or unsubstituted 3 to 6 membered heterocycloalkyl. $R^1$ may be $R^3$-substituted 3 to 6 membered heterocycloalkyl.

$R^1$ may be substituted or unsubstituted aryl. $R^1$ may be substituted aryl. $R^1$ may be unsubstituted aryl. $R^1$ may be substituted or unsubstituted 5 to 20 membered aryl. $R^1$ may be substituted 5 to 20 membered aryl. $R^1$ may be substituted or unsubstituted 5 to 8 membered aryl. $R^1$ may be substituted 5 to 8 membered aryl. $R^1$ may be substituted or unsubstituted 5 or 6 membered aryl. $R^1$ may be substituted 5 or 6 membered aryl (e.g. phenyl).

$R^1$ may be $R^3$-substituted or unsubstituted aryl. $R^1$ may be $R^3$-substituted aryl. $R^1$ may be $R^3$-substituted or unsubstituted 5 to 20 membered aryl. $R^1$ may be $R^3$-substituted 5 to 20 membered aryl. $R^1$ may be $R^3$-substituted or unsubstituted 5 to 8 membered aryl. $R^1$ may be $R^3$-substituted 5 to 8 membered aryl. $R^1$ may be $R^3$-substituted or unsubstituted 5 or 6 membered aryl. $R^1$ may be $R^3$-substituted 5 or 6 membered aryl (e.g. phenyl).

$R^1$ may be substituted or unsubstituted heteroaryl. $R^1$ may be substituted heteroaryl. $R^1$ may be unsubstituted heteroaryl. $R^1$ may be substituted or unsubstituted 5 to 20 membered heteroaryl. $R^1$ may be substituted 5 to 20 membered heteroaryl. $R^1$ may be substituted or unsubstituted 5 to 8 membered heteroaryl. $R^1$ may be substituted 5 to 8 membered heteroaryl. $R^1$ may be substituted or unsubstituted 5 or 6 membered heteroaryl. $R^1$ may be substituted 5 or 6 membered heteroaryl.

$R^1$ may be $R^3$-substituted or unsubstituted heteroaryl. $R^1$ may be $R^3$-substituted heteroaryl. $R^1$ may be $R^3$-substituted or unsubstituted 5 to 20 membered heteroaryl. $R^1$ may be $R^3$-substituted 5 to 20 membered heteroaryl. $R^1$ may be $R^3$-substituted or unsubstituted 5 to 8 membered heteroaryl. $R^1$ may be $R^3$-substituted 5 to 8 membered heteroaryl. $R^1$ may be $R^3$-substituted or unsubstituted 5 or 6 membered heteroaryl. $R^1$ may be $R^3$-substituted 5 or 6 membered heteroaryl.

$R^1$ may be halogen, $-N_3$, $-CF_3$, $-CCl_3$, $-CBr_3$, $-CI_3$, $-CN$, $-C(O)R^3$, $-OR^3$, $-NR^3R^{3A}$, $-C(O)OR^3$, $-C(O)NR^3R^{3A}$, $-NO_2$, $-SR^3$, $-S(O)_{n1}R^3$, $-S(O)_{n1}OR^3$, $-S(O)_{n1}NR^3R^{3A}$, $-NHNR^3R^{3A}$, $-ONR^3R^{3A}$, $-NHC(O)NHNR^3R^{3A}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. When the compound is a compound having formula (II) or formula (III), $R^1$ may be halogen, $-N_3$, $-CF_3$, $-CCl_3$, $-CBr_3$, $-CI_3$, $-CN$, $-C(O)R^3$, $-OR^3$, $-NR^3R^{3A}$, $-C(O)OR^3$, $-C(O)NR^3R^{3A}$, $-NO_2$, $-SR^3$, $-S(O)_{n1}R^3$, $-S(O)_{n1}OR^3$, $-S(O)_{n1}NR^3R^{3A}$, $-NHNR^3R^{3A}$, $-ONR^3R^{3A}$, $-NHC(O)NHNR^3R^{3A}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^1$ may be halogen, $-N_3$, $-CF_3$, $-CCl_3$, $-CBr_3$, $-CI_3$, $-CN$, $-C(O)R^3$, $-OR^3$, $-NR^3R^{3A}$, $-C(O)OR^3$, $-C(O)NR^3R^{3A}$, $-NO_2$, $-SR^3$, $-S(O)_{n1}R^3$, $-S(O)_{n1}R^3$, $-S(O)_{n1}NR^3R^{3A}$, $-NNR^3R^{3A}$, $-ONR^3R^{3A}$, $-NHC(O)NHNR^3R^{3A}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^1$ may be halogen. When the compound is a compound having formula (II) or formula (III), $R^1$ may be halogen, $-N_3$, $-CF_3$, $-CCl_3$, $-CBr_3$, $-CI_3$, $-CN$, $-C(O)R^3$, $-OR^3$, $-NR^3R^{3A}$, $-C(O)OR^3$, $-C(O)NR^3R^{3A}$, $-NO_2$, $-SR^3$, $-S(O)_{n1}R^3$, $-S(O)_{n1}OR^3$, $-S(O)_{n1}NR^3R^{3A}$, $-NHNR^3R^{3A}$, $-ONR^3R^{3A}$, $-NHC(O)NHNR^3R^{3A}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^1$ may be halogen, $-OR^3$, $-NR^3R^{3A}$, $-C(O)OR^3$, substituted or unsubstituted alkyl, substituted or unsubstituted cycloalkyl, substituted or unsubstituted heterocycloalkyl, substituted or unsubstituted aryl, substituted or unsubstituted heteroaryl.

$R^1$ may be halogen, $-OR^3$, $-NR^3R^{3A}$, substituted or unsubstituted alkyl, substituted or unsubstituted heterocycloalkyl, substituted or unsubstituted aryl, substituted or unsubstituted heteroaryl $R^1$ of the compounds described herein (e.g. formula (I), (II), (III)) may be Cl, F, Br, $-OH$, $-OR^3$, $-NR^3R^{3A}$, $R^3$-substituted or unsubstituted $C_1$-$C_{10}$alkyl, $R^3$-substituted or unsubstituted heterocycloalkyl, $R^3$-substituted or unsubstituted aryl, $R^3$-substituted or unsubstituted heteroaryl, were $R^{3A}$ is hydrogen, and $R^3$ is oxo, halogen, $-CF_3$, $-CN$, $-OH$, $-NH_2$, $-COOH$, $-CONH_2$, $-NO_2$, $-SH$, $-S(O)_2Cl$, $-S(O)_3H$, $-S(O)_4H$, $-S(O)_2NH_2$, $-NHNH_2$, $-ONH_2$, $-NHC(O)NHNH_2$, $-NHC(O)NH_2$, $-NHS(O)_2H$, $-NHC(O)H$, $-NHC(O)-OH$, $-NHOH$, $-OCF_3$, $-OCHF_2$, $R^{3B}$-substituted or unsubstituted alkyl, $R^{3B}$-substituted or unsubstituted heteroalkyl, $R^{3B}$-substituted or unsubstituted cycloalkyl, $R^{3B}$ substituted or unsubstituted heterocycloalkyl, $R^{3B}$-substituted or unsubstituted aryl, or $R^{3B}$ substituted or unsubstituted heteroaryl, and $R^{3B}$ is oxo, halogen, $-CF_3$, $-CN$, $-OH$, $-NH_2$, $-COOH$, $-CONH_2$, $-NO_2$, $-SH$, $-S(O)_2Cl$, $-S(O)_3H$, $-S(O)_4H$, $-S(O)_2NH_2$, $-NHNH_2$, $-ONH_2$, $-NHC(O)NHNH_2$, $-NHC(O)NH_2$, $-NHS(O)_2H$, $-NHC(O)H$, $-NHC(O)-OH$, $-NHOH$, $-OCF_3$, $-OCHF_2$, unsubstituted alkyl, unsubstituted heteroalkyl, unsubstituted cycloalkyl, unsubstituted heterocycloalkyl, unsubstituted aryl or unsubstituted heteroaryl.

$R^1$ of the compounds described herein (e.g. formula (I), (II), or (III)) may be Cl, F, Br, $-OH$, $-OR^3$, $-NR^3R^{3A}$, $R^3$-substituted or unsubstituted $C_1$-$C_{10}$ alkyl, $R^3$-substituted or unsubstituted heterocycloalkyl, $R^3$-substituted or unsubstituted aryl, $R^3$-substituted or unsubstituted heteroaryl, were $R^{3A}$ is hydrogen, $R^3$ is —$CF_3$, —CN, —OH, —$NH_2$, —$CONH_2$, —$S(O)_3H$, —$S(O)_2NH_2$, —NHC(O) $NH_2$, —NHC(O)H, $R^{3B}$-substituted or unsubstituted alkyl, $R^{3B}$-substituted or unsubstituted heteroalkyl, $R^{3B}$-substituted or unsubstituted cycloalkyl, $R^{3B}$-substituted or unsubstituted heterocycloalkyl, $R^{3B}$ substituted or unsubstituted aryl, or $R^{3B}$-substituted or unsubstituted heteroaryl, and $R^{3B}$ is —$CF_3$, —CN, —OH, —$NH_2$, —$CONH_2$, —$S(O)_3H$, —$S(O)_2NH_2$, —NHC(O) $NH_2$, —NHC(O)H, —$OCHF_2$, unsubstituted alkyl, unsubstituted heteroalkyl, unsubstituted cycloalkyl, unsubstituted heterocycloalkyl, unsubstituted aryl or unsubstituted heteroaryl.

$R^3$ is independently oxo, halogen, —$CF_3$, —CN, —OH, —$NH_2$, —COOH, —$CONH_2$, —$NO_2$, —SH, —$S(O)_2Cl$, —$S(O)_3H$, —$S(O)_4H$, —$S(O)_2NH_2$, —$NHNH_2$, —$ONH_2$, —$NHC(O)NHNH_2$, —NHC(O) $NH_2$, —$NHS(O)_2H$, —NHC(O)H, —NHC(O)—OH, —NHOH, —$OCF_3$, —$OCHF_2$, $R^{3B}$-substituted or unsubstituted alkyl, $R^{3B}$-substituted or unsubstituted heteroalkyl, $R^{3B}$-substituted or unsubstituted cycloalkyl, $R^{3B}$ substituted or unsubstituted heterocycloalkyl, $R^{3B}$-substituted or unsubstituted aryl, or $R^{3B}$ substituted or unsubstituted heteroaryl.

$R^3$ may independently be —$CF_3$, —CN, —OH, —$NH_2$, —COOH, —$CONH_2$, —$S(O)_3H$, —$S(O)_2NH_2$, —NHC(O) $NH_2$, —NHC(O)H, $R^{3B}$-substituted or unsubstituted alkyl, $R^{3B}$-substituted or unsubstituted heteroalkyl, $R^{3B}$-substituted or unsubstituted cycloalkyl, $R^{3B}$-substituted or unsubstituted heterocycloalkyl, $R^{3B}$-substituted or unsubstituted aryl, or $R^{3B}$-substituted or unsubstituted heteroaryl.

$R^{3B}$ is independently oxo, halogen, —$CF_3$, —CN, —OH, —$NH_2$, —COOH, —$CONH_2$, —$NO_2$, —SH, —$S(O)_2Cl$, —$S(O)_3H$, —$S(O)_4H$, —$S(O)_2NH_2$, —$NHNH_2$, —$ONH_2$, —$NHC(O)NHNH_2$, —NHC(O) $NH_2$, —$NHS(O)_2H$, —NHC(O)H, —NHC(O)—OH, —NHOH, —$OCF_3$, —$OCHF_2$, $R^{3C}$-substituted or unsubstituted alkyl, $R^{3C}$-substituted or unsubstituted heteroalkyl, $R^{3C}$-substituted or unsubstituted cycloalkyl, $R^{3C}$-substituted or unsubstituted heterocycloalkyl, $R^{3C}$-substituted or unsubstituted aryl, or $R^{3C}$ substituted or unsubstituted heteroaryl.

$R^{3B}$ may independently be —$CF_3$, —CN, —OH, —$NH_2$, —$CONH_2$, —$S(O)_3H$, —$S(O)_2NH_2$, —$NHC(O)NH_2$, —NHC(O)H, unsubstituted alkyl, unsubstituted heteroalkyl, unsubstituted cycloalkyl, unsubstituted heterocycloalkyl, unsubstituted aryl, or unsubstituted heteroaryl.

$R^{3B}$ may independently be —$CF_3$, —CN, —OH, —$NH_2$, —COOH, —$CONH_2$, —$NO_2$, —SH, —$S(O)_3H$, —$S(O)_4H$, —$S(O)_2NH_2$, —$NHNH_2$, —$ONH_2$, —$NHC(O)NHNH_2$, —NHC(O) $NH_2$, —$NHS(O)_2H$, —NHC(O)H, —NHC(O)—OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl or unsubstituted heteroaryl. $R^{3B}$ may be halogen, —$CF_3$, —CN, —OH, unsubstituted alkyl or unsubstituted heteroalkyl. $R^{3B}$ may be —$CF_3$, —CN, —OH, unsubstituted alkyl or unsubstituted heteroalkyl. $R^{3B}$ may be halogen, —$CF_3$, —OH, —$OCH_3$ or unsubstituted $C_1$-$C_5$ alkyl. $R^{3B}$ may be —$CF_3$, —OH, —$OCH_3$ or unsubstituted $C_1$-$C_5$ alkyl.

$R^{3B}$ of the compounds described herein (e.g. formula (IV), (V), (VI), (VII), or (A)-(O)) may be —$CF_3$, —CN, —OH, —$NH_2$, —COOH, —$CONH_2$, —$NO_2$, —SH, —$S(O)_3H$, —$S(O)_4H$, —$S(O)_2NH_2$, —$NHNH_2$, —$ONH_2$, —NHC(O) $NHNH_2$, —NHC(O) $NH_2$, —$NHS(O)_2H$, —NHC(O)H, —NHC(O)—OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl or unsubstituted heteroaryl, where ring A is aryl, heteroaryl, cycloalkyl, or heterocycloalkyl, and m1 is 0, 1, 2, 3, or 4.

$R^{3B}$ of the compounds described herein (e.g. formula (IV), (V), (VI), (VII), or (A)-(O)) may be —$CF_3$, —CN, —OH, —$NH_2$, —COOH, —$CONH_2$, —$NO_2$, —SH, —$S(O)_2Cl$, —$S(O)_3H$, —$S(O)_4H$, —$S(O)_2NH_2$, —$NHNH_2$, —$ONH_2$, —$NHC(O)NHNH_2$, —NHC(O) $NH_2$, —$NHS(O)_2H$, —NHC(O)H, —NHC(O)—OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl or unsubstituted heteroaryl. $R^{3B}$ may be halogen, —$CF_3$, —CN, —OH, unsubstituted alkyl or unsubstituted heteroalkyl. $R^{3B}$ may be —$CF_3$, —CN, —OH, unsubstituted alkyl or unsubstituted heteroalkyl. $R^{3B}$ may be halogen, —$CF_3$, —OH, —$OCH_3$ or unsubstituted $C_1$-$C_5$ alkyl. $R^{3B}$ may be —$CF_3$, —OH, —$OCH_3$ or unsubstituted $C_1$-$C_5$ alkyl.

$R^{3C}$ is independently oxo, halogen, —$CF_3$, —CN, —OH, —$NH_2$, —$CONH_2$, —$NO_2$, —SH, —$S(O)_2Cl$, —$S(O)_3H$, —$S(O)_4H$, —$S(O)_2NH_2$, —$NHNH_2$, —$ONH_2$, —NHC(O) $NHNH_2$, —NHC(O) $NH_2$, —$NHS(O)_2H$, —NHC(O)H, —NHC(O)—OH, —NHOH, —$OCF_3$, —$OCHF_2$, $R^{3D}$-substituted or unsubstituted alkyl, $R^{3D}$ substituted or unsubstituted heteroalkyl, $R^{3D}$-substituted or unsubstituted cycloalkyl, $R^{3D}$-substituted or unsubstituted heterocycloalkyl, $R^{3D}$-substituted or unsubstituted aryl, or $R^{3D}$-substituted or unsubstituted heteroaryl.

$R^{3D}$ is independently oxo, halogen, —$CF_3$, —CN, —OH, —$NH_2$, —$CONH_2$, —$NO_2$, —SH, —$S(O)_2Cl$, —$S(O)_3H$, —$S(O)_4H$, —$S(O)_2NH_2$, —$NHNH_2$, —$ONH_2$, —NHC(O) $NHNH_2$, —NHC(O) $NH_2$, —$NHS(O)_2H$, —NHC(O)H, —NHC(O)—OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, or unsubstituted heteroaryl.

$R^2$ may be substituted or unsubstituted alkyl. $R^2$ may be substituted alkyl. $R^2$ may be unsubstituted alkyl. $R^2$ may be substituted or unsubstituted $C_1$-$C_{20}$ alkyl. $R^2$ may be substituted $C_1$-$C_{20}$ alkyl. $R^2$ may be unsubstituted $C_1$-$C_{20}$ alkyl. $R^2$ may be substituted or unsubstituted $C_1$-$C_{10}$ alkyl. $R^2$ may be substituted $C_1$-$C_{10}$ alkyl. $R^2$ may be unsubstituted $C_1$-$C_{10}$ alkyl. $R^2$ may be substituted or unsubstituted $C_1$-$C_5$ alkyl. $R^2$ may be substituted $C_1$-$C_5$ alkyl. $R^2$ may be unsubstituted $C_1$-$C_5$ alkyl. $R^2$ may be methyl, substituted or unsubstituted ethyl, or substituted or unsubstituted propyl. $R^2$ may be hydrogen. $R^2$ may be methyl.

$R^2$ may be $R^4$-substituted or unsubstituted alkyl. $R^2$ may be $R^4$-substituted alkyl. $R^2$ may be $R^4$-substituted or unsubstituted $C_1$-$C_{20}$ alkyl. $R^2$ may be $R^4$-substituted $C_1$-$C_{20}$ alkyl. $R^2$ may be $R^4$-substituted or unsubstituted $C_1$-$C_{10}$ alkyl. $R^2$ may be $R^4$-substituted $C_1$-$C_{10}$ alkyl. $R^2$ may be $R^4$-substituted or unsubstituted $C_1$-$C_5$ alkyl. $R^2$ may be $R^4$-substituted $C_1$-$C_5$ alkyl. $R^2$ may be methyl, $R^4$-substituted or unsubstituted ethyl, or $R^4$-substituted or unsubstituted propyl.

$R^2$ may be substituted or unsubstituted heteroalkyl. $R^2$ may be substituted heteroalkyl. $R^2$ may be unsubstituted heteroalkyl. $R^2$ may be substituted or unsubstituted 2 to 20 membered heteroalkyl. $R^2$ may be substituted 2 to 20 membered heteroalkyl. $R^2$ may be substituted or unsubstituted 2 to 10 membered heteroalkyl. $R^2$ may be substituted 2 to 10 membered heteroalkyl. $R^2$ may be substituted or unsubstituted 2 to 6 membered heteroalkyl. $R^2$ may be substituted 2 to 6 membered heteroalkyl.

$R^2$ may be $R^4$-substituted or unsubstituted heteroalkyl. $R^2$ may be $R^4$-substituted heteroalkyl. $R^2$ may be $R^4$-substituted or unsubstituted 2 to 20 membered heteroalkyl. $R^2$ may be $R^4$-substituted 2 to 20 membered heteroalkyl. $R^2$ may be $R^4$-substituted or unsubstituted 2 to 10 membered heteroalkyl. $R^2$ may be $R^4$-substituted 2 to 10 membered heteroalkyl. $R^2$ may be $R^4$-substituted or unsubstituted 2 to 6 membered heteroalkyl. $R^2$ may be $R^4$-substituted 2 to 6 membered heteroalkyl.

$R^2$ may be substituted or unsubstituted cycloalkyl. $R^2$ may be substituted cycloalkyl. $R^2$ may be unsubstituted cycloalkyl. $R^2$ may be substituted or unsubstituted 3 to 20 membered cycloalkyl. $R^2$ may be substituted 3 to 20 membered cycloalkyl. $R^2$ may be substituted or unsubstituted 3 to 10 membered cycloalkyl. $R^2$ may be substituted 3 to 10 membered cycloalkyl. $R^2$ may be substituted or unsubstituted 3 to 6 membered cycloalkyl. $R^2$ may be substituted 3 to 6 membered cycloalkyl.

$R^2$ may be $R^4$-substituted or unsubstituted cycloalkyl. $R^2$ may be $R^4$-substituted cycloalkyl. $R^2$ may be $R^4$-substituted or unsubstituted 3 to 20 membered cycloalkyl. $R^2$ may be $R^4$-substituted 3 to 20 membered cycloalkyl. $R^2$ may be $R^4$-substituted or unsubstituted 3 to 10 membered cycloalkyl. $R^2$ may be $R^4$-substituted 3 to 10 membered cycloalkyl. $R^2$ may be $R^4$-substituted or unsubstituted 3 to 6 membered cycloalkyl. $R^2$ may be $R^4$-substituted 3 to 6 membered cycloalkyl.

$R^2$ may be substituted or unsubstituted heterocycloalkyl. $R^2$ may be substituted heterocycloalkyl. $R^2$ may be unsubstituted heterocycloalkyl. $R^2$ may be substituted or unsubstituted 3 to 20 membered heterocycloalkyl. $R^2$ may be substituted 3 to 20 membered heterocycloalkyl. $R^2$ may be substituted or unsubstituted 3 to 10 membered heterocycloalkyl. $R^2$ may be substituted 3 to 10 membered heterocycloalkyl. $R^2$ may be substituted or unsubstituted 3 to 6 membered heterocycloalkyl. $R^2$ may be substituted 3 to 6 membered heterocycloalkyl.

$R^2$ may be $R^4$-substituted or unsubstituted heterocycloalkyl. $R^2$ may be $R^4$-substituted heterocycloalkyl. $R^2$ may be $R^4$-substituted or unsubstituted 3 to 20 membered heterocycloalkyl. $R^2$ may be $R^4$-substituted 3 to 20 membered heterocycloalkyl. $R^2$ may be $R^4$-substituted or unsubstituted 3 to 10 membered heterocycloalkyl. $R^2$ may be $R^4$-substituted 3 to 10 membered heterocycloalkyl. $R^2$ may be $R^4$-substituted or unsubstituted 3 to 6 membered heterocycloalkyl. $R^2$ may be $R^4$-substituted 3 to 6 membered heterocycloalkyl.

$R^2$ may be substituted or unsubstituted aryl. $R^2$ may be substituted aryl. $R^2$ may be unsubstituted aryl. $R^2$ may be substituted or unsubstituted 5 to 20 membered aryl. $R^2$ may be substituted 5 to 20 membered aryl. $R^2$ may be substituted or unsubstituted 5 to 8 membered aryl. $R^2$ may be substituted 5 to 8 membered aryl. $R^2$ may be substituted or unsubstituted 5 or 6 membered aryl. $R^2$ may be substituted 5 or 6 membered aryl (e.g. phenyl).

$R^2$ may be $R^4$-substituted or unsubstituted aryl. $R^2$ may be $R^4$-substituted aryl. $R^2$ may be $R^4$-substituted or unsubstituted 5 to 20 membered aryl. $R^2$ may be $R^4$-substituted 5 to 20 membered aryl. $R^2$ may be $R^4$-substituted or unsubstituted 5 to 8 membered aryl. $R^2$ may be $R^4$-substituted 5 to 8 membered aryl. $R^2$ may be $R^4$-substituted or unsubstituted 5 or 6 membered aryl. $R^2$ may be $R^4$-substituted 5 or 6 membered aryl (e.g. phenyl).

$R^2$ may be substituted or unsubstituted heteroaryl. $R^2$ may be substituted heteroaryl. $R^2$ may be unsubstituted heteroaryl. $R^2$ may be substituted or unsubstituted 5 to 20 membered heteroaryl. $R^2$ may be substituted 5 to 20 membered heteroaryl. $R^2$ may be substituted or unsubstituted 5 to 8 membered heteroaryl. $R^2$ may be substituted 5 to 8 membered heteroaryl. $R^2$ may be substituted or unsubstituted 5 or 6 membered heteroaryl. $R^2$ may be substituted 5 or 6 membered heteroaryl.

$R^2$ may be $R^4$-substituted or unsubstituted heteroaryl. $R^2$ may be $R^4$-substituted heteroaryl. $R^2$ may be $R^4$-substituted or unsubstituted 5 to 20 membered heteroaryl. $R^2$ may be $R^4$-substituted 5 to 20 membered heteroaryl. $R^2$ may be $R^4$-substituted or unsubstituted 5 to 8 membered heteroaryl. $R^2$ may be $R^4$-substituted 5 to 8 membered heteroaryl. $R^2$ may be $R^4$-substituted or unsubstituted 5 or 6 membered heteroaryl. $R^2$ may be $R^4$-substituted 5 or 6 membered heteroaryl.

$R^2$ may be halogen, $-N_3$, $-CF_3$, $-CCl_3$, $-CBr_3$, $-CI_3$, $-CN$, $-C(O)R^4$, $-OR^4$, $-NR^4R^{4A}$, $-C(O)OR^4$, $-C(O)NR^4R^{4A}$, $-NO_2$, $-SR^4$, $-S(O)_2R^4$, $-S(O)_{n2}OR^4$, $-S(O)_{n2}NR^4R^{4A}$, $-NHNR^4R^{4A}$ $-ONR^4R^{4A}$, $-NHC(O)NHNR^4R^{4A}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^2$ of the compound of formula (II) or formula (III) may be halogen, $-N_3$, $-CF_3$, $-CCl_3$, $-CBr_3$, $-CI_3$, $-CN$, $-C(O)R^4$, $-OR^4$, $-NR^4R^{4A}$, $-C(O)OR^4$, $-C(O)NR^4R^{4A}$, $-NO_2$, $-SR^4$, $-S(O)_{n2}R^4$, $-S(O)_2OR^4$, $-S(O)_{n2}NR^4R^{4A}$, $-NHNR^4R^{4A}$, $-ONR^4R^{4A}$, $-NHC(O)NHNR^4R^{4A}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^2$ may be halogen, $-CN$, $-C(O)R^4$, $-OR^4$, $-NR^4R^{4A}$, $-C(O)OR^4$, $-C(O)NR^4R^{4A}$, $-S(O)_{n2}R^4$, $-S(O)_2OR^4$, $-S(O)_{n2}NR^4R^{4A}$, $-ONR^4R^{4A}$, $-NHC(O)NHNR^4R^{4A}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^2$ may be halogen, $-OR^4$, $-NR^4R^{4A}$, $-C(O)OR^4$, substituted or unsubstituted alkyl, substituted or unsubstituted cycloalkyl, substituted or unsubstituted heterocycloalkyl, substituted or unsubstituted aryl, substituted or unsubstituted heteroaryl. $R^2$ may be $-OR^4$, $-NR^4R^{4A}$, $-C(O)OR^4$, substituted or unsubstituted alkyl, substituted or unsubstituted cycloalkyl, substituted or unsubstituted heterocycloalkyl, substituted or unsubstituted aryl, substituted or unsubstituted heteroaryl.

$R^2$ may be halogen, $-OR^4$, $-NR^4R^{4A}$, $-C(O)OR^4$, substituted or unsubstituted alkyl, substituted or unsubstituted heterocycloalkyl, substituted or unsubstituted aryl, substituted or unsubstituted heteroaryl. $R^2$ may be $-OR^4$, $-NR^4R^{4A}$, $-C(O)OR^4$, substituted or unsubstituted alkyl, substituted or unsubstituted heterocycloalkyl, substituted or unsubstituted aryl, substituted or unsubstituted heteroaryl.

$R^2$ may be —C(O)OR$^4$, where $R^4$ is as described herein. $R^2$ may be —C(O)OR$^4$, where $R^4$ is $R^{4B}$-substituted or unsubstituted aryl, and $R^{4B}$ is halogen, —CF$_3$, —CN, —OH, unsubstituted alkyl or unsubstituted heteroalkyl. $R^2$ may be —C(O)OR$^4$, where $R^4$ is $R^{4B}$-substituted or unsubstituted aryl, and $R^{4B}$ is —CF$_3$, —CN, —OH, unsubstituted alkyl or unsubstituted heteroalkyl. $R^4$ may be unsubstituted aryl. $R^4$ may be $R^{4B}$-substituted or unsubstituted phenyl. $R^4$ may be unsubstituted phenyl.

$R^2$ may be $R^{4B}$-substituted or unsubstituted alkyl, where $R^{4B}$ is $R^{4C}$-substituted or unsubstituted aryl, and $R^{4C}$ is halogen, —CF$_3$, —CN, —OH, unsubstituted alkyl or unsubstituted heteroalkyl. $R^{4C}$ may be unsubstituted aryl.

$R^4$ may independently be —CF$_3$, —CN, —OH, —NH$_2$, —COOH, —CONH$_2$, —S(O)$_3$H, —S(O)$_2$NH$_2$, —NHC(O)NH$_2$, —NHC(O)H, $R^{4B}$-substituted or unsubstituted alkyl, $R^{4B}$-substituted or unsubstituted heteroalkyl, $R^{4B}$-substituted or unsubstituted cycloalkyl, $R^{4B}$-substituted or unsubstituted heterocycloalkyl, $R^{4B}$-substituted or unsubstituted aryl, or $R^{4B}$-substituted or unsubstituted heteroaryl.

$R^{4B}$ is independently oxo, halogen, —CF$_3$, —CN, —OH, —NH$_2$, —COOH, —CONH$_2$, —NO$_2$, —SH, —S(O)$_2$Cl, —S(O)$_3$H, —S(O)$_4$H, —S(O)$_2$NH$_2$, —NHNH$_2$, —ONH$_2$, —NHC(O)NHNH$_2$, —NHC(O) NH$_2$, —NHS(O)$_2$H, —NHC(O)H, —NHC(O)—OH, —NHOH, —OCF$_3$, —OCHF$_2$, $R^{4C}$-substituted or unsubstituted alkyl, $R^{4C}$-substituted or unsubstituted heteroalkyl, $R^{4C}$-substituted or unsubstituted cycloalkyl, $R^{4C}$-substituted or unsubstituted heterocycloalkyl, $R^{4C}$-substituted or unsubstituted aryl, or $R^{4C}$-substituted or unsubstituted heteroaryl.

$R^{4B}$ may independently be —CF$_3$, —CN, —OH, —NH$_2$, —CONH$_2$, —S(O)$_3$H, —S(O)$_2$NH$_2$, —NHC(O)NH$_2$, —NHC(O)H, unsubstituted alkyl, unsubstituted heteroalkyl, unsubstituted cycloalkyl, unsubstituted heterocycloalkyl, unsubstituted aryl, or unsubstituted heteroaryl.

$R^{4C}$ is independently oxo, halogen, —CF$_3$, —CN, —OH, —NH$_2$, —CONH$_2$, —NO$_2$, —SH, —S(O)$_2$Cl, —S(O)$_3$H, —S(O)$_4$H, —S(O)$_2$NH$_2$, —NHNH$_2$, —ONH$_2$, —NHC(O)NHNH$_2$, —NHC(O) NH$_2$, —NHS(O)$_2$H, —NHC(O)H, —NHC(O)—OH, —NHOH, —OCF$_3$, —OCHF$_2$, $R^{4D}$-substituted or unsubstituted alkyl, $R^{4D}$ substituted or unsubstituted heteroalkyl, $R^{4D}$-substituted or unsubstituted cycloalkyl, $R^{4D}$-substituted or unsubstituted heterocycloalkyl, $R^{4D}$-substituted or unsubstituted aryl, or $R^{4D}$-substituted or unsubstituted heteroaryl.

$R^{4D}$ is independently oxo, halogen, —CF$_3$, —CN, —OH, —NH$_2$, —CONH$_2$, —NO$_2$, —SH, —S(O)$_2$Cl, —S(O)$_3$H, —S(O)$_4$H, —S(O)$_2$NH$_2$, —NHNH$_2$, —ONH$_2$, —NHC(O) NHNH$_2$, —NHC(O) NH$_2$, —NHS(O)$_2$H, —NHC(O)H, —NHC(O)—OH, —NHOH, —OCF$_3$, —OClF$_2$, unsubstituted alkyl, unsubstituted heteroalkyl, unsubstituted cycloalkyl, unsubstituted heterocycloalkyl, unsubstituted aryl, or unsubstituted heteroaryl.

The compound may have formula:

(JJS-1-166)

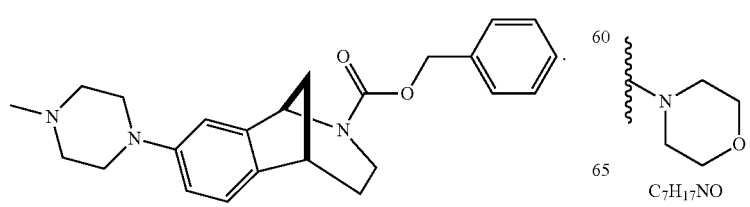

The compound may have the formula as set forth in Table A:

TABLE A

| R1 | R2 |
|---|---|
| ![piperazine-Me] C$_8$H$_{20}$N$_2$ | Cbz |
| ![NH-phenyl] C$_9$H$_{15}$N | Bn |
| ![piperazine-Me] C$_8$H$_{20}$N$_2$ | H |
| ![morpholine] C$_7$H$_{17}$NO | 4-dimethylaminobenzyl |
| ![morpholine] C$_7$H$_{17}$NO | 3,4-dimethoxybenzyl |
| ![morpholine] C$_7$H$_{17}$NO | 3,4-dichlorobenzyl |
| ![morpholine] C$_7$H$_{17}$NO | 2-fluorobenzyl |

TABLE A-continued

| R1 | R2 |
|---|---|
| morpholinyl (C₇H₁₇NO) | Me |
| morpholinyl (C₇H₁₇NO) | Phenethyl |
| 4-(trifluoromethyl)phenyl (C₁₀H₁₃F₃) | Bn |
| 4-(trifluoromethyl)phenyl (C₁₀H₁₃F₃) | H |
| morpholinyl (C₇H₁₇NO) | 3,5-dichlorobenzyl |
| 4-methylpiperazinyl (C₈H₂₀N₂) | Alloc |
| 4-methylpiperazinyl (C₈H₂₀N₂) | cyclohexanecarbonyl |
| 4-methylpiperazinyl (C₈H₂₀N₂) | phenylacetyl |
| 4-methylpiperazinyl (C₈H₂₀N₂) | benzoyl |
| 4-methylpiperazinyl (C₈H₂₀N₂) | 3-phenylpropanoyl |
| 4-methylpiperazinyl (C₈H₂₀N₂) | phenylsulfonyl |
| 4-methylpiperazinyl (C₈H₂₀N₂) | pyridine-2-carbonyl |
| 4-methylpiperazinyl (C₈H₂₀N₂) | phenoxycarbonyl |
| 4-methylpiperazinyl (C₈H₂₀N₂) | 2-methoxy-5-methylbenzoyl |

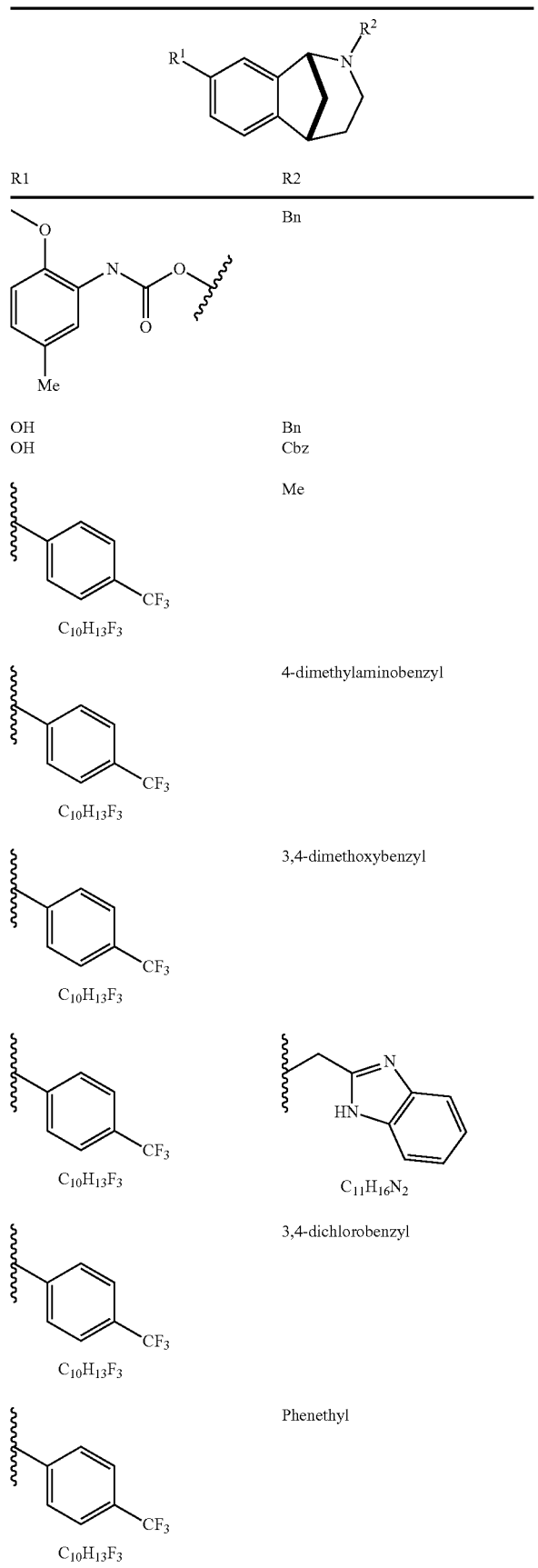
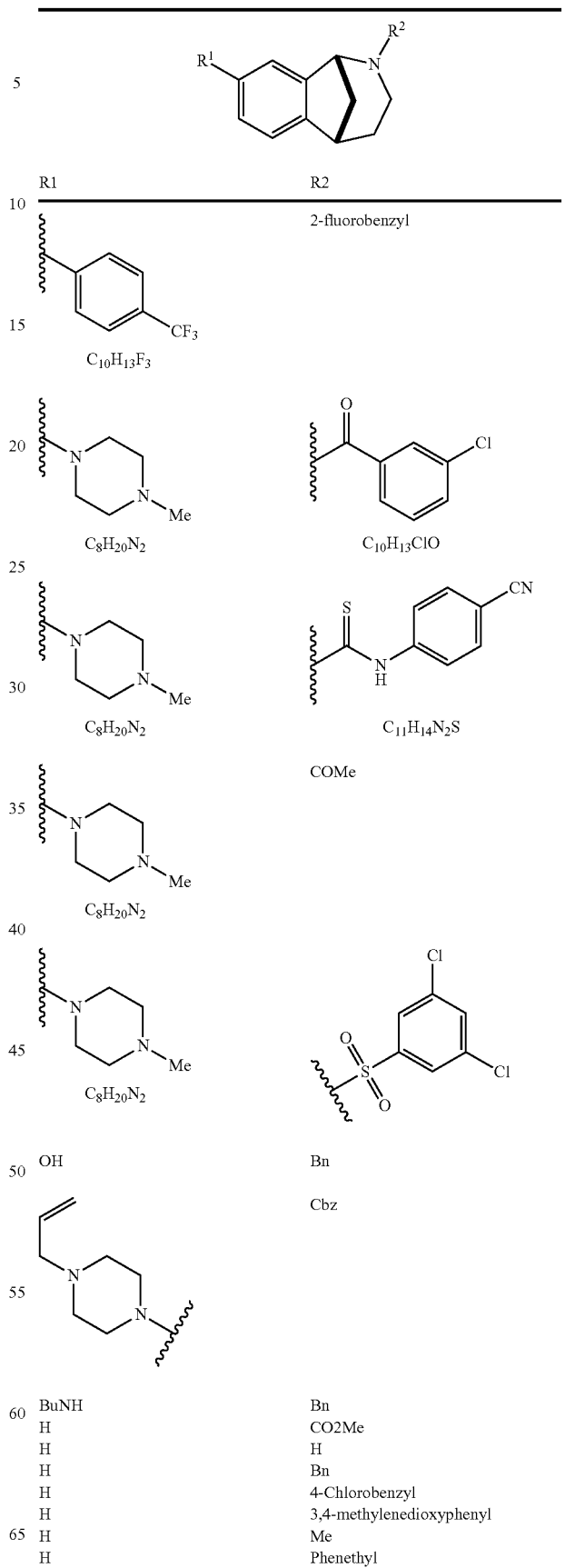

TABLE A-continued

[Structure: bicyclic with R1 on benzene and R2 on N, bridged system]

| R1 | R2 |
|---|---|
| phenoxy (C9H14O) | Bn |
| N-methyl-N-phenylamino (C10H17N) | Cbz |
| N-methyl-N-phenylamino (C10H17N) | Bn |

The compound may have the formula as set forth in Table B:

TABLE B

[Structure: bicyclic with R1 on benzene and R2 on N, bridged system]

| R1 | R2 |
|---|---|
| 3-methoxyphenyl | Cbz |
| 3-methoxyphenyl | Bn |
| 3-hydroxyphenyl | Cbz |
| 3-hydroxyphenyl | Bn |
| 4-methoxyphenyl | Cbz |
| 4-methoxyphenyl | Bn |

The compound may have the formula as set forth in Table C:

TABLE C

[Structure: bicyclic with R1 on benzene and R2 on N, bridged system with larger ring]

| R1 | R2 |
|---|---|
| Cl | 4-pyridylmethyl |
| Cl | 3-pyridylmethyl |
| Cl | 2-pyridylmethyl |
| Cl | 4-dimethylaminobenzyl |
| Cl | phthalimido-butyl |
| Cl | aminopentyl (-(CH2)4-NH2) |
| Cl | cyclohexylmethyl |
| OH | Cbz |
| OH | Bn |
| 3-methylphenyl | Cbz |
| 3-methylphenyl | Bn |
| 3-methylphenyl | H |
| Cl | phenethyl |

TABLE C-continued

| R1 | R2 |
|---|---|
| 3-methylphenyl | pyridin-3-ylmethyl |
| 3-methylphenyl | -(CH2)3-C(O)OMe |
| 4-(trifluoromethyl)phenyl | Cbz |
| 4-(trifluoromethyl)phenyl | H |
| 4-(trifluoromethyl)phenyl | -(CH2)3-C(O)OMe |
| 4-(trifluoromethyl)phenyl | -(CH2)4-OH |
| 4-(trifluoromethyl)phenyl | cyclopentyl |
| morpholin-4-yl | Cbz |
| morpholin-4-yl | H |
| morpholin-4-yl | 3,5-dichlorobenzyl |
| morpholin-4-yl | 4-chlorobenzyl |
| morpholin-4-yl | 3-(N-methylcarbamoylmethoxy)benzyl |
| Cl | H |
| morpholin-4-yl | -(CH2)3-C(O)OMe |
| morpholin-4-yl | -(CH2)2-C(O)OEt |
| morpholin-4-yl | 4-(N-methylcarbamoyl)benzyl |
| morpholin-4-yl | 3-(methoxycarbonylmethoxy)benzyl |
| morpholin-4-yl | -(CH2)2-C(O)OH |
| 4-(trifluoromethyl)phenyl | -(CH2)2-C(O)OH |

TABLE C-continued

| R1 | R2 |
|---|---|
| Cl | N-methylpiperidin-4-yl |
| Cl | cyclopentylmethyl |
| Cl | Bn |
| morpholino | (1-methyl-1H-imidazol-5-yl)methyl |
| morpholino | 4-(methoxycarbonyl)benzyl |
| Cl | cyclobutyl |
| Cl | Me |
| 4-CF3-phenyl | 3-hydroxypropyl |
| 4-CF3-phenyl | butyl |
| 4-CF3-phenyl | (3-methyloxetan-3-yl)methyl |
| 4-CF3-phenyl | cyclobutyl |
| 4-CF3-phenyl | 4-(OTBS)butyl |
| Cl | 4-chlorobenzyl |
| Cl | 4-hydroxybenzyl |
| 4-CF3-phenyl | 4-hydroxybutyl |
| Cl | H |
| morpholino | 2-(N-methylcarbamoyl)ethyl |

In embodiments, the compound is not:

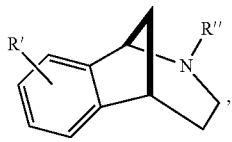

(X)

where R' is halogen, substituted or unsubstituted heteroalkyl, substituted or unsubstituted aryl or substituted or unsubstituted heterocycloalkyl and R" is —C(S)alkyl, —C(O)aryl, —S(O)₂aryl, substituted or unsubstituted aryl or substituted or unsubstituted heteroalkyl. In embodiments, the compound is not formula (X) where R' is halogen and R" is Cbz or Bn. In embodiments, the compound is not formula (X) where R' is substituted or unsubstituted heteroalkyl and R" is Cbz or Bn. In embodiments, the compound is not formula (X) where R' is substituted or unsubstituted aryl and R" is Cbz or Bn. In embodiments, the compound is not formula (X) where R' is substituted or unsubstituted heteroalkyl and R" is —C(S)alkyl, —C(O)aryl, —S(O)₂aryl. In embodiments, the compound is not formula (X) where R' is substituted or unsubstituted aryl and R" is —C(S)alkyl, —C(O)aryl, —S(O)₂aryl.

In embodiments, the compound is not:
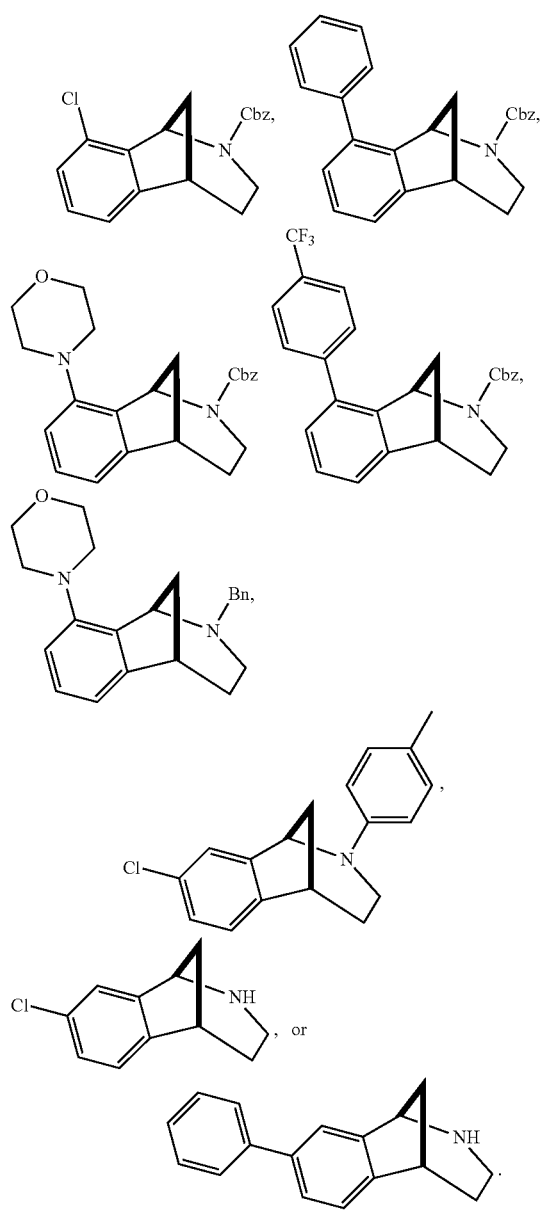
In embodiments, the compound is not:
Scheme 1
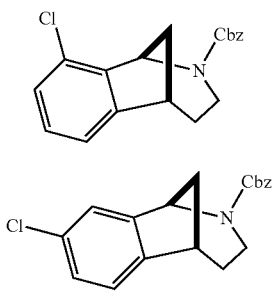
-continued
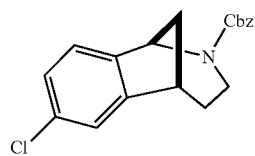
18{1}
TABLE 1
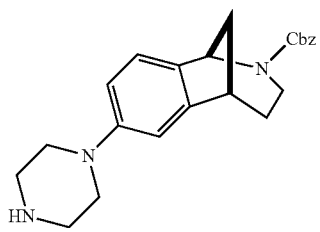 [SMILES: O=C(OCc1ccccc1)N1CC[C@@H]2C[C@@H]1c1ccc(N3CCNCC3)cc12]
20{1, 1}
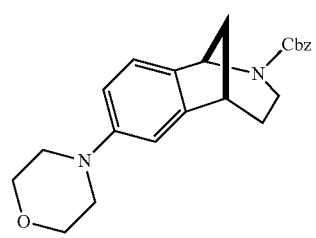 [SMILES: O=C(OCc1ccccc1)N1CC[C@@H]2C[C@@H]1c1ccc(N3CCOCC3)cc12]
20{1, 2}
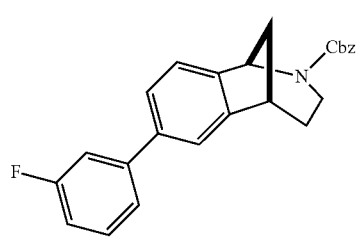 [SMILES: O=C(OCc1ccccc1)N1CC[C@@H]2C[C@@H]1c1ccc(-c3cccc(F)c3)cc12]
20{1, 5}
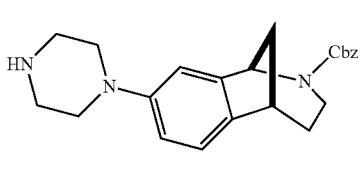 [SMILES: O=C(OCc1ccccc1)N1CC[C@@H]2C[C@@H]1c1cc(N3CCNCC3)ccc12]
20{2, 1}
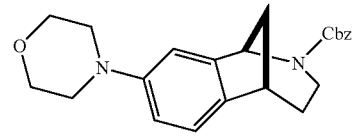 [SMILES: O=C(OCc1ccccc1)N1CC[C@@H]2C[C@@H]1c1cc(N3CCOCC3)ccc12]
20{2, 2}
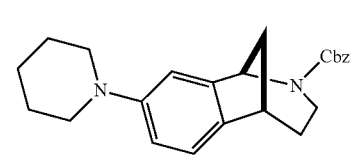 [SMILES: O=C(OCc1ccccc1)N1CC[C@@H]2C[C@@H]1c1cc(N3CCCCC3)ccc12]
20{2, 3}
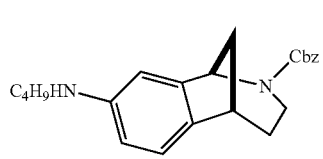
20{2, 4}

TABLE 1-continued
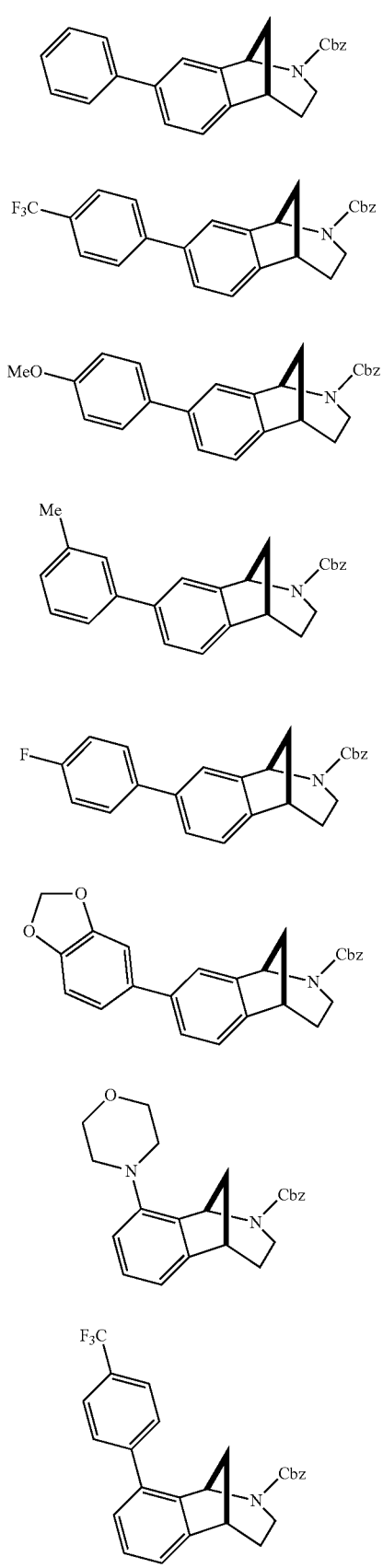
| | |
|---|---|
| | 20{2, 6} |
| | 20{2, 7} |
| | 20{2, 8} |
| | 20{2, 9} |
| | 20{2, 10} |
| | 20{2, 11} |
| | 20{3, 2} |
| | 20{3, 7} |
TABLE 1-continued
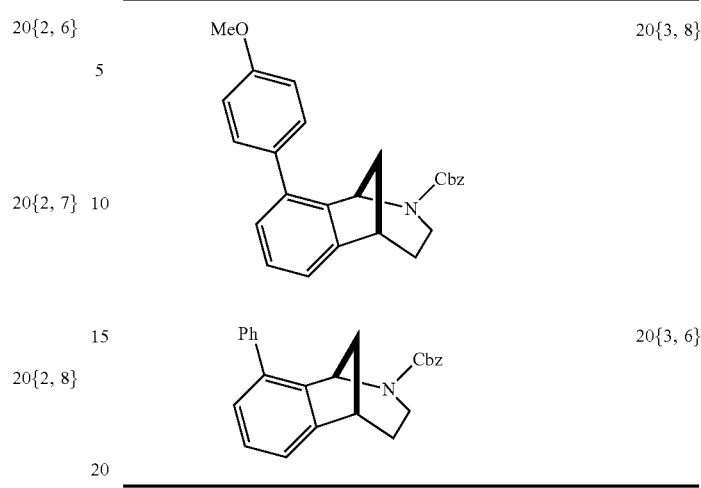
| | |
|---|---|
| | 20{3, 8} |
| | 20{3, 6} |
TABLE 2
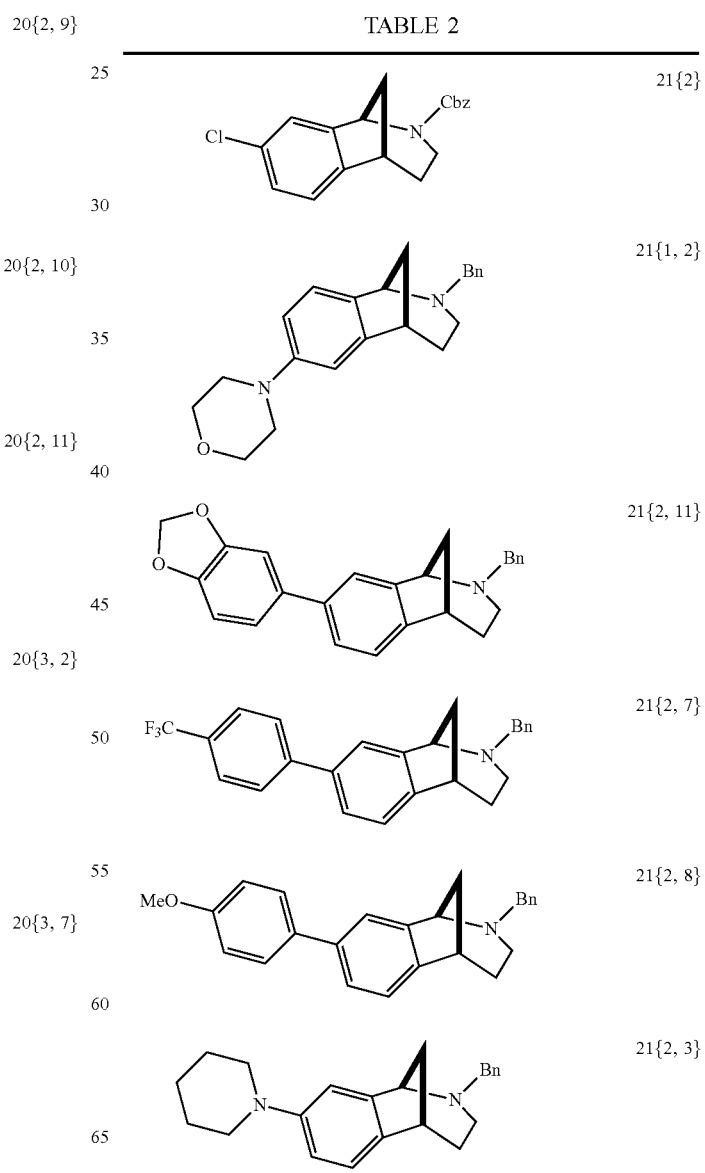
| | |
|---|---|
| | 21{2} |
| | 21{1, 2} |
| | 21{2, 11} |
| | 21{2, 7} |
| | 21{2, 8} |
| | 21{2, 3} |

TABLE 2-continued
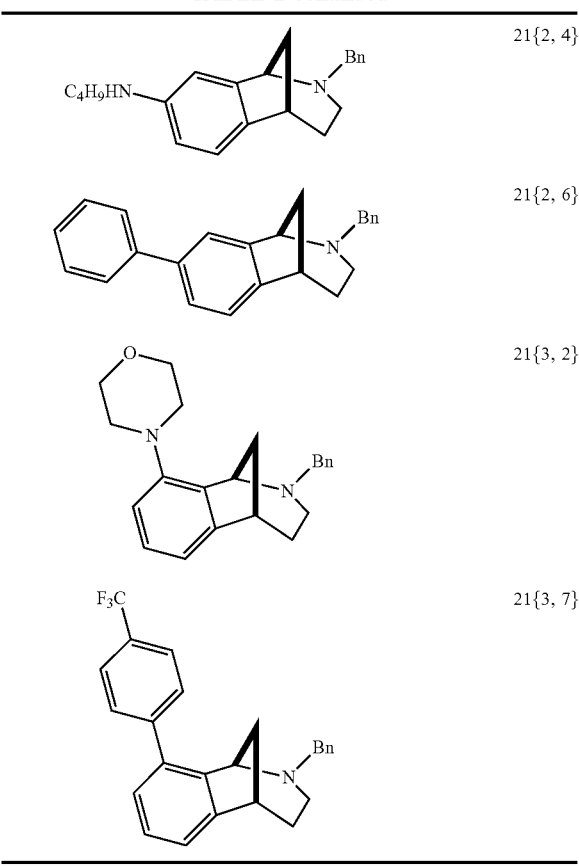
TABLE 3
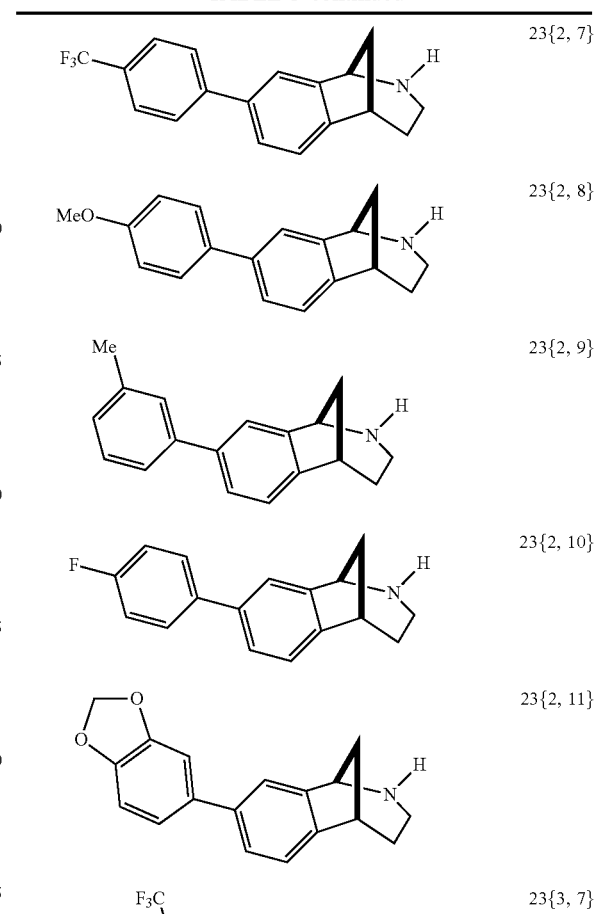
TABLE 3-continued
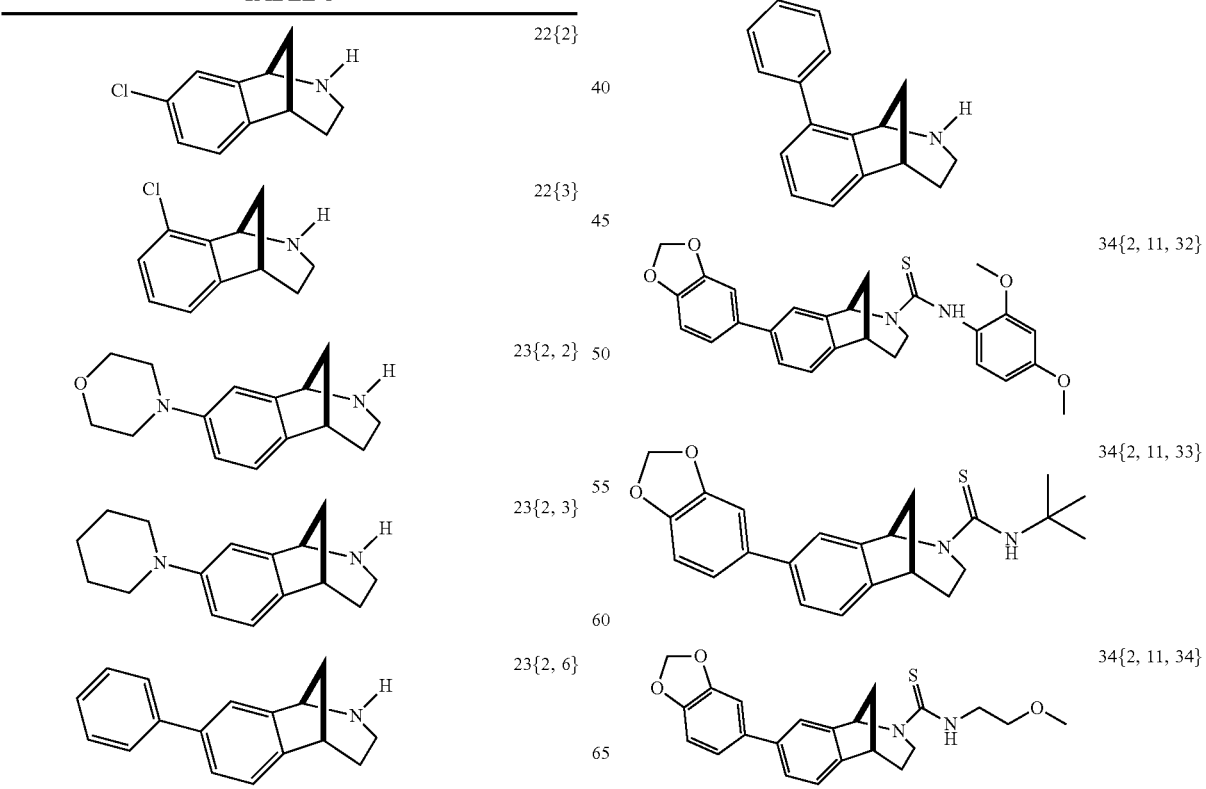

TABLE 3-continued
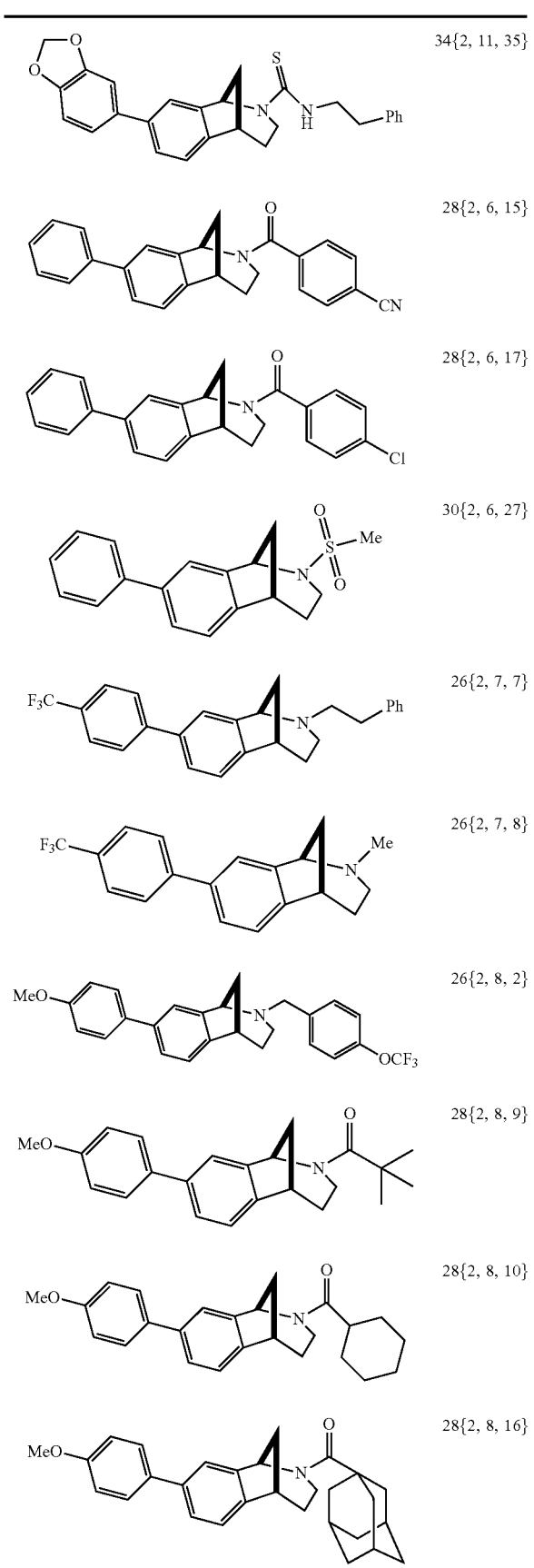
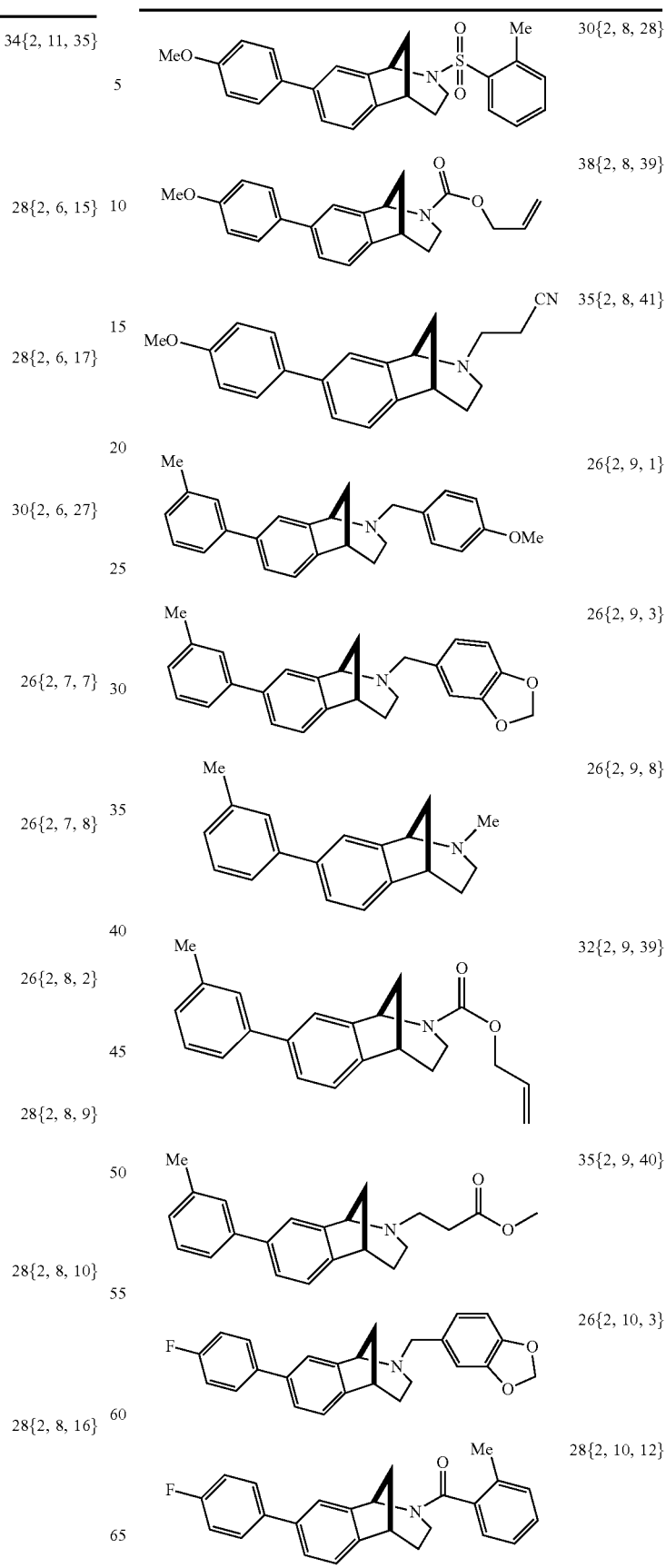

TABLE 3-continued
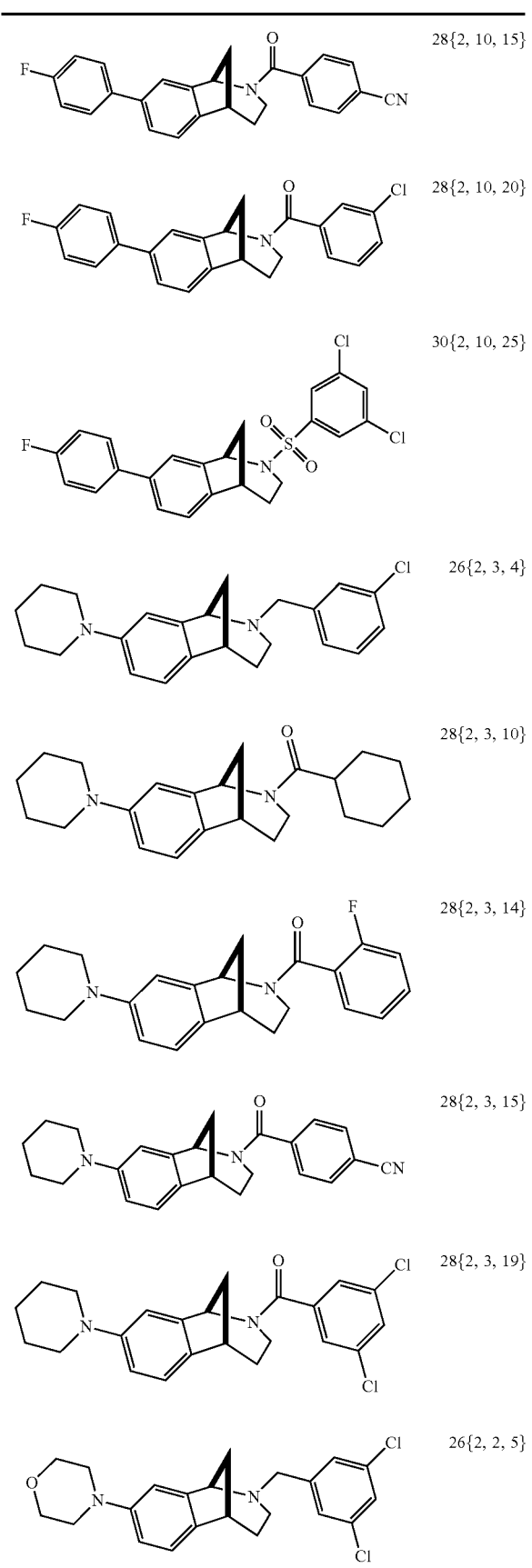
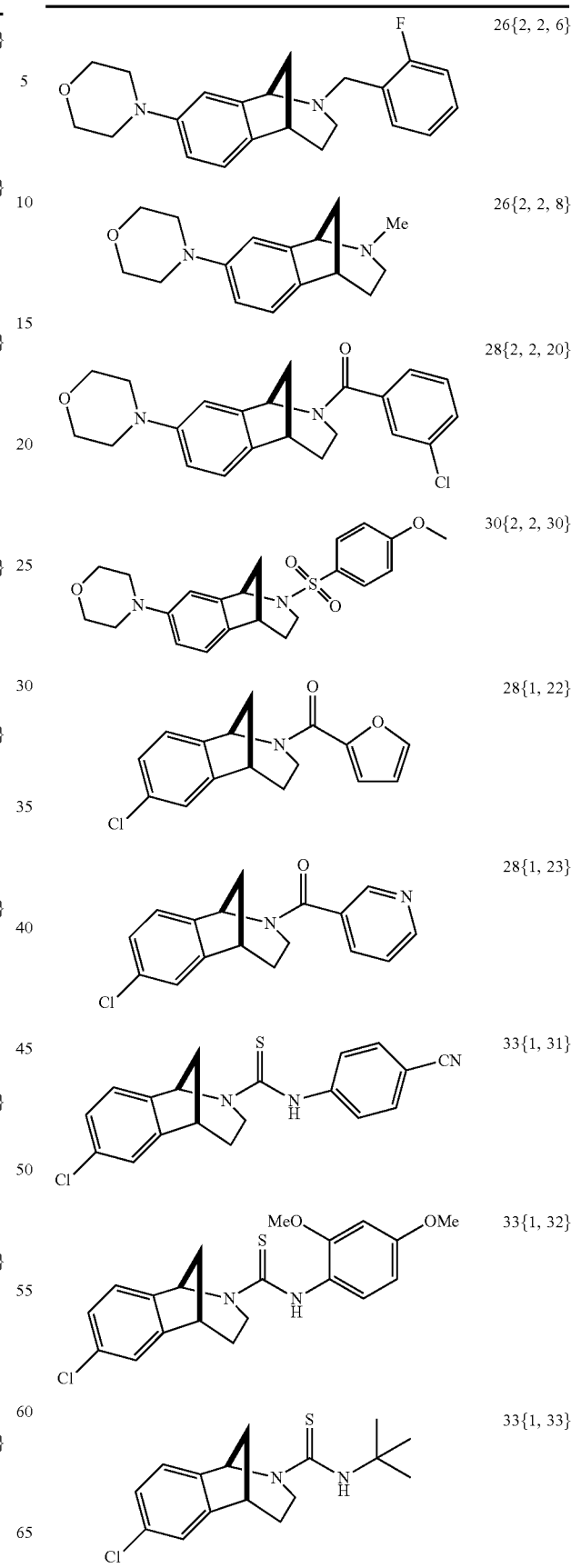

TABLE 3-continued
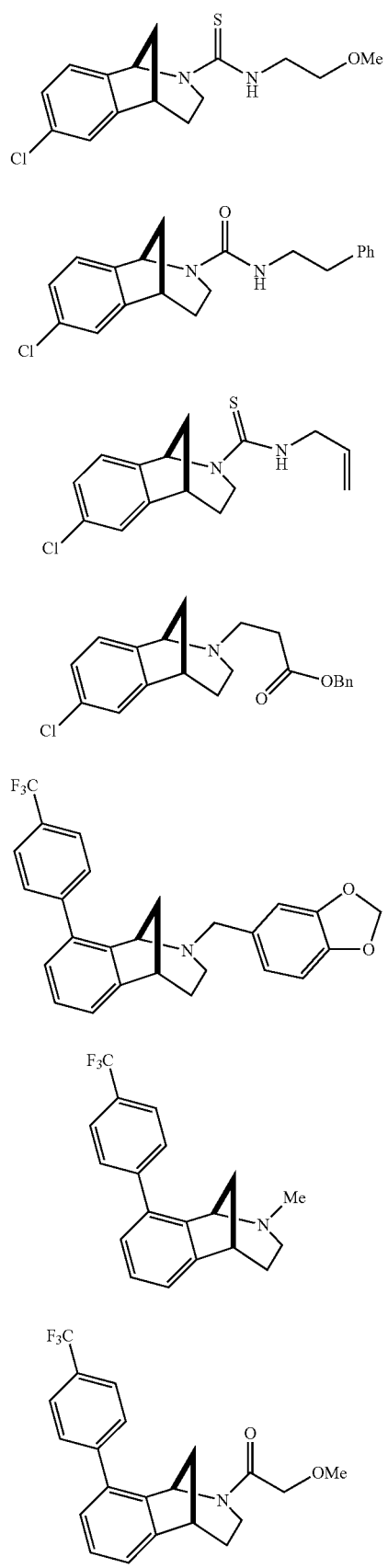
33{1, 34}
33{1, 35}
33{1, 36}
36{1, 42}
26{3, 7, 3}
26{3, 7, 8}
28{3, 7, 11}
TABLE 3-continued
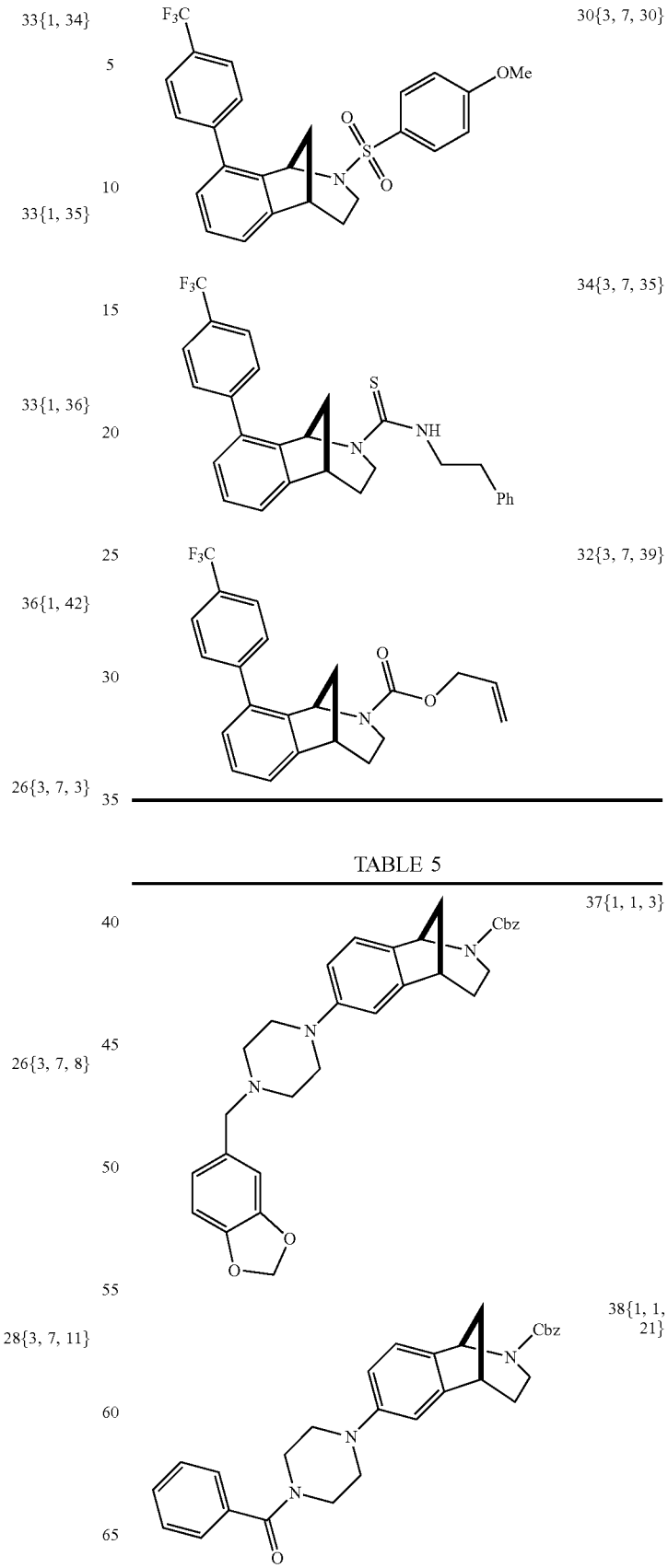
30{3, 7, 30}
34{3, 7, 35}
32{3, 7, 39}
TABLE 5
37{1, 1, 3}
38{1, 1, 21}

TABLE 5-continued

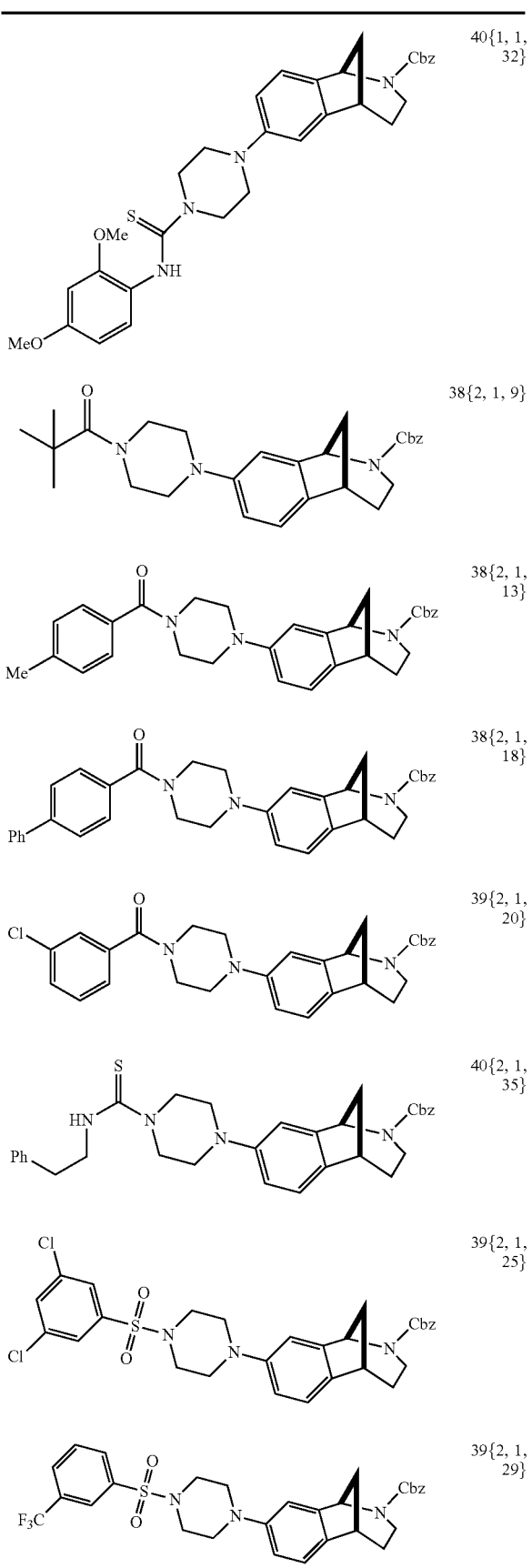

TABLE 5-continued

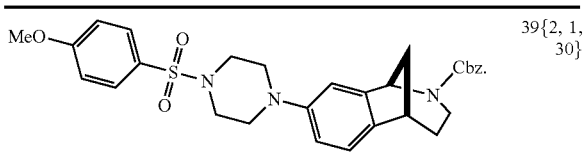

II. Pharmaceutical Compositions

Provided herein are pharmaceutical compositions of the compounds herein. In one aspect is a pharmaceutical composition that includes a compound described herein and a pharmaceutically acceptable excipient. In another aspect is a pharmaceutical compositions that includes a compound described herein and a pharmaceutically acceptable excipient or a pharmaceutically acceptable salt. The compound may have formula (I) as described herein. The compound may have formula (II) as described herein. The compound may have formula (III) as described herein. The compound may have formula (IV) as described herein. The compound may have formula (V) as described herein. The compound may have formula (VI) as described herein. The compound may have formula (VII) as described herein. The compound may be a compound set forth in Table A, Table B, or Table C.

The pharmaceutical composition may include a second agent in a therapeutically effective amount. The pharmaceutical composition may include a second agent where the second agent treats cancer. The second agent may be an anti-cancer agent as described herein. The pharmaceutical composition may include a second agent where the second agent treats a neurodegenerative disease (e.g. Alzheimer's Disease or ALS). The pharmaceutical composition may include a second agent where the second agent treats alcohol withdrawal. The pharmaceutical composition may include a second agent where the second agent treats depression or anxiety. The pharmaceutical composition may include a second agent where the second agent treats neuropathic pain.

1. Formulations

The pharmaceutical composition may be prepared and administered in a wide variety of dosage formulations. Compounds described herein (e.g. formula (I), (II), (III), (IV), (V), (VI), (VII) or (A)-(O)) may be administered orally, rectally, or by injection (e.g. intravenously, intramuscularly, intracutaneously, subcutaneously, intraduodenally, or intraperitoneally).

For preparing pharmaceutical compositions from compounds described herein, pharmaceutically acceptable carriers can be either solid or liquid. Solid form preparations include powders, tablets, pills, capsules, cachets, suppositories, and dispersible granules. A solid carrier may be one or more substance that may also act as diluents, flavoring agents, binders, preservatives, tablet disintegrating agents, or an encapsulating material.

In powders, the carrier may be a finely divided solid in a mixture with the finely divided active component. In tablets, the active component may be mixed with the carrier having the necessary binding properties in suitable proportions and compacted in the shape and size desired.

The powders and tablets preferably contain from 5% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizers, and thickening agents as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations that are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component.

The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 10000 mg according to the particular application and the potency of the active component. The composition can, if desired, also contain other compatible therapeutic agents.

Some compounds may have limited solubility in water and therefore may require a surfactant or other appropriate co-solvent in the composition. Such co-solvents include: Polysorbate 20, 60, and 80; Pluronic F-68, F-84, and P-103; cyclodextrin; and polyoxyl 35 castor oil. Such co-solvents are typically employed at a level between about 0.01% and about 2% by weight. Viscosity greater than that of simple aqueous solutions may be desirable to decrease variability in dispensing the formulations, to decrease physical separation of components of a suspension or emulsion of formulation, and/or otherwise to improve the formulation. Such viscosity building agents include, for example, polyvinyl alcohol, polyvinyl pyrrolidone, methyl cellulose, hydroxy propyl methylcellulose, hydroxyethyl cellulose, carboxymethyl cellulose, hydroxy propyl cellulose, chondroitin sulfate and salts thereof, hyaluronic acid and salts thereof, and combinations of the foregoing. Such agents are typically employed at a level between about 0.01% and about 2% by weight.

The pharmaceutical compositions may additionally include components to provide sustained release and/or comfort. Such components include high molecular weight, anionic mucomimetic polymers, gelling polysaccharides, and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes.

The pharmaceutical composition may be intended for intravenous use. The pharmaceutically acceptable excipient can include buffers to adjust the pH to a desirable range for intravenous use. Many buffers including salts of inorganic acids such as phosphate, borate, and sulfate are known.

2. Effective Dosages

The pharmaceutical composition may include compositions wherein the active ingredient is contained in a therapeutically effective amount, i.e., in an amount effective to achieve its intended purpose. The actual amount effective for a particular application will depend, inter alia, on the condition being treated.

The dosage and frequency (single or multiple doses) of compounds administered can vary depending upon a variety of factors, including route of administration; size, age, sex, health, body weight, body mass index, and diet of the recipient; nature and extent of symptoms of the disease being treated; presence of other diseases or other health-related problems; kind of concurrent treatment; and complications from any disease or treatment regimen. Other therapeutic regimens or agents can be used in conjunction with the methods and compounds disclosed herein.

For any compound described herein or combination thereof, the therapeutically effective amounts can be initially determined from cell culture assays. Target concentrations will be those concentrations of active compound(s) that are capable of increasing the extent of cancer cell death as measured, for example, using methods known in the art.

Therapeutically effective amounts for use in humans may be determined from animal models. For example, a dose for humans can be formulated to achieve a concentration that has been found to be effective in animals. The dosage in humans can be adjusted by monitoring response of the cancer to the treatment and adjusting the dosage upwards or downwards, as described above.

Dosages may be varied depending upon the requirements of the subject and the compound being employed. The dose administered to a subject, in the context of the pharmaceutical compositions presented herein, should be sufficient to effect a beneficial therapeutic response in the subject over time. The size of the dose also will be determined by the existence, nature, and extent of any adverse side effects. Generally, treatment is initiated with smaller dosages, which are less than the optimum dose of the compound. Thereafter, the dosage is increased by small increments until the optimum effect under circumstances is reached.

Dosage amounts and intervals can be adjusted individually to provide levels of the administered compounds effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is entirely effective to treat the clinical symptoms demonstrated by the particular patient. This planning should involve the careful choice of active compound by considering factors such as compound potency, relative bioavailability, patient body weight, presence and severity of adverse side effects, preferred mode of administration, and the toxicity profile of the selected agent.

3. Toxicity

The ratio between toxicity and therapeutic effect for a particular compound is its therapeutic index and can be expressed as the ratio between $LD_{50}$ (the amount of compound lethal in 50% of the population) and $ED_{50}$ (the amount of compound effective in 50% of the population). Compounds that exhibit high therapeutic indices are preferred. Therapeutic index data obtained from cell culture assays and/or animal studies can be used in formulating a range of dosages for use in humans. The dosage of such compounds preferably lies within a range of plasma concentrations that include the $ED_{50}$ with little or no toxicity. The dosage may vary within this range depending upon the dosage form employed and the route of administration utilized. See, e.g. Fingl et al., In: THE PHARMACOLOGICAL BASIS OF THERAPEUTICS, Ch. 1, p. 1, 1975. The exact formulation, route of administration, and dosage can be chosen by the individual physician in view of the patient's condition and the particular method in which the compound is used.

When parenteral application is needed or desired, particularly suitable admixtures for the compounds included in the pharmaceutical composition may be injectable, sterile solutions, oily or aqueous solutions, as well as suspensions, emulsions, or implants, including suppositories. In particular, carriers for parenteral administration include aqueous solutions of dextrose, saline, pure water, ethanol, glycerol, propylene glycol, peanut oil, sesame oil, polyoxyethyleneblock polymers, and the like. Ampoules are convenient unit dosages. Pharmaceutical admixtures suitable for use in the pharmaceutical compositions presented herein may include those described, for example, in Pharmaceutical Sciences (17th Ed., Mack Pub. Co., Easton, Pa.) and WO 96/05309, the teachings of both of which are hereby incorporated by reference.

III. Method of Treatment

Further provided herein are methods of treating a disease in a subject in need thereof. In one aspect, is a method of treating cancer in a subject in need thereof, by administering an effective amount of a compound described herein. The cancer may be breast cancer, triple-negative breast cancer, ovarian cancer, lung cancer, prostate cancer, or skin cancer. The cancer may be breast cancer. The cancer may be triple-negative breast cancer. The cancer may be ovarian cancer. The cancer may be lung cancer. The cancer may be prostate cancer. The cancer may be skin cancer. The method may include co-administering the compounds described herein with another active pharmaceutical agent as described herein. The compound may be a compound having formula (I). The compound may be a compound having formula (VII).

In another aspect is a method of treating neurodegenerative disease in a subject in need thereof by administering an effective amount of a compound described herein. The neurodegenerative disease may be Alzheimer's disease or Amyotrophic lateral sclerosis (ALS). The neurodegenerative disease may be Alzheimer's disease. The neurodegenerative disease may be Amyotrophic lateral sclerosis (ALS). The method may include co-administering the compounds described herein with another active pharmaceutical agent as described herein. The compound may have formula:

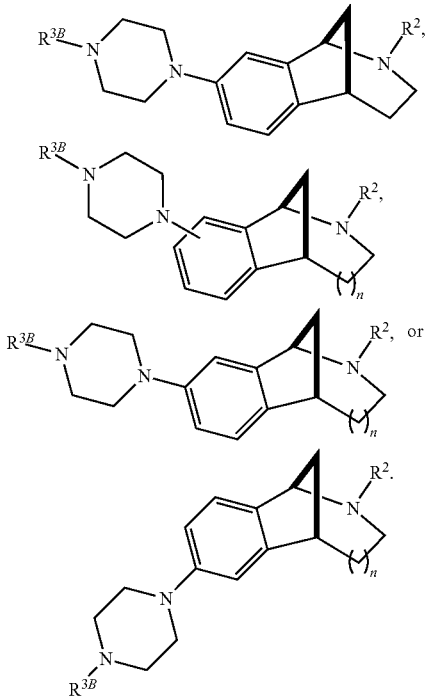

$R^2$, $R^{3B}$, and n are as described herein.

In yet another aspect is a method of treating ethanol withdrawal in a subject in need thereof by administering an effective amount of a compound described herein. The method may include co-administering the compounds described herein with another active pharmaceutical agent as described herein. The compound may have formula:

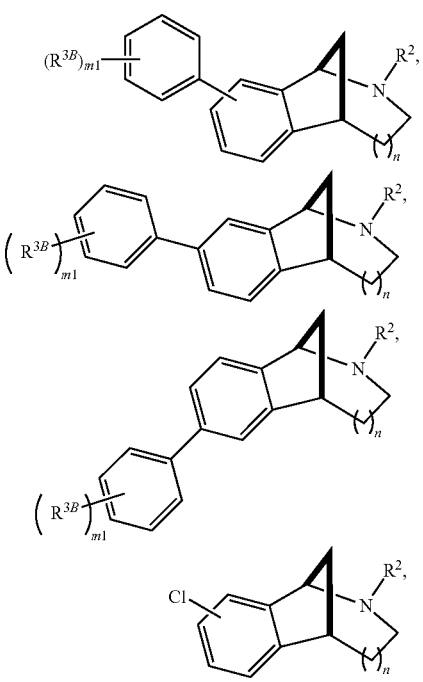

-continued

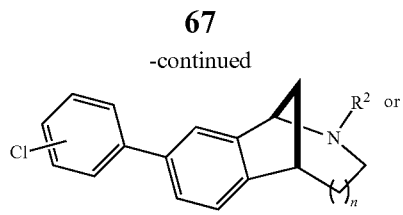

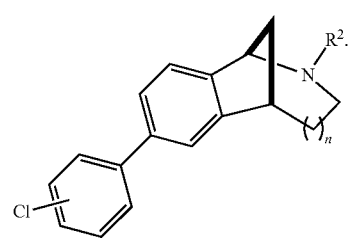

$R^2$, $R^{3B}$, n, and m1 are as described herein. $R^2$ may be hydroxyethyl, hydroxypropyl, or hydroxybutyl.

The compound for treating ethanol withdrawal may have the formula:

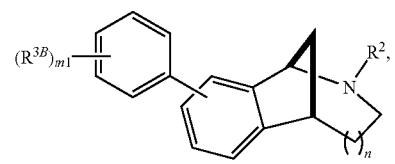

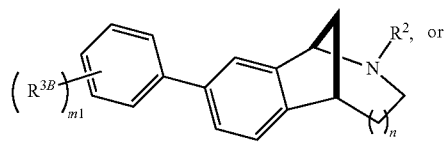

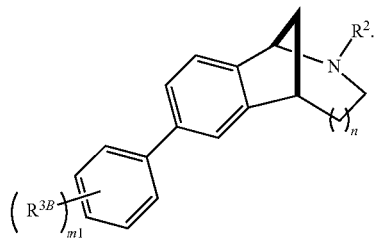

$R^2$, $R^{3B}$, n, and m1 are as described herein. $R^2$ may be hydroxyethyl, hydroxypropyl, or hydroxybutyl.

The compound for treating ethanol withdrawal may have the formula:

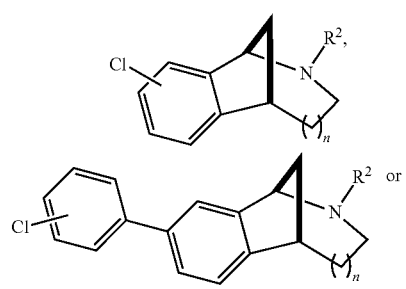

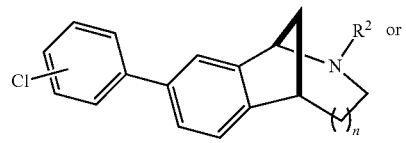

-continued

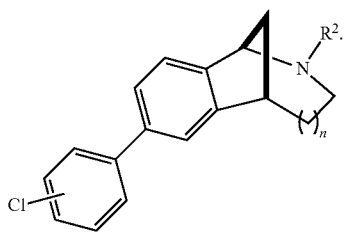

$R^2$ and n are as described herein. $R^2$ may be hydroxyethyl, hydroxypropyl, or hydroxybutyl In still another aspect is a method of treating anxiety or depression in a subject in need thereof by administering an effective amount of a compound described herein. The method may include co-administering the compounds described herein with another active pharmaceutical agent as described herein.

In another aspect is a method of treating neuropathic pain in a subject in need thereof by administering an effective amount of a compound described herein.

IV. Methods of Inhibiting Sigma Receptors

Provided herein are methods of inhibiting or antagonizing a sigma 2 receptor by contacting a sigma 2 receptor with a compound described herein, thereby inhibiting the sigma 2 receptor. The sigma 2 receptor may be PGRMC1. The compound may have the formula:

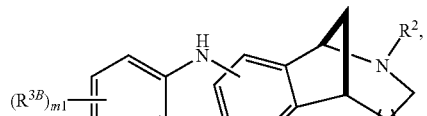

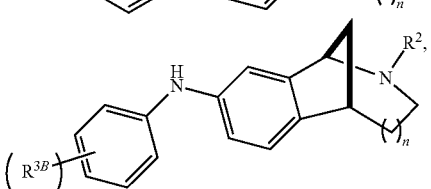

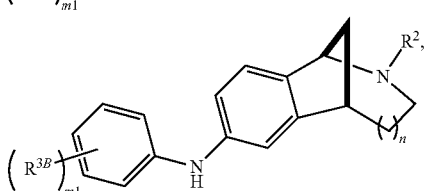

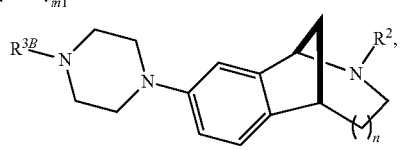

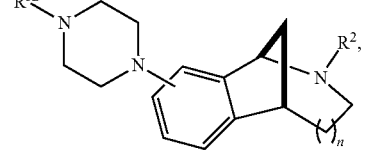

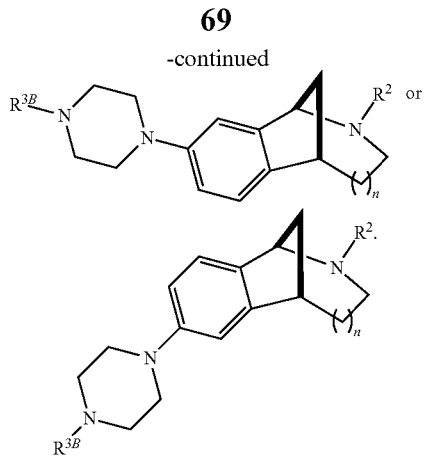

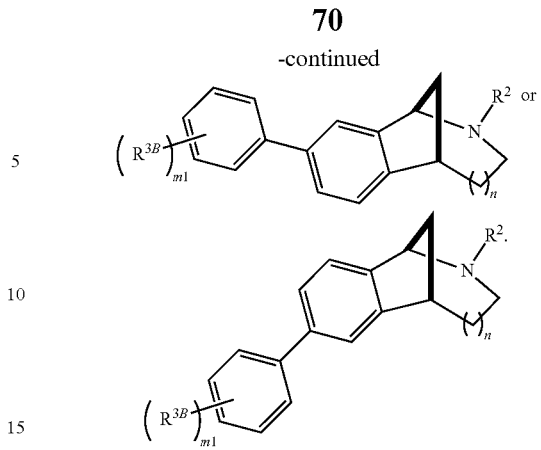

$R^2$, $R^{3B}$, n, and m1 are as described herein.

In another aspect is a method of inhibiting a sigma 1 receptor by contacting a sigma 1 receptor with a compound described herein. The compound may have the structure:

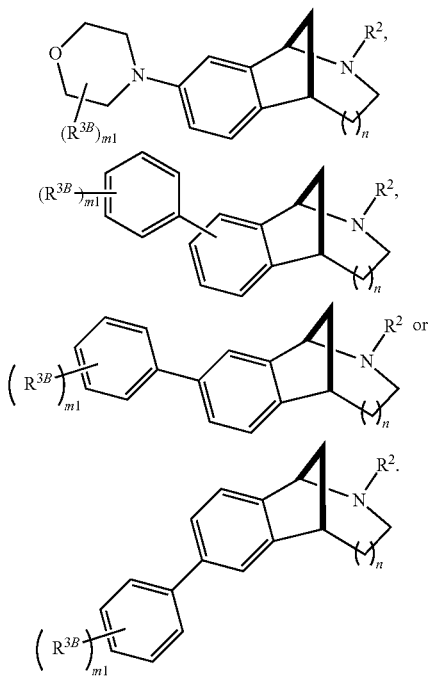

$R^2$, $R^{3B}$, n, and m1 are as described herein.

V. Methods of Activating Sigma Receptors

Provided herein are methods of activating or agonizing a sigma 2 receptor by contacting a sigma 2 receptor with a compound described herein, thereby activating the sigma 2 receptor. The sigma 2 receptor may be PGRMC1. The compound may have the formula:

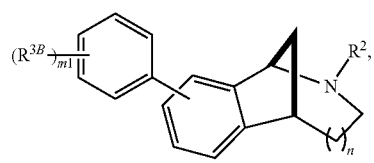

$R^2$, $R^{3B}$, n, and m1 are as described herein.

In another aspect is a method of activating a sigma 1 receptor by contacting a sigma 1 receptor with a compound described herein, thereby activating the sigma 1 receptor. The compound may have the structure:

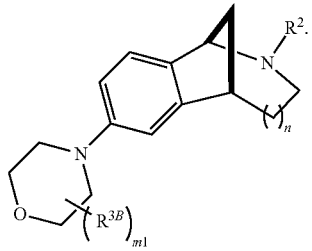

$R^2$, $R^{3B}$, n, and m1 are as described herein.

VI. Other Aspects

Provided herein, in another aspect, are compositions and methods of synthesizing the compositions. The following definitions and embodiments apply to only to the compounds of formula (pI), this section (i.e. section VI) and embodiments p1 to p8 listed below This section describes novel compositions, process, and methods related to the treatments of cancer, neurodegenerative diseases and neurological disorders, including anxiety, depression, neuropathic pain, and substance abuse. More specifically, this section provides novel compounds as derivatives of norbenzomorphan and benzazocine that possess high affinity for sigma receptors and high selectivity for sigma 1 and/or sigma 2 receptors relative to other receptors. This section also provides novel and improved syntheses to prepare the novel derivatives of norbenzomorphan and benzazocine. The compounds of this section have shown biological activities against several types of cancer, AD, and substance abuse In one aspect of this section, the invention is directed to a composition comprising a compound of Formula (pI):

(pI)

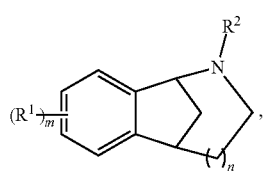

Each R¹ is independently halogen, aryl with optional substitutions, alkyl with optional substitutions, hydroxyl or alkoxy, heterocyclic group with optional substitutions, heteroaryl with optional substitutions or $N(R^3)_2$. $R^2$ is -alkylene-$R^4$,

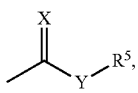

aryl with optional substitutions, heterocyclic group with optional substitutions, heteroaryl group with optional substitutions, or $SO_2R^6$. Each $R^3$ is independently H, alkyl, or together with the adjacent N form a heterocyclic ring, with optional substitutions. $R^4$ is CN, $CO_2R^6$ or aryl with optional substitutions. $R^5$ is H, alkyl, cyclic alkyl, -alkylene-alkyoxyl, adamantyl, allyl, aryl with optional substitutions, -alkylene-aryl with optional substitutions, or heteroaryl with optional substitutions;

each $R^6$ is independently H, alkyl, allyl, aryl with optional substitutions, -alkylene-aryl with optional substitutions, or heteroaryl with optional substitutions. X is O or S. Y is O, NH, or a bond. m is 1, 2, 3, or 4. n is 1 or 2. with a proviso that the compound of Formula (pI) is not a compound selected from the group consisting of:

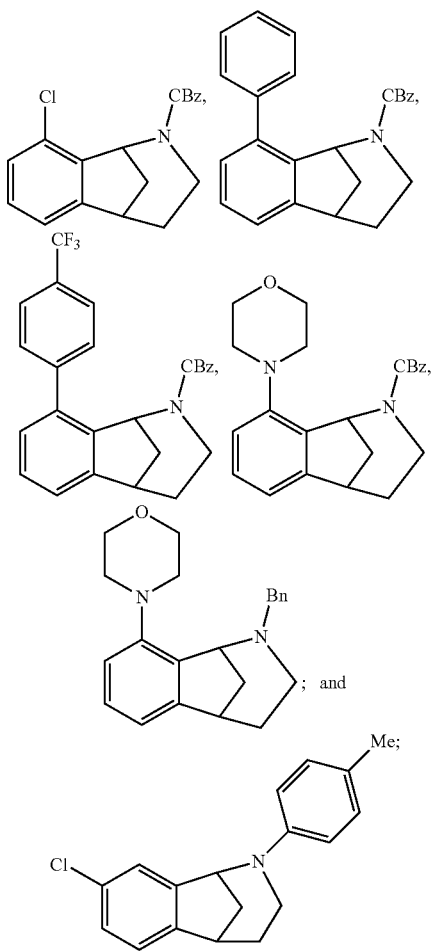

or a pharmaceutically acceptable salt thereof.

In another embodiment of this section, n is 1. In another embodiment of this section, n is 2. In another embodiment of this section, $R^3$ together with the adjacent N form a heterocyclic ring, with optional substitutions. In another embodiment of this section, $R^3$ together with the adjacent N form a piperazine ring with optional substitutions, a morpholine ring with optional substitutions, a pyrrolidine ring with optional substitutions, or a piperidine ring with optional substitutions.

In another embodiment of this section, the compound of Formula (pI) is selected from the group consisting of:

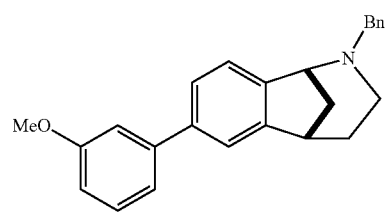

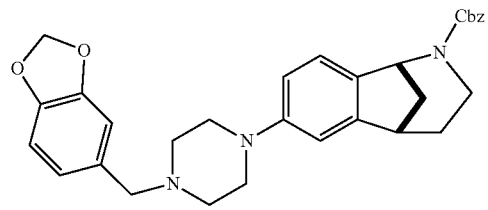

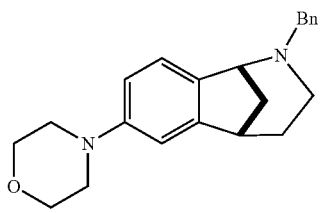

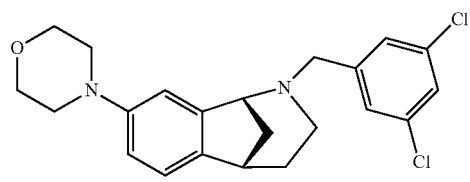

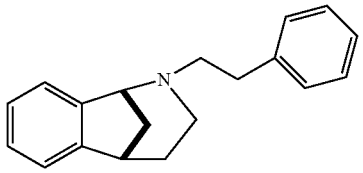

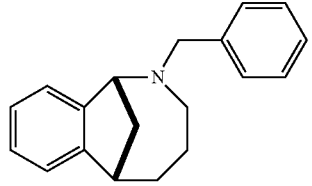

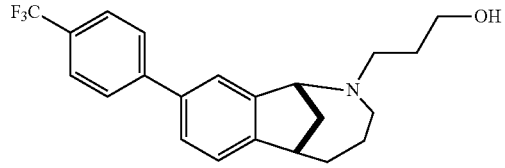

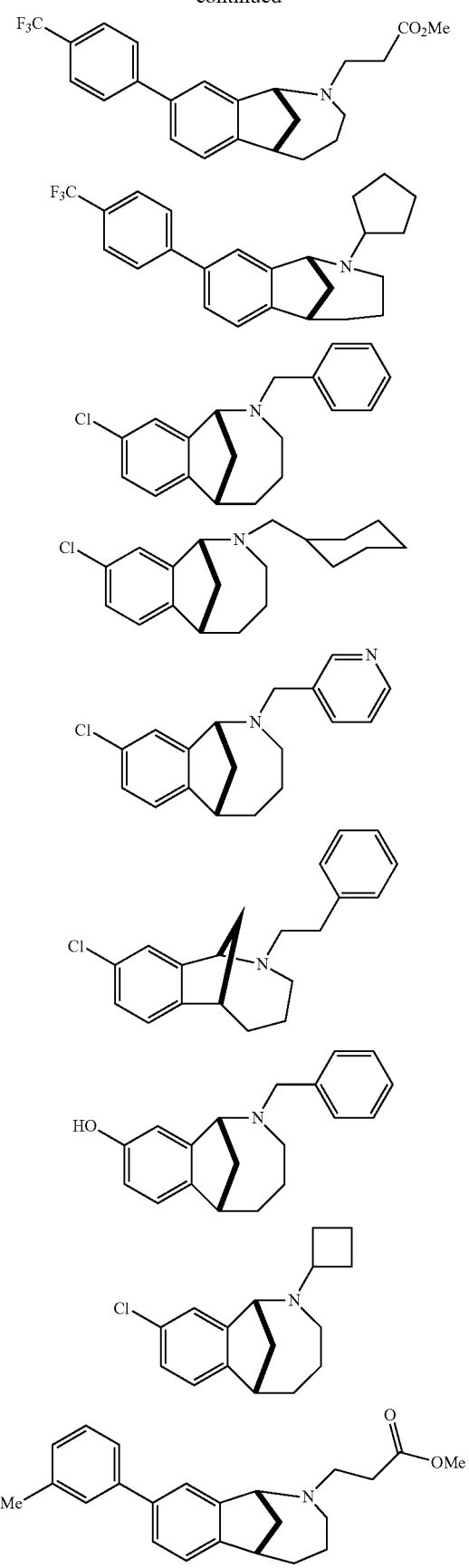

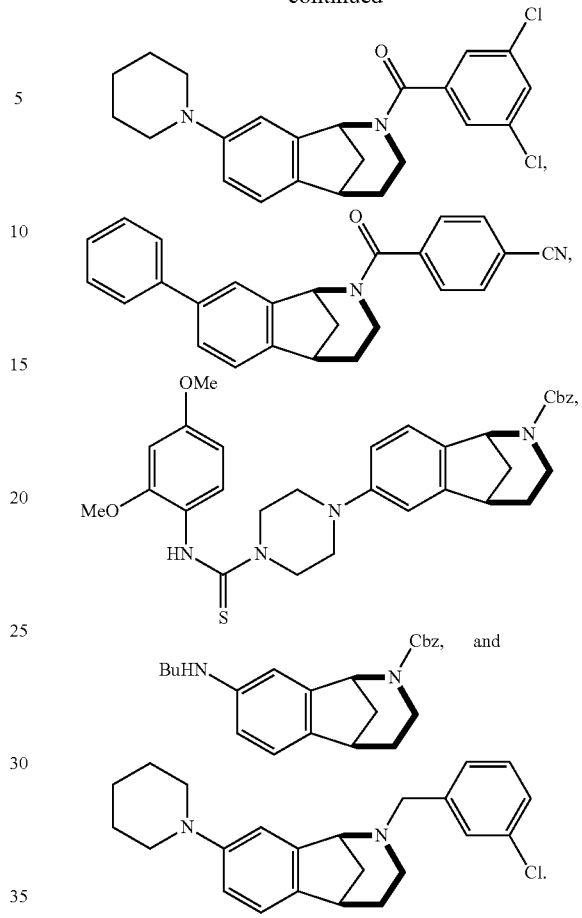

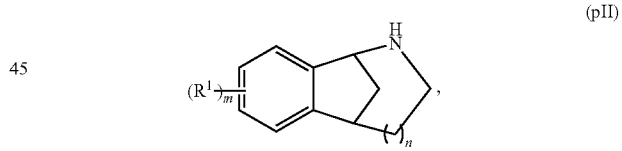

In another aspect of this section is a process comprising the step of reductively aminating a compound of Formula (pII):

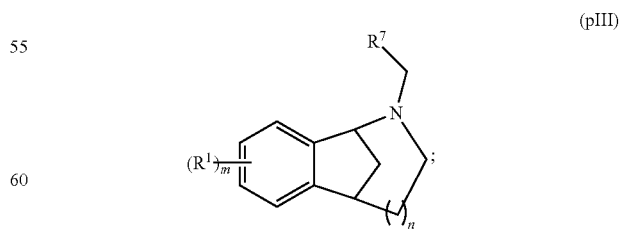

with a suitable aldehyde and a reducing agent to form a compound of Formula (pIII):

(pIII)

wherein each $R^1$ is independently halogen, aryl with optional substitutions, alkyl with optional substitutions, heterocyclic group with optional substitutions, heteroaryl with optional substitutions or $N(R^3)_2$. Each $R^3$ is independently H, alkyl, or together with the adjacent N form a heterocyclic ring, with optional substitutions. R⁷ is alkyl, aryl with optional substitutions, heterocyclic group with optional substitutions, or heteroaryl group with optional substitutions. m is 1, 2, 3, or 4. n is 1 or 2.

Examples of suitable reductive amination agents include but not limited to NaBH(OAc)₃ with aldehyde, preferably NaBH(OAc)₃ but also with NaBH₃CN, with aldehyde. Examples of aldehydes include but not limited to paraformaldehyde, acetaldehyde, benzaldehyde, para-chlorobenzaldehyde, para-anisaldehyde and pyridine-4-carboxaldehyde.

In another aspect of this section is a process comprising the step of acylating a compound of Formula (pII):

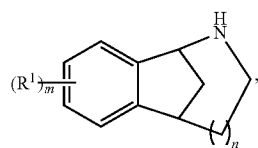

with an acylating agent, under a suitable acylating condition to form a compound of Formula (pIV):

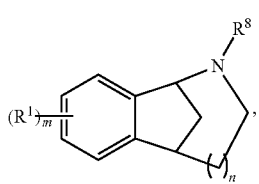

wherein each R¹ is independently halogen, aryl with optional substitutions, alkyl with optional substitutions, heterocyclic group with optional substitutions, heteroaryl with optional substitutions or N(R³)₂. Each R³ is independently H, alkyl, or together with the adjacent N form a heterocyclic ring, with optional substitutions. R⁸ is -alkylene-R⁴,

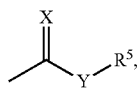

or SO₂R⁶. R⁴ is CN, CO₂R⁶ or aryl with optional substitutions. R⁵ is H, alkyl, cyclic alkyl, -alkylene-alkyoxyl, adamantyl, allyl, aryl with optional substitutions, -alkylene-aryl with optional substitutions, or heteroaryl with optional substitutions. Each R⁶ is independently H, alkyl, alkyloxy, allyl, aryl with optional substitutions, -alkylene-aryl with optional substitutions, or heteroaryl with optional substitutions. X is O or S. Y is O, NH, or CH₂. m is 1, 2, 3, or 4. n is 1 or 2.

Examples of suitable acylating conditions include, but are not limited to, basic conditions, e.g., in the presence of an organic base and in a non-nucleophilic organic solvent that be either polar or nonpolar. Examples of the organic base include, but are not limited to, TEA, DIPEA, pyridine, and DMAP, preferably TEA. Examples of acylating agents include, but are not limited to, acetyl chloride, benzoyl chloride, substituted benzoyl chlorides, nicotinoyl chloride, pivolyl chloride, and methyl chloroformate, benzyl chloroformate, and allyl chloroformate. Examples of sulfonylating agents include, but are not limited to, methanesulfonyl chloride, alkanesulfonyl chlorides, alkoxyalkylsulfonyl chlorides, arylsulfonyl chlorides, and heteroaryl sulfonyl chlorides.

Another aspect of this section is a composition comprising a compound of Formula (pII):

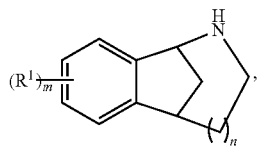

wherein each R¹ is independently halogen, aryl with optional substitutions, alkyl with optional substitutions, heterocyclic group with optional substitutions, heteroaryl with optional substitutions or N(R³)₂. Each R³ is independently H, alkyl, or together with the adjacent N form a heterocyclic ring, with optional substitutions. m is 1, 2, 3, or 4. n is 1 or 2. with a proviso that the compound of formula (II) is not

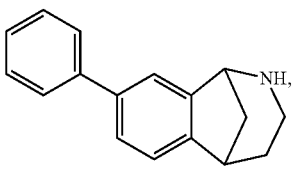 [SMILES: c1ccc(-c2ccc3c(c2)C2CC3CCN2)cc1]

or a pharmaceutically acceptable salt thereof.

In one embodiment of this section, the compound of Formula (II) is

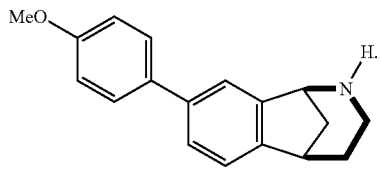

For purposes of this section, the indefinite articles "a" and "an" preceding an element or component of the invention are intended to be nonrestrictive regarding the number of instances (i.e. occurrences) of the element or component. Therefore, "a" or "an" should be read to include one or at least one, and the singular word form of the element or component also includes the plural unless the number is obviously meant to be singular.

For purposes of this section, the term "alkyl" means a saturated aliphatic hydrocarbon group which may be straight or branched having 1 to 20 carbon atoms in the chain. Preferred alkyl groups have 1 to 6 carbon atoms in the chain. "Branched" means that one or more lower alkyl groups, such as methyl, ethyl or propyl, are attached to a linear alkyl chain. Lower alkyl, means 1 to 4 carbon atoms in the chain which may be straight or branched. The alkyl may be substituted with one or more alkyl group substituents, which may be the same or different, and include for instance halo, cycloalkyl, hydroxy, alkoxy, amino, acylamino, aroylamino, carboxy.

For purposes of this section, the term "alkylene" means a straight chain or branched alkanediyl with up to about 20 carbons. Examples of "alkylene" include CH$_2$, CH$_2$CH$_2$, CH(CH$_3$), CH$_2$CH$_2$CH$_2$, CH$_2$CH(CH$_3$), and the different butylene isomers.

For purposes of this section, the term "aryl" means an aromatic monocyclic or multicyclic ring system radical of up to about 20 carbon atoms. Preferably aryl is phenyl, naphthyl or anthracenyl. The aryl moiety is optionally substituted with one or more groups, e.g., alkyl, alkenyl, hydroxyl, alkoxy, or halo.

For purposes of this section, the term "heteroaryl" means a monocyclic or polycyclic aromatic ring comprising carbon atoms, hydrogen atoms, and one or more heteroatoms, preferably, 1 to 3 heteroatoms, independently selected from nitrogen, oxygen, and sulfur. As is well known to those skilled in the art, heteroaryl rings have less aromatic character than their all-carbon counter parts. Thus, for the purposes of the disclosure, a heteroaryl group need only have some degree of aromatic character. Illustrative examples of heteroaryl groups include, but are not limited to, pyridinyl, pyridazinyl, pyrimidyl, pyrazyl, triazinyl, pyrrolyl, pyrazolyl, imidazolyl, (1,2,3,)- and (1,2,4)-triazolyl, pyrazinyl, pyrimidinyl, tetrazolyl, furyl, thienyl, isoxazolyl, thiazolyl, isoxazolyl, and oxazolyl. A heteroaryl group can be unsubstituted or substituted with one or two suitable substituents.

For purpose of this section, the term "heterocyclic ring" or "heterocycle" means a ring wherein at least one of the atoms forming the ring backbone is other than carbon. Unless otherwise indicated, a heterocyclic ring can be a saturated, partially unsaturated, or full unsaturated ring. "Saturated heterocyclic ring" refers to a heterocyclic ring containing only single bonds between ring members. "Partially saturated heterocyclic ring" refers a heterocyclic ring containing at least one double bond but which is not aromatic. Examples of heterocycles include from 3-membered rings to 8-membered rings, with optional additional heteroatom substitutions on the ring. Examples of heterocyclic rings include, but are not limited to, a piperazine ring, a morpholine ring, a pyrrolidine ring, and a piperidine ring.

Where the processes for the preparation of the compounds according to this section give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques. The compounds may also be resolved by formation of diastereomeric esters or amides, followed by chromatographic separation and removal of the chiral auxiliary. Alternatively, the compounds may be resolved using a chiral HPLC column.

VII. Embodiments

Embodiment 1

A compound having the formula:

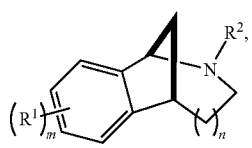

(I)

$R^1$ is hydrogen, halogen, —N$_3$, —CF$_3$, —CCl$_3$, —CBr$_3$, —CI$_3$, —CN, —C(O)R$^3$, —OR$^3$, —NR$^3$R$^{3A}$, —C(O)OR$^3$, —C(O)NR$^3$R$^{3A}$, —NO$_2$, —SR$^3$, —S(O)$_{n1}$R$^3$, —S(O)$_{n1}$OR$^3$, —S(O)$_{n1}$NR$^3$R$^{3A}$, —NHNR$^3$R$^{3A}$, —ONR$^3$R$^3$, —NHC(O)NHNR$^3$R$^{3A}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^2$ is hydrogen, halogen, —N$_3$, —CF$_3$, —CCl$_3$, —CBr$_3$, —CI$_3$, —CN, —C(O)R$^4$, —OR$^4$, —NR$^4$R$^{4A}$, —C(O)OR$^4$, —C(O)NR$^4$R$^{4A}$, —NO$_2$, —SR$^4$, —S(O)$_{n2}$R$^4$, —S(O)$_{n2}$OR$^4$, —S(O)$_{n2}$NR$^4$R$^{4A}$, —NHNR$^4$R$^{4A}$, —ONR$^4$R$^{4A}$, —NHC(O)NHNR$^4$R$^{4A}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; n1 and n2 are independently 1 or 2; m is 1, 2, 3 or 4; n is 1 or 2; and $R^3$, $R^{3A}$, $R^4$, $R^{4A}$ are independently hydrogen, oxo, halogen, —CF$_3$, —CN, —OH, —NH$_2$, —COOH, —CONH$_2$, —NO$_2$, —SH, —S(O)$_2$Cl, —S(O)$_3$H, —S(O)$_4$H, —S(O)$_2$NH$_2$, —NHNH$_2$, —ONH$_2$, —NHC(O)NHNH$_2$, —NHC(O) NH$_2$, —NHS(O)$_2$H, —NHC(O)H, —NHC(O)—OH, —NHOH, —OCF$_3$, —OCHF$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment 2

The compound of embodiment 1, wherein the compound is not

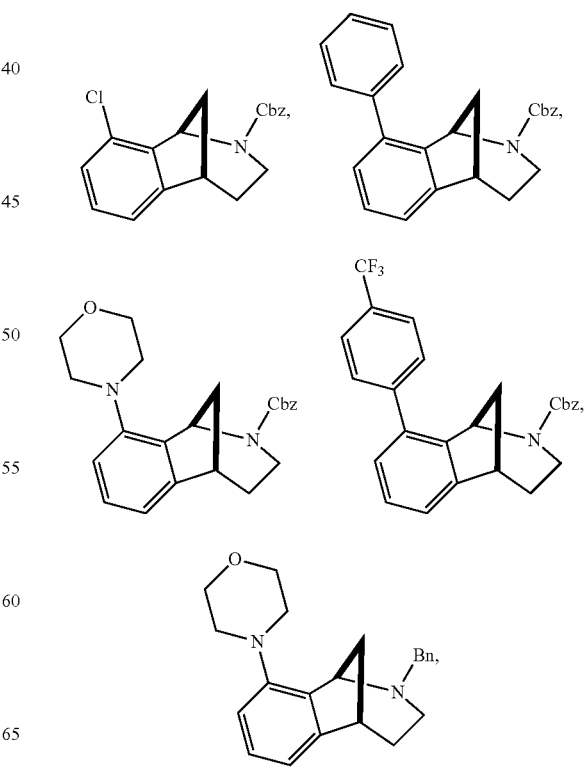

-continued

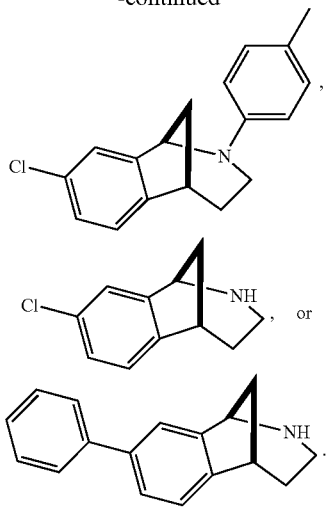

Embodiment 3

The compound of embodiment 1 or 2, having the structure:

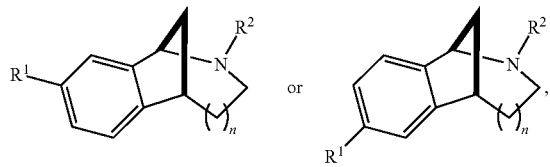

wherein $R^1$ is halogen, —$N_3$, —$CF_3$, —$CCl_3$, —$CBr_3$, —$CI_3$, —CN, —C(O)$R^3$, —$OR^3$, —$NR^3R^{3A}$, —C(O)$OR^3$, —C(O)$NR^3R^{3A}$, —$NO_2$, —SR, —S(O)$_{n1}R^3$, —S(O)$_{n1}OR^3$, —S(O)$_{n1}NR^3R^{3A}$, —$NHNR^3R^{3A}$, —$ONR^3R^{3A}$ NHC(O) $NHNR^3R^{3A}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl

Embodiment 4

The compound of any one of embodiments 1 to 3, wherein $R^1$ is halogen.

Embodiment 5

The compound of any one of embodiments 1 to 4, wherein $R^2$ is halogen, —CN, —C(O)$R^4$, —$OR^4$, —$NR^4R^{4A}$, —C(O)$OR^4$, —C(O)$NR^4R^{4A}$, —S(O)$_{n2}R^4$, —S(O)$_{n2}OR^4$, —S(O)$_{n2}NR^4R^{4A}$ $ONR^4R^{4A}$, —NHC(O)$NHNR^4R^{4A}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment 6

The compound of any one of embodiments 1 to 5, wherein $R^1$ is halogen, —$OR^3$, —$NR^3R^{3A}$, —C(O)$OR^3$, substituted or unsubstituted alkyl, substituted or unsubstituted cycloalkyl, substituted or unsubstituted heterocycloalkyl, substituted or unsubstituted aryl, substituted or unsubstituted heteroaryl.

Embodiment 7

The compound of any one of embodiments 1 to 6, wherein $R^1$ is halogen, —$OR^3$, —$NR^3R^{3A}$, substituted or unsubstituted alkyl, substituted or unsubstituted heterocycloalkyl, substituted or unsubstituted aryl, substituted or unsubstituted heteroaryl.

Embodiment 8

The compound of any one of embodiments 1 to 6, wherein $R^1$ is Cl, F, Br, —OH, —$OR^3$, —$NR^3R^{3A}$, $R^3$-substituted or unsubstituted $C_1$-$C_{10}$ alkyl, $R^3$-substituted or unsubstituted heterocycloalkyl, $R^3$-substituted or unsubstituted aryl, $R^3$-substituted or unsubstituted heteroaryl, $R^{3A}$ is hydrogen; $R^3$ is —$CF_3$, —CN, —OH, —$NH_2$, —$CONH_2$, —S(O)$_3$H, —S(O)$_2NH_2$, —NHC(O) $NH_2$, —NHC(O)H, —$OCHF_2$, $R^{3B}$-substituted or unsubstituted alkyl, $R^{3B}$-substituted or unsubstituted heteroalkyl, $R^{3B}$-substituted or unsubstituted cycloalkyl, $R^{3B}$-substituted or unsubstituted heterocycloalkyl, $R^{3B}$-substituted or unsubstituted aryl, or $R^{3B}$-substituted or unsubstituted heteroaryl; and $R^{3B}$ is —$CF_3$, —CN, —OH, —$NH_2$, —$CONH_2$, —S(O)$_3$H, —S(O)$_2NH_2$, —NHC(O) $NH_2$, —NHC(O)H, —$OCHF_2$, unsubstituted alkyl, unsubstituted heteroalkyl, unsubstituted cycloalkyl, unsubstituted heterocycloalkyl, unsubstituted aryl or unsubstituted heteroaryl.

Embodiment 9

The compound of any one of embodiments 1 to 7, having the formula:

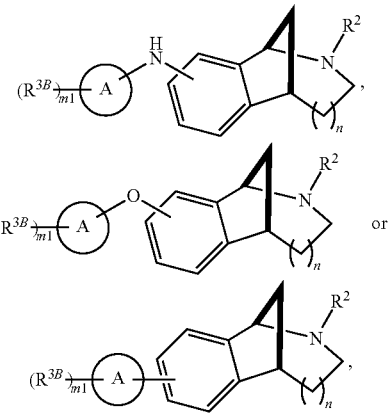

wherein $R^{3B}$ is —$CF_3$, —CN, —OH, —$NH_2$, —$CONH_2$, —S(O)$_3$H, —S(O)$_2NH_2$, —NHC(O) $NH_2$, —NHC(O)H, —$OCHF_2$, unsubstituted alkyl, unsubstituted heteroalkyl, unsubstituted cycloalkyl, unsubstituted heterocycloalkyl, unsubstituted aryl or unsubstituted heteroaryl; ring A is aryl, heteroaryl, cycloalkyl or heterocycloalkyl; and m1 is 0, 1, 2, 3, or 4.

Embodiment 10

The compound embodiment 9, wherein ring A is aryl or heterocycloalkyl.

Embodiment 11

The compound of any one of embodiments 1 to 9, having the formula

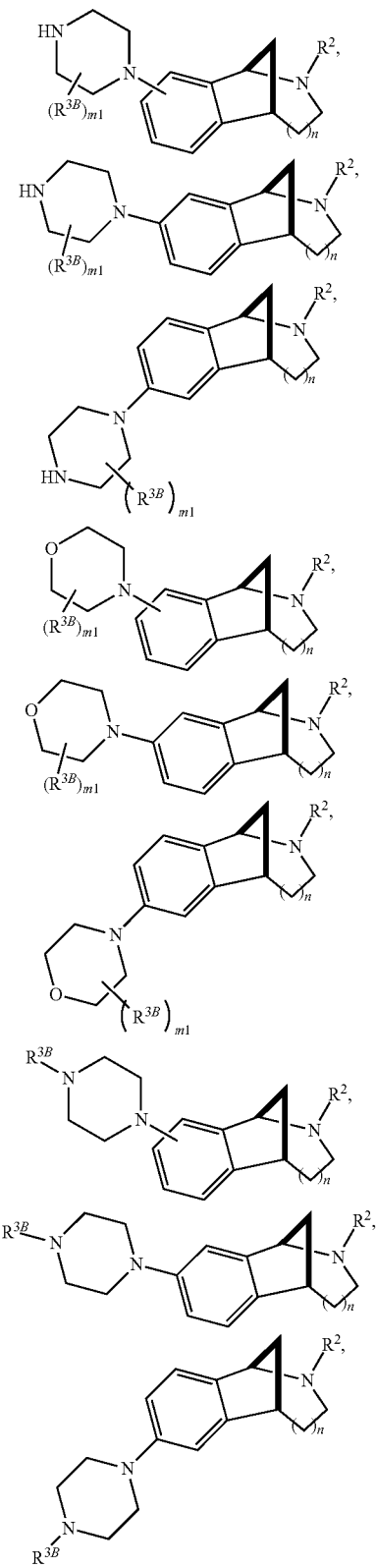

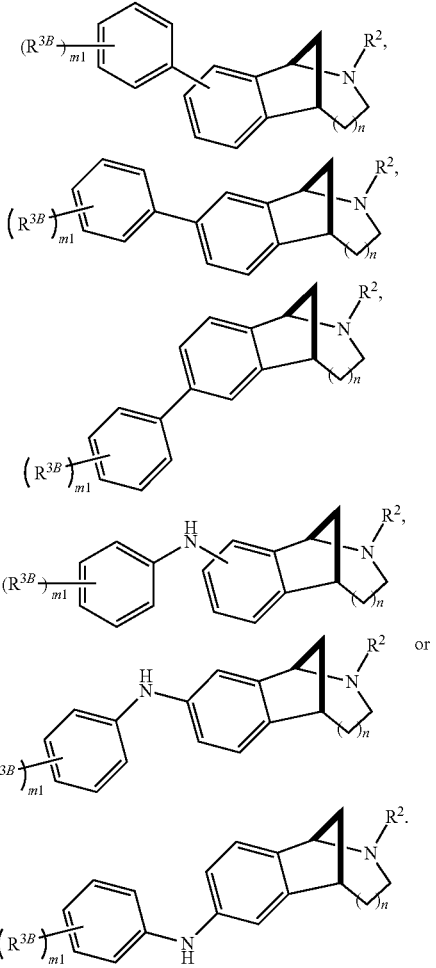

Embodiment 12

The compound of any one of embodiments 9 to 11, wherein $R^{3B}$ is halogen, —$CF_3$, —CN, —OH, unsubstituted alkyl or unsubstituted heteroalkyl.

Embodiment 13

The compound of any one of embodiments 9 to 12, wherein $R^{3B}$ is halogen, —$CF_3$, —OH, —$OCH_3$ or unsubstituted $C_1$-$C_5$ alkyl.

Embodiment 14

The compound of any one of embodiments 1 to 13, wherein m1 is 0 or 1.

Embodiment 15

The compound of embodiment 14, wherein m1 is 0.

Embodiment 16

The compound of embodiment 14, wherein m1 is 1.

Embodiment 17

The compound of any one of embodiments 1 to 16, wherein n is 1.

Embodiment 18

The compound of any one of embodiments 1 to 17, wherein $R^2$ is —$OR^4$, —$NR^4R^{4A}$, —$C(O)OR^4$, substituted or unsubstituted alkyl, substituted or unsubstituted cycloalkyl, substituted or unsubstituted heterocycloalkyl, substituted or unsubstituted aryl, substituted or unsubstituted heteroaryl.

Embodiment 19

The compound of any one of embodiments 1 to 17, wherein $R^2$ is —$OR^4$, —$NR^4R^{4A}$, —$C(O)OR^4$, substituted or unsubstituted alkyl, substituted or unsubstituted heterocycloalkyl, substituted or unsubstituted aryl, substituted or unsubstituted heteroaryl.

Embodiment 20

The compound of any one of embodiments 1 to 17, wherein $R^2$ is —$C(O)OR^4$, wherein $R^4$ is $R^{4B}$-substituted or unsubstituted aryl, wherein $R^{4B}$ is —$CF_3$, —CN, —OH, unsubstituted alkyl or unsubstituted heteroalkyl.

Embodiment 21

The compound of embodiment 20, wherein $R^4$ is unsubstituted aryl.

Embodiment 22

The compound of any one of embodiments 1 to 17, wherein $R^2$ is $R^{4B}$-substituted or unsubstituted alkyl, wherein $R^{4B}$ is $R^{4C}$-substituted or unsubstituted aryl, wherein $R^{4C}$ is halogen, —$CF_3$, —CN, —OH, unsubstituted alkyl or unsubstituted heteroalkyl.

Embodiment 23

The compound of embodiment 22, wherein $R^{4C}$ is unsubstituted aryl.

Embodiment 24

The compound of any one of embodiments 1 to 17, wherein $R^2$ is unsubstituted $C_1$-$C_5$ alkyl.

Embodiment 25

The compound of embodiment 1 having the formula:

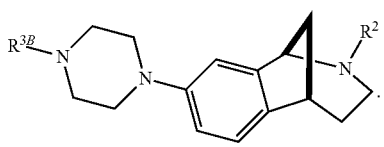

Embodiment 26

The compound of embodiment 25, wherein $R^{3B}$ is substituted or unsubstituted alkyl.

Embodiment 27

The compound of embodiment 25, wherein $R^{3B}$ is substituted or unsubstituted $C_1$-$C_{10}$ alkyl.

Embodiment 28

The compound of embodiment 25, wherein $R^{3B}$ is unsubstituted $C_1$-$C_{10}$ alkyl.

Embodiment 29

The compound of embodiment 25, wherein $R^{3B}$ is methyl.

Embodiment 30

The compound of any one of embodiments 25 to 29, wherein $R^2$ is —$C(O)OR^4$, wherein $R^4$ is $R^{4B}$-substituted or unsubstituted aryl, wherein $R^{4B}$ is halogen, —$CF_3$, —CN, —OH, unsubstituted alkyl or unsubstituted heteroalkyl.

Embodiment 31

The compound of embodiment 30, wherein $R^{4B}$ is —$CF_3$, —CN, —OH, unsubstituted alkyl or unsubstituted heteroalkyl.

Embodiment 32

The compound of embodiment 30, wherein $R^4$ is $R^{4B}$-substituted or unsubstituted phenyl.

Embodiment 33

The compound of embodiment 32, wherein $R^4$ is unsubstituted phenyl.

Embodiment 34

A pharmaceutical composition comprising a compound of any one of embodiments 1 to 33 and a pharmaceutically acceptable excipient or pharmaceutically acceptable salt.

Embodiment 35

A method of treating cancer in a subject in need thereof, the method comprising administering an effective amount of the compound of any one of embodiments 1 to 33.

Embodiment 36

A method to treating a neurodegenerative disease in a subject in need thereof, the method comprising administering an effective amount of the compound of any one of embodiments 1 to 33.

Embodiment 37

The method of embodiment 36, wherein the neurodegenerative disease is Alzheimer's disease or Amyotrophic lateral sclerosis.

Embodiment 38

The method of embodiment 36 or 37, wherein the compound has the formula:

85

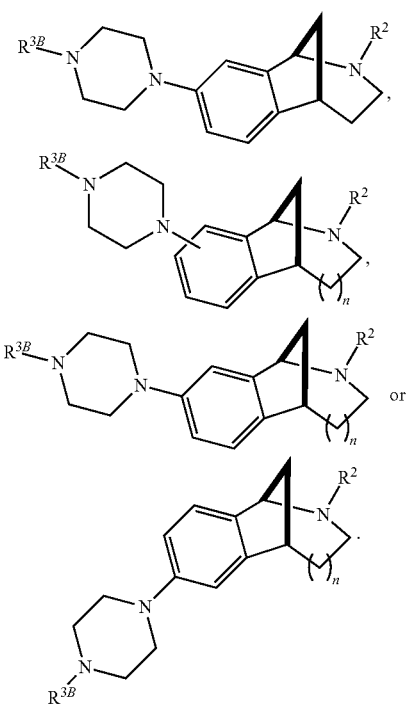

Embodiment 39

A method of treating ethanol withdrawal in a subject in need thereof, the method comprising administering an effective amount of the compound of any one of embodiments 1 to 33.

Embodiment 40

The method of embodiment 39, wherein the compound has the structure

![structures]

Embodiment 41

The method of embodiment 40, wherein $R^2$ is hydroxyethyl, hydroxypropyl, or hydroxybutyl.

86

Embodiment 42

The method of embodiment 39, wherein the compound has the structure

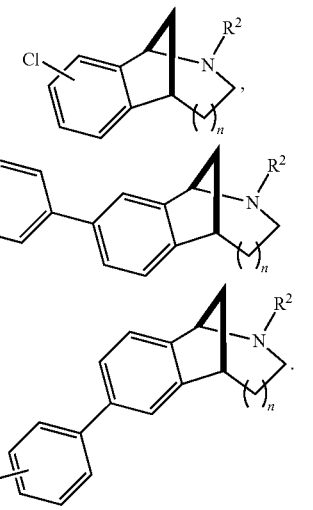

Embodiment 43

The method of embodiment 42, wherein $R^2$ is hydroxyethyl, hydroxypropyl, or hydroxybutyl.

Embodiment 44

A method of treating anxiety or depression in a subject in need thereof, the method comprising administering an effective amount of the compound of any one of embodiments 1 to 33.

Embodiment 45

A method of treating neuropathic pain in a subject in need thereof, the method comprising administering an effective amount of the compound of any one of embodiments 1 to 33.

Embodiment 46

A method of inhibiting/antagonizing a sigma 2 receptor, the method comprising contacting a sigma 2 receptor with the compound of any one of embodiments 1 to 33 thereby inhibiting said sigma 2 receptor.

Embodiment 47

The method of embodiment 46, wherein said compound has the structure

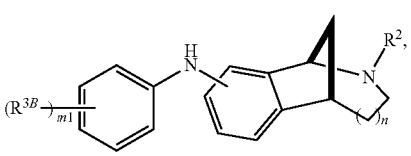

-continued

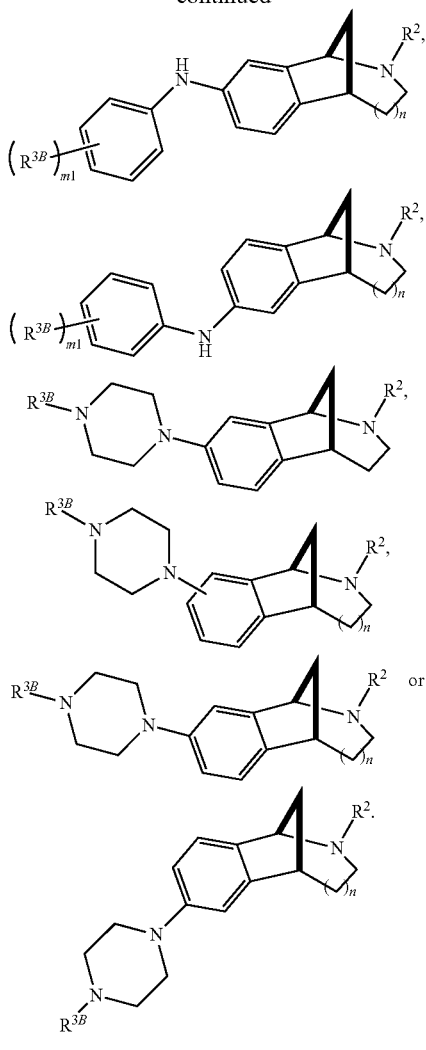

Embodiment 48

A method of activating/agonizing a sigma 2 receptor, the method comprising contacting a sigma 2 receptor with the compound of any one of embodiments 1 to 33 thereby activating said sigma 2 receptor.

Embodiment 49

The method of embodiment 48, wherein said compound has the structure

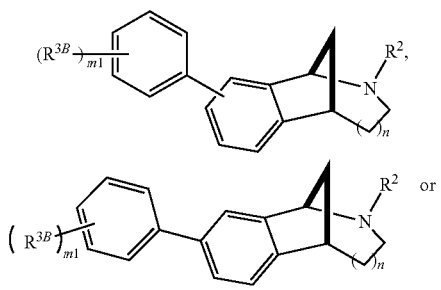

-continued

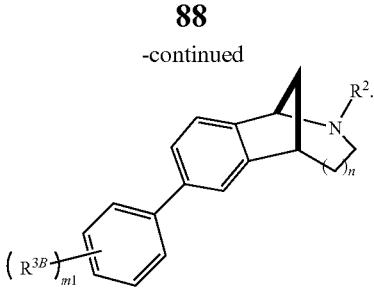

Embodiment 50

A method of inhibiting a sigma 1 receptor, the method comprising contacting a sigma 1 receptor with the compound of any one of embodiments 1 to 33 thereby inhibiting said sigma 1 receptor.

Embodiment 51

The method of embodiment 50, wherein said compound has the structure

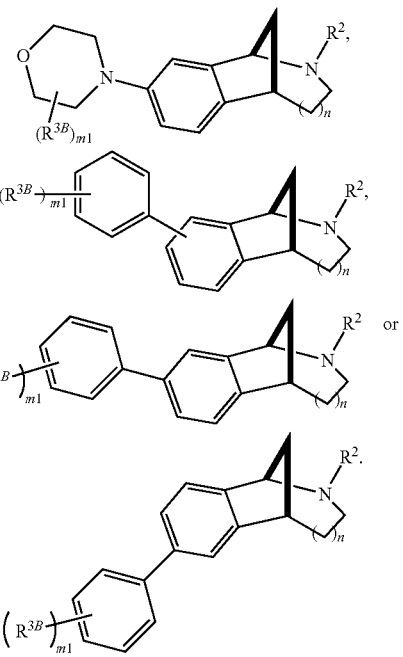

Embodiment 52

A method of activating a sigma 1 receptor, the method comprising contacting a sigma 1 receptor with the compound of any one of embodiments 1 to 33 thereby activating said sigma 1 receptor.

Embodiment 53

The method of embodiment 52, wherein the compound has the structure

89

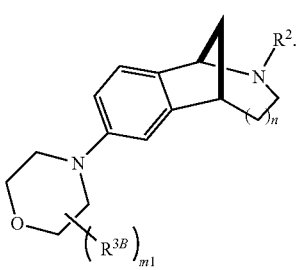

1. Embodiment p1

A composition comprising a compound of formula (pI):

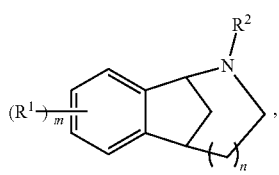
(pI)

wherein each R¹ is independently halogen, aryl with optional substitutions, alkyl with optional substitutions, heterocyclic group with optional substitutions, heteroaryl with optional substitutions or N(R³)₂; R² is -alkylene-R⁴,

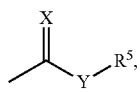

aryl with optional substitutions, heterocyclic group with optional substitutions, heteroaryl group with optional substitutions, or SO₂R⁶; each R³ is independently H, alkyl, or together with the adjacent N form a heterocyclic ring, with optional substitutions; R⁴ is CN, CO₂R⁶ or aryl with optional substitutions; R⁵ is H, alkyl, cyclic alkyl, -alkylene-alkyoxyl, adamantyl, allyl, aryl with optional substitutions, -alkylene-aryl with optional substitutions, or heteroaryl with optional substitutions; each R⁶ is independently H, alkyl, allyl, aryl with optional substitutions, -alkylene-aryl with optional substitutions, or heteroaryl with optional substitutions; X is O or S; Y is O, NH, or a bond; m is 1, 2, 3, or 4; n is 1 or 2; with a proviso that the compound of formula (I) is not a compound selected from the group consisting of:

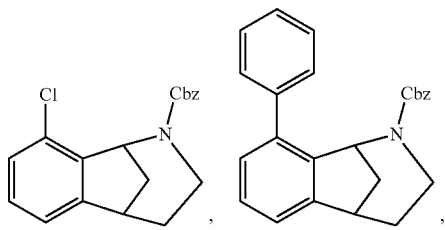

90

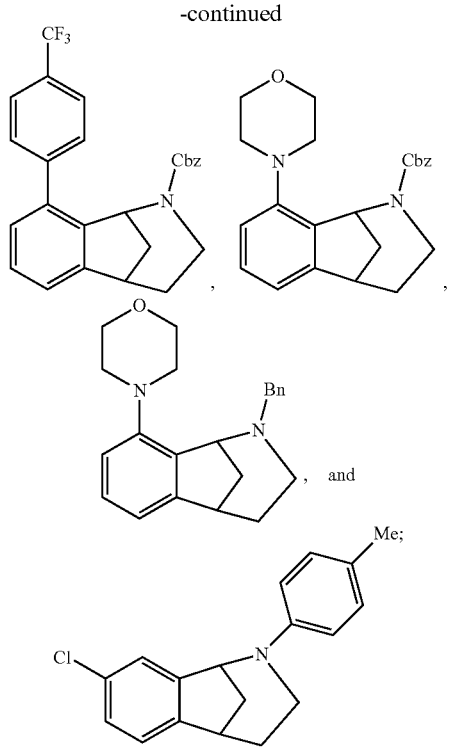

or a pharmaceutically acceptable salt thereof.

Embodiment p2

The composition according to embodiment 1, wherein n is 1.

Embodiment p3

The composition according to embodiment 1, wherein n is 2.

Embodiment p4

The composition according to embodiment 2, wherein the compound of Formula (pI) is selected from the group consisting of:

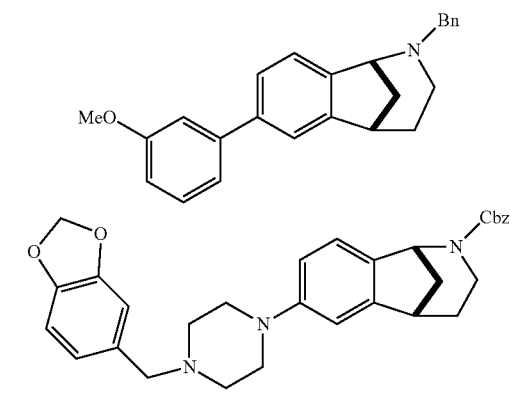

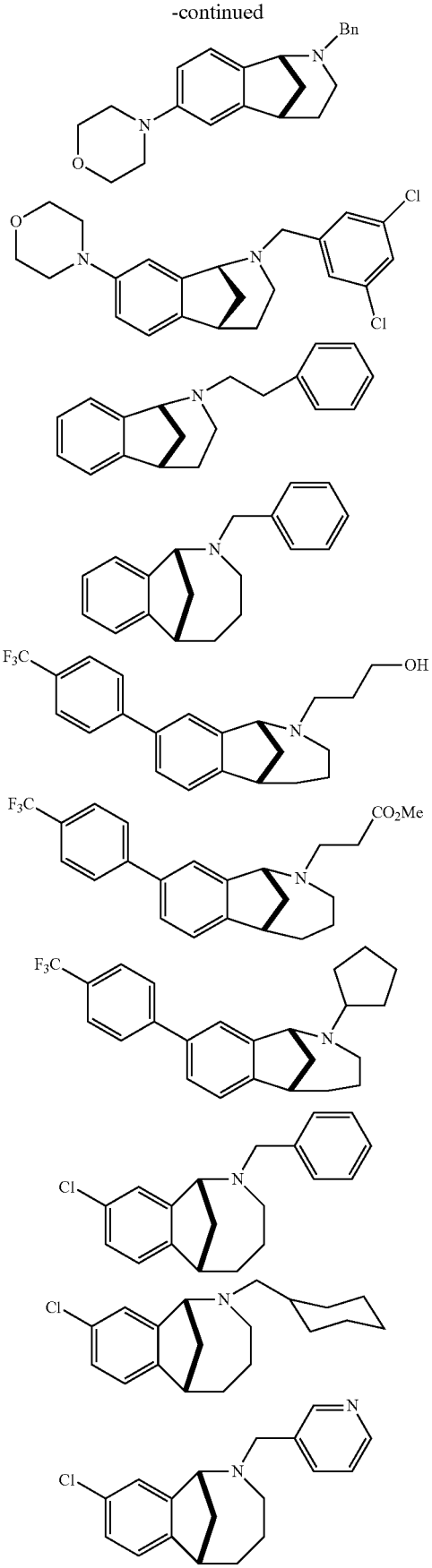
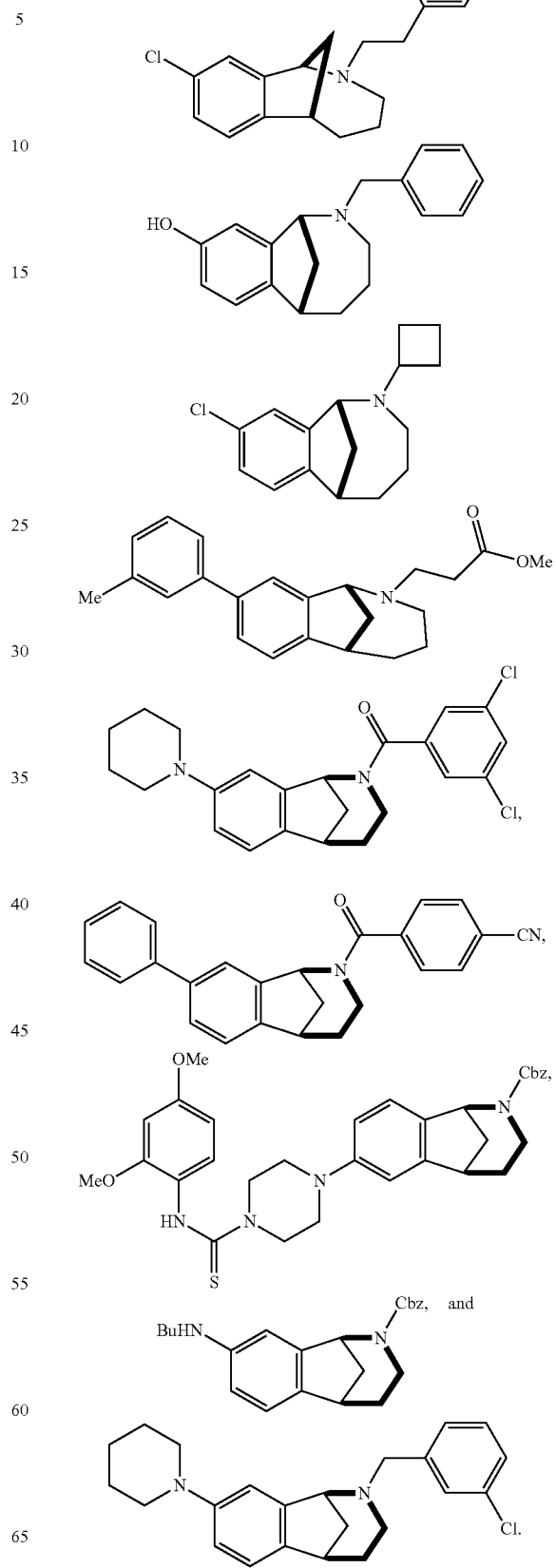

Embodiment p5

A process comprising the step of reductively aminating a compound of Formula (pII):

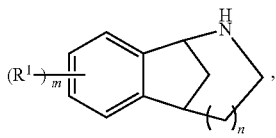
(pII)

with a suitable reductive amination agent to form a compound of Formula (pIII):

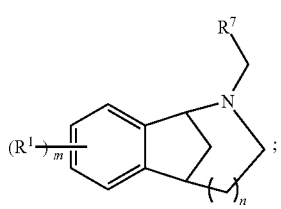
(pIII)

wherein each $R^1$ is independently halogen, aryl with optional substitutions, alkyl with optional substitutions, heterocyclic group with optional substitutions, heteroaryl with optional substitutions or $N(R^3)_2$; each $R^3$ is independently H, alkyl, or together with the adjacent N form a heterocyclic ring, with optional substitutions; $R^7$ is alkyl, aryl with optional substitutions, heterocyclic group with optional substitutions, or heteroaryl group with optional substitutions; m is 1, 2, 3, or 4; and n is 1 or 2.

Embodiment p6

A process comprising the step of acylating a compound of Formula (pII):

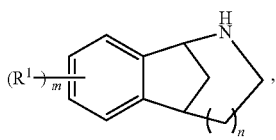
(pII)

with an acylating agent, under a suitable acylating condition to form a compound of Formula (pIV):

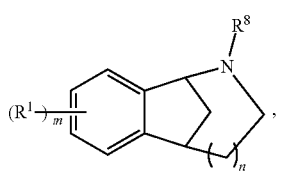
(pIV)

wherein each $R^1$ is independently halogen, aryl with optional substitutions, alkyl with optional substitutions, heterocyclic group with optional substitutions, heteroaryl with optional substitutions or $N(R^3)_2$; each $R^3$ is independently H, alkyl, or together with the adjacent N form a heterocyclic ring, with optional substitutions; $R^8$ is -alkylene-$R^4$,

or $SO_2R^6$;

$R^4$ is CN, $CO_2R^6$ or aryl with optional substitutions; $R^5$ is H, alkyl, cyclic alkyl, -alkylene-alkyoxyl, adamantyl, allyl, aryl with optional substitutions, -alkylene-aryl with optional substitutions, or heteroaryl with optional substitutions; each $R^6$ is independently H, alkyl, allyl, aryl with optional substitutions, -alkylene-aryl with optional substitutions, or heteroaryl with optional substitutions; X is O or S; Y is O, NH, or a bond; m is 1, 2, 3, or 4; and n is 1 or 2.

Embodiment p7

A composition comprising a compound of Formula (pII):

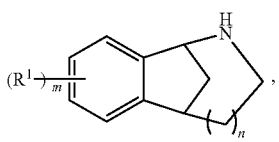
(pII)

wherein each $R^1$ is independently halogen, aryl with optional substitutions, alkyl with optional substitutions, heterocyclic group with optional substitutions, heteroaryl with optional substitutions or $N(R^3)_2$; each $R^3$ is independently H, alkyl, or together with the adjacent N form a heterocyclic ring, with optional substitutions; m is 1, 2, 3, or 4; n is 1 or 2; with a proviso that the compound of Formula (pII) is not

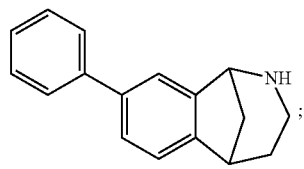 [SMILES: c1ccc(-c2ccc3c(c2)C2CC3CCN2)cc1]

or a pharmaceutically acceptable salt thereof.

Embodiment p8

The composition according to embodiment 7, wherein the compound of formula (pII) is

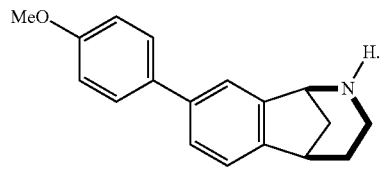

VIII. Examples

1.

We determined the blood brain barrier (BBB) permeability and pharmacokinetic (PK) profile of JJS-1-166 (phase I), and subsequently investigated the efficacy of JJS-1-166 in an Alzheimer's disease (AD) mouse model.

Alzheimer's disease (AD) is neurodegenerative disease characterized by senile plaques containing β-amyloid protein (Aβ) and neurofibrillary tangles[1]. In 2012, an estimated 5.4 million Americans were living with AD. This prevalence is expected to increase to 6.7 million by 2025 and triple to 11-16 million by 2050 if no medical breakthroughs are found (Alzheimer's Association 2012 Report). With such alarming projected prevalence in the population, high medical costs, and low quality of life associated with AD[2], it is increasingly imperative that new therapies are identified to prevent and/or rescue the cognitive symptoms of AD.

We found that JJS-1-166 possesses acceptable blood-brain-barrier (BBB) permeability and pharmacokinetic properties. 3) Since adequate brain exposure and acceptable PK characteristics were observed, including brain clearance after 24 and 72 hours, JJS-1-166 is undergoing efficacy assessment in a mouse model of AD that include a range of behavioral tests, followed by tissue processing for analysis of biomarkers.

TABLE 7

Drug Concentration in the Brain

| ID | Drug concentration (ng/g) | Time point (h) |
|---|---|---|
| SBFNL-14051-ID4 | 1570.0 | 3 |
| SBFNL-14051-ID5 | 1100.0 | 3 |
| SBFNL-14051-ID6 | 1840.0 | 3 |
| SBFNL-14063-BC-ID1 | 1.63 | 24 |
| SBFNL-14063-BC-ID2 | 1.28 | 24 |
| SBFNL-14063-BC-ID3 | 1.76 | 24 |
| SBFNL-14063-BC-ID4 | No Peak | 72 |
| SBFNL-14063-BC-ID5 | No Peak | 72 |
| SBFNL-14063-BC-ID6 | No Peak | 72 |

TABLE 8

Drug Concentration in the Plasma

| ID | Drug concentration (ng/g) | Time point (h) |
|---|---|---|
| SBFNL-14051-ID4 | 156.0 | 3* |
| SBFNL-14051-ID5 | 136.0 | 3* |
| SBFNL-14051-ID6 | 209.0 | 3* |
| SBFNL-14063-BC-ID1 | 0.163 | 24 |
| SBFNL-14063-BC-ID2 | 0.0913 | 24 |
| SBFNL-14063-BC-ID3 | 0.14 | 24 |
| SBFNL-14063-BC-ID4 | No Peak | 72 |
| SBFNL-14063-BC-ID5 | No Peak | 72 |
| SBFNL-14063-BC-ID6 | No Peak | 72 |

Phase II. Effect of Compound on be Behavior Assays

For this study, we use Thy1-APP$^{Lond/Swe}$ mice. This line presents well-established cognitive deficits[3], mature β-amyloid plaques, and synaptic degeneration in various brain regions[4]. The animals will be treated with JJS-1-166 and its efficacy will be evaluated using a series of behavioral tests.

2.

LC-MS/MS Method Development for Compound JJS-1-166

Compound: JJS-1-166; Molecular weight: 391.51

LC Method

| Column | DIONEX Acclaim120 C18 5 um 2.1 × 100 mm |
|---|---|
| Column Temperature: | 25° C. |
| Flow Rate: | 0.3 ml/min |
| Injection Volume: | 10 μl |
| Autosampler Temperature: | 10° C. |
| Run Time: | 2.6 min |

-continued

| Mobile Phase: | A: H$_2$O with 0.1% v/v Formic Acid<br>B: HPLC Grade Acetonitrile with 0.1% v/v Formic Acid |
|---|---|
| Mobile Phase Program: | 60% B isocratic |
| Peak retention time: | 1.32-1.33 min |

MRM Method

| Compound | Q1 Mass | Q3 Mass | DP (volts) | EP (volts) | CE (volts) | CXP (volts) |
|---|---|---|---|---|---|---|
| 166 | 392.217 | 301.1 | 96 | 10 | 27 | 26 |
| 166 | 392.217 | 91.0 | 96 | 10 | 75 | 6 |

DP: Declustering Potential;
EP: Entrance Potential;
CE: Collision Energy;
CXP: Collision Cell Exit Potential

3.

General Methods.

Unless otherwise noted, solvents and reagents were reagent-grade and used without further purification. Dichloromethane (CH$_2$Cl$_2$), diisopropylamine (i-Pr$_2$NH) and triethylamine (Et$_3$N) were freshly distilled over CaH$_2$. Tetrahydrofuran (THF), ether (Et$_2$O), acetonitrile (CH$_3$CN), and toluene were dried according to the procedure described by Grubbs. Pangborn, A. B.; Giardello, M. A.; Grubbs, R. H.; Rosen, R. K.; Timmers, F. J. "Safe and Convenient Procedure for Solvent Purification" *Organometallics* 1996, 15, 1518-1520. Reactions were performed under nitrogen or argon atmosphere in round-bottom flasks sealed under rubber septa with magnetic stirring, unless otherwise noted. Water sensitive reactions (e.g. metallations) were performed with flame- or oven-dried glassware, stir bars, steel needles, and cannulae. Reaction temperatures are reported as the temperatures of the bath surrounding the vessel, or programmed temperatures for microwave reactions. Microwave reactions were performed using a CEM Discover Labmate microwave synthesizer. Sensitive reagents and solvents were transferred using plastic or oven-dried glass syringes and steel needles using standard techniques.

Nuclear magnetic resonance spectra were acquired at 300K and in CDCl$_3$ unless otherwise noted. Chemical shifts are reported in parts per million (ppm, δ), downfield from trimethylsilane (TMS, δ=0.00 ppm) and are referenced to the residual solvent: CDCl$_3$, δ=7.26 ppm ($^1$H) and 77.16 ppm ($^{13}$C); CD$_3$OD, δ=3.31 ppm ($^1$H) and 49.0 ppm ($^{13}$C); d$_6$-DMSO, δ=2.50 ppm ($^1$H) and 39.5 ppm ($^{13}$C); d$_6$-acetone, δ=2.05 ppm ($^1$H) and 29.8 ppm ($^{13}$C). Gottlieb, H. B.; Kotlyar, V.; Nudelman, A. "NMR Chemical Shifts of Common Laboratory Solvents as Trace Impurities" *J. Org. Chem.* 1997, 62, 7512-7515. The abbreviations s, d, t, q, p, hex, hep, m and comp stand for the resonance multiplicities singlet, doublet, triplet, quartet, pentuplet, hextuplet, heptuplet, multiplet, and complex (overlapping multiplets of non-chemically equivalent protons), respectively. br=broad; app=apparent. Infra red (IR) spectra were recorded as films on sodium chloride plates and reported as wavenumbers (cm$^{-1}$).

Thin-layer chromatography was performed on Merck Kieselgel 60 F254 silica gel plates eluting with solvents indicated, visualized by 254 nm UV lamp, and stained with 100 basic KMnO$_4$ solution or p-anisaldehyde, unless otherwise noted. Silica gel purifications were performed with either flash chromatography or radial preparative layer chromatography (radial plc) using 1 mm, 2 mm, or 4 mm plates. Still, W. C.; Kahn, M.; Mitra, A. "Rapid Chromatographic Technique for Preparative Separations with Moderate Resolution" *J Org. Chem.* 1978, 43, 2923-2925.

Alternatively, tetrahydrofuran was dried by filtration through two columns of activated, neutral alumina according to the procedure described by Grubbs. Acetonitrile (MeCN) was dried by filtration through two columns of activated molecular sieves, and toluene was dried by filtration through one column of activated, neutral alumina followed by one column of Q5 reactant. These solvents were determined to have less than 50 ppm H2O by Karl Fischer coulometric moisture analysis. Methylene chloride ($CH_2Cl_2$), triethylamine ($Et_3N$) and diisopropylethylamine (i-$Pr_2$NEt) were distilled from calcium hydride immediately prior to use. Where required, solvents were degassed by sparging with argon prior to use. All reagents were reagent grade and used without purification unless otherwise noted, and air or moisture sensitive reagents were weighed in a glove box. All reactions involving air or moisture sensitive reagents or intermediates were performed under an inert atmosphere of nitrogen or argon in glassware that was flame or oven dried. Reaction temperatures refer to the temperature of the cooling/heating bath.

Volatile solvents were removed under reduced pressure using a Btichi rotary evaporator at 25-30° C. (bath temperature). Thin layer chromatography was run on pre-coated plates of silica gel with a 0.25 mm thickness containing 60F-254 indicator (EMD Millipore). Chromatography was performed using forced flow (flash chromatography) and the indicated solvent system on 230-400 mesh silica gel (Silicycle flash F60) according to the method of Still, ii unless otherwise noted. Radial Preparative Liquid Chromatography (radial plc) was performed on a Chromatotron® using glass plates coated with Merck, TLC grade 7749 silica gel with gypsum binder and fluorescent indicator. Infrared (IR) spectra were obtained either neat on sodium chloride or as solutions in the solvent indicated and reported as wavenumbers ($cm^{-1}$).

Proton nuclear magnetic resonance ($^1$H NMR) and carbon nuclear magnetic resonance ($^{13}$C NMR) spectra were obtained at the indicated field as solutions in CDCl3 unless otherwise indicated. Chemical shifts are referenced to the deuterated solvent (e.g., for CDCl3, δ=7.26 ppm and 77.0 ppm for $^1$H and $^{13}$C NMR, respectively) and are reported in parts per million (ppm, 6) relative to tetramethylsilane (TMS, δ=0.00 ppm). Coupling constants (J) are reported in Hz and the splitting abbreviations used are: s, singlet; d, doublet; t, triplet; q, quartet; m, multiplet; comp, overlapping multiplets of magnetically nonequivalent protons; br, broad; app, apparent. Purity was determined using an LCMS system comprised of an Agilent 1200 Series HPLC and an Agilent 6130 single quadrupole mass spectrometer. Samples were injected onto a Phenomenex Gemini C18 column (5 micron, 2.1×50 mm) and eluted at 0.7 ml/min using a gradient of 10-90% acetonitrile, 0.1% formic acid (11 minute linear ramp). Positive mode electrospray ionization was used to verify the identity of the major component, and the purity was assessed via peak integration (AUC) of the UV chromatogram recorded at 214 nm.

Allyl-[1-(2-bromo-6-chloro-phenyl)-but-3-enyl]-carbamic acid benzyl ester (2)

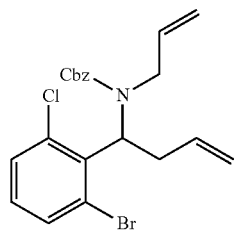 [SMILES: C=CCC(c1c(Cl)cccc1Br)N(CC=C)C(=O)OCc1ccccc1]

A mixture of allylamine (971 mg, 1.27 mL, 17.0 mmol), 2-bromo-6-chlorobenzaldehyde (1.87 g, 8.51 mmol) and 4 Å molecular sieves (2.0 g) was stirred in $CH_2Cl_2$ (20 mL) for 12 h at room temperature. The sieves were removed by filtration through Celite, and the filtrate was concentrated under reduced pressure to afford 2.20 g (ca. 100%) of crude imine, which was used directly in the next step. Benzyl chloroformate (1.60 g, 1.34 mL, 9.39 mmol) was added to a solution of imine in THF (17 mL) and was heated at 60° C. for 1 h. The reaction was then cooled to -78° C., and a freshly prepared solution of allylzinc bromide (ca. 13.1 mmol) in THF (10 mL) was added and the reaction stirred for 2 h. Negishi, E.; Boardman, L. D.; Sawada, H.; Bagheri, V.; Stoll, T. A.; Tour, J. M.; Rand, C. L. "Novel Cyclialkylation Reactions of (Omega-Halo-1-Alkenyl)Metal Derivatives-Synthetic Scope and Mechanism" *J. Am. Chem. Soc.* 1988, 110, 5383-5396. The cooling bath was removed, and the reaction was allowed to warm to 0° C. and quenched with saturated aqueous $NH_4Cl$ (~10 mL). The mixture was partitioned between water (100 mL) and $Et_2O$ (100 mL), and the layers were separated. The aqueous layer was extracted with $Et_2O$ (3×50 mL) and the combined organic extracts were washed with aqueous $NaHCO_3$ (100 mL) and brine (50 mL), dried ($MgSO_4$), filtered, and concentrated under reduced pressure. The crude product was purified by flash chromatography eluting with hexanes/EtOAc (100:0; 95:5; 90:10; 85:15) to give 3.31 g (89%) of 2 as a pale yellow oil: $^1$H NMR (400 MHz, CDCl3) δ 7.60-7.40 (m, 1H), 7.40-7.10 (comp, 6H), 7.00 (t, J=10.8 Hz, 1H), 5.94-5.82 (m, 1H), 5.80-5.66 (comp, 2H), 5.35-4.80 (comp, 6H), 4.32 (br d, J=22.4 Hz, 1H), 4.05 (dd, J=23.0, 6.80 Hz, 1H), 3.05-2.94 (m, 1H), 2.89-2.81 (m, 1H); $^{13}$C NMR (75 MHz, CDCl3) δ 155.9, 137.3, 136.4, 135.5, 133.4, 132.5, 130.1, 128.7, 128.2, 127.9, 127.7, 117.9, 115.1, 67.1, 59.3, 47.6, 35.0; IR (thin film, neat) 3078, 2978, 1715, 1448, 1401, 1254 $cm^{-1}$; mass spectrum (ESI) m/z 434.0518 [$C_{21}H_{22}NO_2ClBr$ (M+1) requires 434.0517].

Preparation of Allyl-[1-(2-bromo-5-chlorophenyl)-but-3-enyl]-carbamic acid benzyl ester (10)

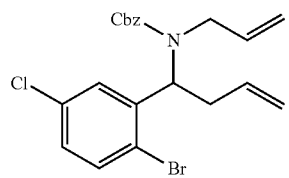

A solution of allyl-(2-bromo-5-chlorobenzylidene)amine (2.20 g, 8.51 mmol), which was prepared from allylamine and compound 7 in THF (17 mL) and benzyl chloroformate (1.34 mL, 9.39 mmol) was heated at 60° C. for 1 h. The mixture was then cooled to -78° C., and a solution of allylzinc bromide (ca. 13.1 mmol) in THF (10 mL) was added. 51 The cooling bath was removed, and the mixture was stirred at room temperature for 1.5 h. Saturated aqueous $NH_4Cl$ (~4 mL) was added, and the mixture was partitioned between water (100 mL) and $Et_2O$ (100 mL), and the layers were separated. The organic layer was washed with $NaHCO_3$ (100 mL) and brine (50 mL), dried ($MgSO_4$), filtered, and concentrated under reduced pressure. The crude product was purified by flash chromatography, eluting with 0-20% EtOAc/hexanes, to give 3.31 g (89%) of 32 as a pale yellow oil. $^1$H NMR (400 MHz, CDCl3) (rotamers) δ 7.46 (d, J=8.4 Hz, 1H), 7.43-7.28 (comp, 6H), 7.12 (dd, J=8.4, 2.4

Hz, 1H), 5.75 (br s, 1H), 5.60 (br m, 1H), 5.44 (app t, J=12.8 Hz, 1H), 5.21 (d, J=14.0 Hz, 1H), 5.20 (d, J=14.0 Hz, 1H), 5.10 (d, J=17.6 Hz, 1H), 5.04 (d, J=10.4 Hz, 1H), 4.89 (d, J=10.4 Hz, 1H), 4.87 (d, J=17.6 Hz, 1H), 3.75 (dd, J=16.0, 5.6 Hz, 1H), 3.64 (br m, 1H), 2.77 (br m, 1H), 2.67 (br m, 1H); $^{13}$C NMR (100 MHz, CDCl$_3$) (rotamers) δ 155.9, 140.3, 136.7 (br), 134.5, 134.4, 134.0, 133.4, 129.6 (br), 129.3, 128.5, 128.2 (br), 128.0, 123.8, 118.1, 116.4, 67.4, 58.5, 47.0, 36.3; IR (neat) 3076, 2938, 1698, 1453, 1406, 1236, 1142, 1096, 1025, 992, 918, 814, 766 cm$^{-1}$; mass spectrum (CI$^+$) m/z 434.0524 [C$_{21}$H$_{22}$NO$_2$$^{35}$Cl$^{79}$Br (M+1) requires 434.0522].

Benzyl 6-(2-bromo-6-chlorophenyl)-5,6-tetrahydro-pyridine-1(2H)-carboxylate (3)

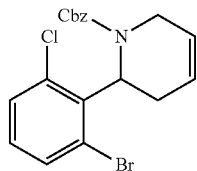

Grubbs 2$^{nd}$ generation catalyst (50 μmol, 49 mg) was added to a solution of 2 (500 mg, 1.15 mmol) in CH$_2$Cl$_2$ (25 mL). After stirring for 14.5 h at room temperature, the reaction was concentrated under reduced pressure. The residue was dissolved in 15% EtOAc/hexanes and filtered through a plug of silica gel to remove the catalyst. The filter plug was rinsed with 15% EtOAc/hexanes (3×20 mL) and the combined washings and filtrate were concentrated under reduced pressure to give the crude product, which was purified via flash chromatography (SiO$_2$) eluting with hexanes/EtOAc (100:0; 95:5) to give 434 mg (93%) of 3 as a colorless oil: $^1$H NMR (400 MHz, CDCl$_3$) δ 7.42 (d, J=7.8 Hz, 1H), 7.28-7.05 (comp, 6H), 6.97 (t, J=8.4 Hz, 1H), 6.16-6.03 (comp, 2H), 5.43 (t, J=8.0 Hz, 1H), 5.03 (d, J=11.6 Hz, 1H), 4.92-4.84 (m, 1H), 4.47-4.43 (m, 1H), 4.00 (d, J=16.8 Hz, 1H), 2.49 (app d, J=8.0 Hz, 2H); $^{13}$C NMR (75 MHz, CDCl$_3$) δ (rotamers) δ 155.9, 139.9, 136.6, 133.5, 132.7, 130.4, 128.5, 128.4, 128.3, 128.0, 127.4, 126.3, 123.8, 67.5, 55.1, 53.7, 42.7, 27.7; IR (thin film, neat) 3044, 2944, 2851, 1695, 1415, 1328, 1228 cm$^{-1}$; mass spectrum (ESI) m/z 428.0023 [C$_{19}$H$_{17}$NO$_2$NaClBr (M+Na) requires 428.0023].

5-Chloro-9-aza-tricyclo[6.3.1.0$^{2,7}$]dodeca-2,4,6,10-tetraene-9-carboxylic acid benzyl ester (16)

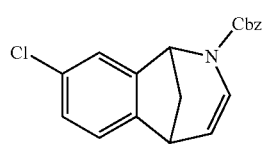

(16)

A solution of compound 10 (1.29 g, 2.97 mmol) in benzene (30 mL) containing Grubbs II catalyst (63 mg, 0.074 mmol) was heated at 80° C. for 15 h. 2-Mercaptonicotinic acid (230 mg, 1.48 mmol) was added to aid with catalyst removal, and stirring at room temperature was continued for 1 h. The mixture was then washed twice with aqueous NaHCO$_3$ (20 mL) and brine (20 mL) and then stirred for 0.5 h over activated charcoal (3 g). The mixture was filtered and concentrated to ca. 10 mL. This solution was diluted to make a ~0.04 M stock solution of compound 13. A 10-mL portion of this solution (ca. 0.37 mmol) was added to a 40-mL CEM microwave vial and sparged with argon for 15 min. Tetrabutylammonium chloride (139 mg, 0.50 mmol), Pd(OAc)$_2$ (11 mg, 0.049 mmol), P(o-tol)$_3$ (30 mg, 0.10 mmol), and (i-Pr)$_2$NEt (129 mg, 174 mL, 1.0 mmol) were added. The vial was capped, flushed with argon, and heated via microwave at 100° C. for 1 h. The mixture was filtered through a plug of SiO$_2$, which was washed with 50% EtOAc/hexanes. The combined filtrate and washings were concentrated, and the residue was purified by flash chromatography, eluting with 0-25% EtOAc/hexanes, to yield 93 mg (77% from 10) of 16 as a colorless oil. $^1$H NMR (400 MHz, CDCl$_3$) (rotamers) δ 7.49-7.30, 7.20-7.07 (comp, 8H), 6.50 (d, J=7.9 Hz, 0.42H), 6.40 (d, J=7.9 Hz, 0.58H), 5.58 (d, J=4.1 Hz, 0.58H), 5.45 (d, J=4.1 Hz, 0.42H), 5.38-5.06 (comp, 4H), 3.33 (dd, J=10.7, 5.1 Hz, 1H), 2.32 (m, 1H), 2.10 (d, J=10.7 Hz, 0.42H), 2.09 (d, J=10.7 Hz, 0.58H); $^{13}$C NMR (100 MHz, CDCl$_3$) (rotamers) δ 152.1, 152.0, 147.24, 147.15, 140.7, 140.5, 136.1, 135.9, 132.3, 132.1, 128.8, 128.59, 128.59, 128.56, 128.4, 128.3, 128.2, 124.4, 124.0, 122.1, 121.9, 121.75, 121.72, 110.7, 109.9, 67.90, 67.85, 57.8, 57.4, 37.99, 37.94, 37.8, 37.5; IR (neat) 1702, 1399, 1336, 1250, 1112, 694 cm$^{-1}$; mass spectrum (CI$^+$) m/z 326.0949 [C$_{19}$H$_{17}$NO$_2$$^{35}$Cl (M+1) requires 326.0948].

6-Chloro-9-aza-tricyclo[6.3.1.0$^{2,7}$]dodeca-2,4,6,10-tetraene-9-carboxylic acid benzyl ester (10)

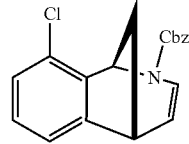

A solution of tetrahydropyridine 3 (1.0 g, 2.45 mmol) in degassed acetonitrile (17 mL) was added to a 40-mL CEM microwave vial containing tetrabutylammonium chloride (681 mg, 2.45 mmol), Pd(OAc)$_2$ (55 mg, 0.245 mmol) and P(o-tol)$_3$ (150 mg, 0.49 mmol). (i-Pr)$_2$NEt (0.85 mL, 4.9 mmol) was added, the vial was capped and flushed with argon, then stirred for 2 min at room temperature. The reaction was heated in the microwave (300 W) at 100° C. for 1 h, whereupon the mixture was filtered through a plug of SiO$_2$ and washed with 50% EtOAc/hexanes (2×20 mL). The combined filtrate and washings were concentrated, and the residue was purified by column chromatography (SiO$_2$) eluting with hexanes/EtOAc (100:0; 95:5; 90:10) to yield 750 mg (94%) of 10 as a colorless oil. H NMR (400 MHz, CDCl$_3$) δ 7.48 (br d, J=7.2 Hz, 1H), 7.42-7.31 (comp, 4H), 7.14-7.11 (comp, 2H), 7.05-7.03 (m, 1H), 6.53 and 6.43 (rotamers, d, J=7.6 Hz, 1H), 5.94 and 5.77 (rotamers, d, J=2.8 Hz, 1H), 5.34-5.30 and 5.26-5.15 (comp, 3H), 3.40-3.35 (m, 1H), 2.39-2.27 (m, 1H), 2.10 (d, J=10.4 Hz, 1H); $^{13}$C NMR (75 MHz, CDCl$_3$) δ (rotamers) 152.4, 151.9, 151.3, 137.12, 136.8, 136.2, 130.3, 130.0, 129.9, 128.9, 128.7, 128.6, 128.4, 127.3, 122.2, 121.9, 119.0, 118.9, 110.6, 110.0, 68.3, 68.1, 57.1, 56.5, 39.4, 39.2, 37.6, 37.5; IR (thin film, neat) 3064, 3031, 2958, 1715, 1628, 1461, 1401, 1321, 1248, 1114 cm$^{-1}$; mass spectrum (ESI) m/z 326.0945 [C$_{19}$H$_{17}$NO$_2$Cl (M+1) requires 326.0948].

Preparation of 5-Chloro-9-aza-tricyclo[6.3.1.0$^{2,7}$]dodeca-2,4,6-triene-9-carboxylic acid benzyl ester (18{2})

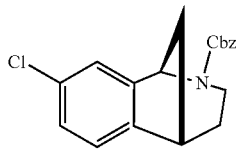

Triethylsilane (186 mg, 0.25 mL, 1.6 mmol) and trifluoroacetic acid (308 mg, 0.2 mL, 2.7 mmol) were added to a solution of 16 (84 mg, 0.26 mmol) in CH$_2$Cl$_2$ (5 mL) at 0° C. The solution was stirred for 2 h at 0° C. and then at room temperature for 10 h. Saturated aqueous NaHCO$_3$ (5 mL) was added, and the layers were separated. The aqueous layer was extract with CH$_2$Cl$_2$ (2×5 mL), and the combined organic layers were dried (MgSO$_4$), filtered, and concentrated under reduced pressure. The residue was purified by flash chromatography, eluting with 0-50% EtOAc/hexanes, to yield 78 mg (91%) of compound 18{2} as a colorless oil. $^1$H NMR (400 MHz, CDCl$_3$) (rotamers) δ 7.48-7.10 (comp, 8H), 5.49 (br s, 0.55H), 5.38 (br s, 0.45H), 5.15 (m, 2H), 3.83 (br m, 1H), 3.25 (br m, 1H), 2.43 (br m, 1H), 2.19 (br m, 1H), 1.98 (br m, 1H), 1.87 (d, J=11.0 Hz, 1H), 1.57 (br m, 1H); $^{13}$C NMR (100 MHz, CDCl$_3$) (rotamers) δ 154.9, 154.7 (br), 144.7, 142.9 (br), 142.7 (br), 136.8 (br), 136.7, 132.6, 128.5, 127.9, 124.2, 123.8 (br), 67.1, 57.4 (br), 57.2, 43.6, 39.3, 38.5, 30.1; IR (neat) 2943, 1693, 1415, 1305, 1263, 1200, 1097, 1055, 697 cm$^{-1}$; mass spectrum (CEI) m/z 328.1106 [C$_{19}$H$_{19}$NO$_2$$^{35}$Cl (M+1) requires 328.1104].

Preparation of 5-Chloro-9-aza-tricyclo[6.3.1.0$^{2,7}$]dodeca-2,4,6-triene (22{2})

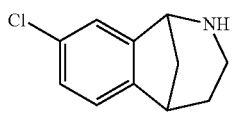

TMSI (258 mg, 183 mL, 1.29 mmol) was added dropwise to a stirred solution of compound 18{2} (211 mg, 0.644 mmol) in dry CH$_2$Cl$_2$ (6.4 mL) at 0° C. The solution was stirred for 1 h, whereupon methanolic HCl (ca. 7 mmol in 2.5 mL MeOH) was added dropwise. The solution was concentrated and then partitioned between 1 M HCl (15 mL) and Et$_2$O (15 mL). The layers were separated, and the aqueous phase was washed with Et$_2$O (2×10 mL). The aqueous layer was then basified to pH 10, saturated with NaCl, and extracted with EtOAc (2×10 mL). The organic phase was dried (Na$_2$SO$_4$), filtered, and concentrated to give 106 mg (85%) of compound 22{2} as a colorless oil. $^1$H NMR (400 MHz, CDCl$_3$) δ 0.23-7.16 (comp, 2H), 7.12 (d, J=7.6 Hz, 1H), 4.19 (d, J=4.7 Hz, 1H), 2.72 (dd, J=12.1, 5.9 Hz, 1H), 2.28 (ddd, J=12.4, 12.4, 4.7 Hz, 1H), 2.18 (m, 1H), 1.95 (dddd, J=12.4, 12.4, 5.9, 2.1 Hz, 1H), 1.91 (app br d, J=10.6 Hz, 1H); $^{13}$C NMR (100 MHz, CDCl$_3$) δ 145.0, 144.7, 132.3, 127.5, 123.5, 123.3, 58.8, 45.3, 39.8, 39.1, 31.0; IR (neat) 2939, 2854, 1464, 1394, 1304, 1077, 877, 823 cm$^{-1}$; mass spectrum (CEI) m/z 194.0740 [C$_{11}$H$_{13}$N$^{35}$Cl (M+1) requires 194.0737].

Preparation of Benzyl 8-(4-fluorophenyl)-4,5-dihydro-1H-1,5-methanobenzo[c]azepine-2(3H)-carboxylate (20{2,10})

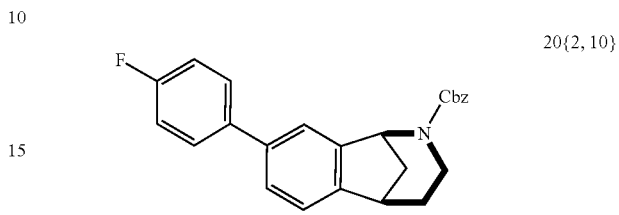

A solution of carbamate 18{2} (92 mg, 0.28 mmol), p-fluorophenylboronic acid (19{10}) (79 mg, 0.56 mmol), Cs$_2$CO$_3$ (183 mg, 0.56 mmol), palladium(bis)(t-butyl)$_3$phosphine (7.2 mg, 0.014 mmol) in degassed 1,4-dioxane (0.85 mL) was stirred for 21 h at 100° C. The reaction was cooled to room temperature and poured into water (2 mL). The mixture was extracted with CH$_2$Cl$_2$ (3×15 mL), and the combined organic layers were dried (MgSO4) and concentrated under reduced pressure to provide the crude product, which was purified via radial plc (SiO$_2$) eluting with hexanes/EtOAc (100:0; 95:5; 90:10) to give 101 mg (94%) of 20{2,10} as a colorless oil: $^1$H NMR (400 MHz) δ 7.54-7.29 (comp, 10H), 7.12 (t, J=8.8 Hz, 2H), 5.64-5.56 and 5.50-5.45 (rotomers, m, 1H), 5.29-5.10 (m, 2H), 3.95-3.79 (m, 1H), 3.33 (d, J=2.0 Hz, 1H), 2.59-2.45 (m, 1H), 2.27 (br s, 1H), 2.03 (br s, 1H), 1.93 (d, J=11.2, 1H), 1.71-1.58 (m, 1H); $^{13}$C NMR (75 MHz) (rotomers) δ 162.7 (d, JC-F=245 Hz), 155.3, 145.7, 142.2, 139.9, 137.5, 137.1, 129.0, 128.8, 128.7, 128.2, 127.5, 123.3, 122.8, 115.9 (d, JC-F=21.3 Hz), 67.3, 57.9, 57.6, 44.0, 39.7, 38.9, 30.5; IR (thin film, neat) 2951, 1695, 1421, 1234, 1101 cm$^{-1}$; mass spectrum (ESI) m/z 388.1709 [C$_{25}$H$_{23}$FNO$_2$ (M+1) requires 388.1713]; LCMS purity 99%.

Preparation of Benzyl 8-morpholino-4,5-dihydro-1H-1,5-methanobenzo[c]azepine-2(3H)-carboxylate (20{2,2})

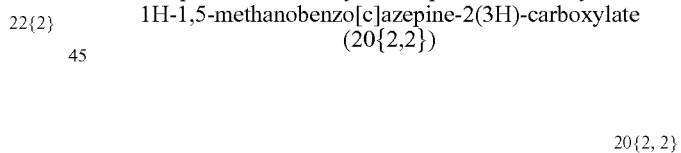

A solution of carbamate 18{2} (130 mg, 0.396 mmol), NaO-t-Bu (53 mg, 0.55 mmol) and morpholine (45 mg, 0.515 mmol) in degassed toluene (0.75 mL) was stirred for 5 min. A freshly prepared toluene solution of Pd(OAc)$_2$ and di-tert-butylphosphine biphenyl (JohnPhos®) (1:1, 0.1 mL, 0.08 M), that had been stirred for 20 min, was added to the reaction mixture via syringe. After heating at 100° C. for 4.75 h, the reaction was cooled to room temperature, poured into water (3 mL) and extracted with CH$_2$Cl$_2$ (3×15 mL). The combined organic extracts were dried (K$_2$CO$_3$), filtered and concentrated under reduced pressure to provide the crude product, which was purified via radial plc (SiO$_2$), eluting with hexanes/EtOAc (100:0; 90:10; 80:20) to give 146 mg (97%) of 20{2,2} as a pale yellow oil: $^1$H NMR (400 MHz) δ 7.43-7.27 (comp, 5H), 7.13 (d, J=8.2 Hz, 1H), 6.96 and 6.78 (rotomers, s, 1H), 6.80 (dd, J=8.2, 2.4 Hz, 1H), 5.47 and 5.35 (rotomers, br s, 1H), 5.27-5.07 (m, 2H), 3.85 (t, J=4.8 Hz, 4H), 3.84-3.65 (m, 1H), 3.21 (br s, 1H), 3.11 (app br d, J=19.2 Hz, 4H), 2.53-2.38 (m, 1H), 2.30-2.12 (m, 1H), 2.05-1.90 (m, 1H), 1.85 (d, J=10.4 Hz, 1H), 1.64-1.50 (m, 1H); $^{13}$C NMR (75 MHz) (rotomers) δ 155.3, 155.1, 151.4, 142.6, 142.3, 138.1, 137.4, 137.2, 128.7, 128.2, 128.1, 123.4, 116.1, 115.8, 112.2, 112.0, 67.2, 67.1, 58.3, 58.0, 53.8, 50.2, 44.0, 39.2, 38.9, 30.7; IR (thin film, neat) 2958, 2851, 1695, 1615, 1495, 1421, 1234, 1121 cm$^{-1}$; mass spectrum (ESI) m/z 379.2016 [$C_{23}H_{27}N_2O_3$ (M+1) requires 379.2022]; LCMS purity 100%.

Preparation of 8-(Benzo[d][1,3]dioxol-5-yl)-2-benzyl-2,3,4,5-tetrahydro-1H-1,5-methanobenzo[c]azepine (21 {2,11})

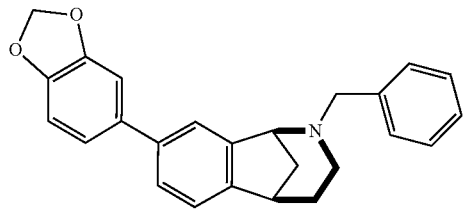

21{2,11}

Reaction carried out in the dark. A solution of carbamate 20{2,11}(99 mg, 0.24 mmol) and TMSI (95 mg, 0.48 mmol) in CH$_2$Cl$_2$ (4.0 mL) was stirred for 3 h at 0° C. MeOH (3 mL) and a saturated aqueous NaHCO$_3$ solution (3 mL) were added, and the mixture was stirred for 10 min. The MeOH was removed under reduced pressure, and the aqueous mixture was extracted with CH$_2$Cl$_2$ (3×10 mL). The combined organic extracts were dried (K$_2$CO$_3$), filtered and concentrated under reduced pressure, and the residue was purified via radial plc (SiO$_2$), eluting with hexanes/EtOAc (100:0; 95:5; 90:10) to give 70 mg (79%) of benzylamine 21{2,11} as a white solid: mp 142-143° C.; $^1$H NMR (300 MHz) δ 7.46-7.27 (comp, 8H), 7.14 (comp, 2H), 6.95 (d, J=7.5 Hz, 1H), 6.05 (s, 2H), 3.97 (d, J=4.8 Hz, 1H), 3.53 (d, J=13.3 Hz, 1H), 3.35 (d, J=13.3 Hz, 1H), 3.24-3.16 (m, 1H), 2.63 (dd, J=10.8, 5.7 Hz, 1H), 2.30-2.20 (m, 1H), 2.12-1.97 (comp, 2H), 1.62-1.53 (comp, 2H); $^{13}$C NMR (75 MHz) δ 148.4, 147.1, 145.8, 140.0, 139.4, 136.4, 129.4, 128.6, 127.1, 126.6, 122.9, 120.9, 108.9, 108.1, 101.4, 63.0, 60.6, 47.3, 45.0, 39.9, 30.6; IR (thin film, neat) 3031, 2935, 2811, 1506, 1465, 1224, 1046 cm$^{-1}$; mass spectrum (ESI) m/z 370.1804 [$C_{25}H_{24}NO_2$ (M+1) requires 370.1802]; LCMS purity 100%.

Preparation of 8-(4-Fluorophenyl)-2,3,4,5-tetrahydro-1H-1,5-methanobenzo[c]azepine (23 {2,10})

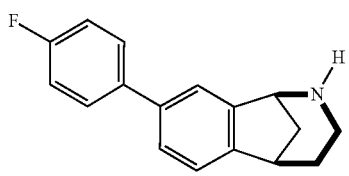

23{2,10}

Reaction carried out in the dark. A solution of carbamate 20{2,10}(244 mg, 0.63 mmol) and TMSI (250 mg, 1.25 mmol) in CH$_2$Cl$_2$ (7 mL) was stirred for 3 h at 0° C. Methanolic HCl (2.5 mL, 1.8 M) was added and after stirring for 5 min, the reaction was concentrated under reduced pressure. Diethyl ether (5 mL) was added and the solution was stirred for 5 min. The solids were allowed to settle and the supernatant was removed via syringe. Aqueous NaOH (5 mL, 2.7 M) was added to the remaining solid and the mixture was stirred for 5 min. After the addition of CH$_2$Cl$_2$ (20 mL) and 5 more min of stirring, the layers were separated, and the aqueous layer was extracted with CH$_2$Cl$_2$ (3×10 mL). The combined organic layers were dried (K$_2$CO$_3$), filtered, and concentrated under reduced pressure and the residue was purified via radial plc (SiO$_2$), eluting with hexanes/EtOAc/Et$_3$N/MeOH (100:0:0:0; 51:49:2:0; 0:98:2:0; 0:88:2:10) to give 141 mg (87%) of 23{2,10} as a light brown semi-solid: $^1$H NMR (400 MHz) δ 7.55-7.52 (comp, 2H), 7.42-7.39 (comp, 2H), 7.24 (s, 1H), 7.10 (t, J=9.2 Hz, 2H), 4.27 (d, J=4.0 Hz, 1H), 3.21 (s, 1H), 2.73 (dd, J=12.4, 6.0 Hz, 1H), 2.35 (td, J=12.4, 4.8 Hz, 1H), 2.23-2.20 (m, 1H), 2.11 (br s, 1H), 2.08-1.92 (comp, 2H), 1.56 (d, J=11.2 Hz, 1H); 13C NMR (75 MHz) δ 164.2, 160.9, 145.7, 143.9, 139.6, 137.9, 128.9, 126.7, 122.9, 121.9, 115.8 (d, JC-F=21.3 Hz), 59.1, 45.7, 40.2, 39.4, 31.5; IR (thin film, neat) 2941, 2852, 1526, 1224 cm$^{-1}$; mass spectrum (ESI) m/z 254.1344 [$C_{17}H_{17}FN$ (M+1) requires 254.1355]; LCMS purity 98%.

Preparation of 8-(m-Tolyl)-2,3,4,5-tetrahydro-1H-1,5-methanobenzo[c]azepine (23 ({2,9})

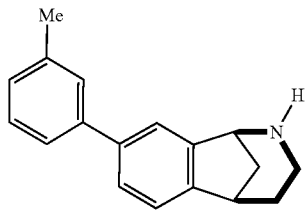

23{2,9}

A solution of 20{2,9)}(224 mg, 0.58 mmol) in EtOH (15 mL) and 10% Pd/C (93 mg) was stirred under an atmosphere of H$_2$ for 1 h at room temperature followed by concentration under reduced pressure. The residue was filtered through a plug of Celite® with multiple portions of EtOAc and the filtrate was concentrated under reduced pressure to provide 112 mg (77%) of 23{2,9} as a yellow oil that was of sufficient purity for use in subsequent reactions: $^1$H NMR (400 MHz) δ 7.48-7.45 (comp, 2H), 7.42-7.38 (comp, 2H), 7.32 (t, J=7.4 Hz, 1H), 7.25 (d, J=7.4 Hz, 1H), 7.15 (br d, J=7.4 Hz, 1H), 4.27 (d, J=4.0 Hz, 1H), 3.25-3.20 (m, 1H), 2.73 (dd, J=12.2, 5.8 Hz, 1H), 2.42 (s, 3H), 2.37 (td, J=12.2, 4.6 Hz, 1H), 2.25-2.19 (m, 1H), 2.03-1.96 (m, 1H), 1.95 (d, J=10.4 Hz, 1H), 1.78 (br s, 1H), 1.60-1.55 (m, 1H); $^{13}$C NMR (125 MHz) δ 145.3, 143.4, 141.5, 140.5, 138.2, 128.6, 127.9, 127.7, 126.7, 124.2, 122.5, 121.8, 58.9, 45.3, 40.0, 39.2, 31.2, 21.5; IR (thin film, neat) 3052, 2942, 2853, 1273 cm$^{-1}$; mass spectrum (ESI) m/z 250.1588 [$C_{18}H_{20}N$ (M+1) requires 250.1596]; LCMS purity 97%.

Preparation of 2-(Benzo[d][1,3]dioxol-5-ylmethyl)-8-(4-fluorophenyl)-2,3,4,5-tetrahydro-1H-1,5-methanobenzo[c]azepine (26{2,10,3})

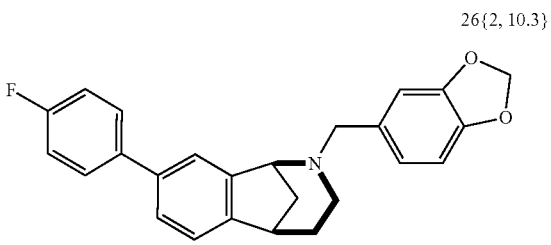

26{2,10,3}

A solution of amine 23{2,10}(25 mg, 0.098 mmol), Na(OAc)$_3$BH (33 mg, 0.16 mmol), piperonal (24{3}) (30 mg, 0.20 mmol) and acetic acid (10 µL) in 1,2-dichloroethane (2 mL) was stirred for 24 h at room temperature. The reaction was quenched with an aqueous, saturated NaHCO$_3$ solution (2 mL) and the layers were separated. The aqueous layer was extracted with CH$_2$Cl$_2$ (3×3 mL), and the combined organic layers were dried (K$_2$CO$_3$), filtered and concentrated under reduced pressure. The crude product was purified via radial plc (SiO$_2$) eluting with hexanes/EtOAc (100:0; 90:10; 80:20) to give 27 mg (71%) of 26{2,10,3} as a white solid: mp 106-108° C.; $^1$H NMR (300 MHz) δ 7.63-7.58 (m, 2H), 7.45 (d, J=6.3 Hz, 1H), 7.35 (s, 1H), 7.31-7.29 (m, 1H), 7.21-7.15 (m, 2H), 6.99 (s, 1H), 6.83-6.77 (m, 2H), 5.97 (s, 2H), 3.97 (d, J=4.5 Hz, 1H), 3.43 (d, J=13.3 Hz, 1H), 3.23 (d, J=13.3 Hz, 1H), 3.21-3.19 (m, 1H), 2.62-2.57 (m, 1H), 2.30-2.20 (m, 1H), 2.11-2.05 (m, 1H), 1.99 (d, J=10.5 Hz, 1H), 1.59-1.51 (m, 2H); $^{13}$C NMR (75 MHz) δ 162.6 (d, JC-F=244 Hz), 147.9, 146.7, 146.1, 140.2, 138.7, 138.1, 133.3, 129.0, 128.9, 126.7, 123.0, 122.2, 115.8 (d, JC-F=21.3 Hz), 109.7, 108.1, 101.1, 62.9, 60.3, 47.1, 44.9, 39.9, 30.5; IR (thin film, neat) 2942, 1492, 1238, 1039 cm$^{-1}$; mass spectrum (ESI) m/z 388.1711 [C$_{25}$H$_{23}$FNO$_2$ (M+1) requires 388.1707]; LCMS purity 100%.

Preparation of 2-((4-Methoxyphenyl)sulfonyl)-9-(4-(trifluoromethyl)phenyl)-2,3,4,5-tetrahydro-1H-1,5-methanobenzo[c]azepine (30{3,7,30})

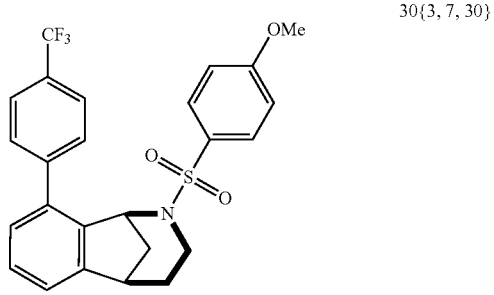

30{3,7,30} p-Methoxybenzenesulfonyl chloride (24{30}(28 mg, 0.14 mmol) was added to a stirred solution of amine 23{3,7}(21 mg, 0.07 mmol) and Et3N (28 mg, 0.28 mmol) in CH$_2$Cl$_2$ (1 mL) at room temperature. The solution was stirred for 12 h, and the mixture was concentrated under reduced pressure and purified via radial plc (SiO$_2$), eluting with hexanes/EtOAc (100:0; 95:5; 90:10) to provide 28 mg (85%) of sulfonamide 30{3,7,30} as a colorless oil: NMR (400 MHz) δ 7.71-7.64 (comp, 6H), 7.38 (t, J=7.6 Hz, 1H), 7.30-7.24 (comp, 3H), 6.92 (d, J=8.8 Hz, 2H), 5.27 (d, J=4.0 Hz, 1H), 3.88 (s, 3H), 3.74 (dd, J=14.4, 6.0 Hz, 1H), 3.28-3.23 (m, 1H), 2.84-2.75 (m, 1H), 1.97-1.89 (m, 1H), 1.88-1.82 (m, 1H), 1.70 (d, J=11.2 Hz, 1H), 1.56-1.52 (m, 1H); $^{13}$C NMR (125 MHz) δ 162.7, 147.9, 143.3, 137.9, 137.2, 133.0, 129.6, 129.4, 129.1, 128.0, 125.5, 125.4, 125.3, 122.5, 114.2, 58.4, 55.6, 41.8, 40.5, 40.0, 29.9; IR (thin film, neat) 2949, 2262, 1733, 1602, 1499, 1327, 1259 cm$^{-1}$; mass spectrum (ESI) m/z 474.1342 [C$_{25}$H$_{23}$NO$_3$F$_3$S (M+1) requires 474.1351]; LCMS purity 100%.

Preparation of Allyl 9-(4-(trifluoromethyl)phenyl)-4,5-dihydro-1H-1,5-methanobenzo[c]azepine-2(3H)-carboxylate (32{3,7,39})

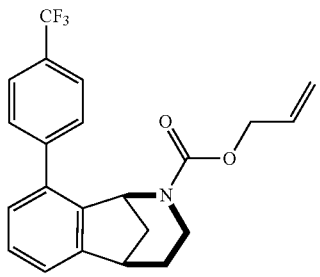

32{3,7,39}

Allyl chloroformate (24{39}) (29 mg, 0.24 mmol) was added to a solution of amine 23{3,7}(37 mg, 0.12 mmol) and Et$_3$N (37 mg, 0.37 mmol) in CH$_2$Cl$_2$ (0.75 mL) at room temperature, and the solution was stirred for 15 h. The mixture was concentrated under reduced pressure, and the residue was purified via radial plc (SiO$_2$) eluting with hexanes/EtOAc (100:0; 95:5) to give 34 mg (73%) of 32{3,7,39} as a white solid: mp 76-77° C.; $^1$H NMR (400 MHz) δ 7.64 (d, J=8.2 Hz, 2H), 7.46 (d, J=8.2 Hz, 2H), 7.38 (t, J=7.6 Hz, 1H), 7.31-7.24 (comp, 2H), 6.01-5.92 and 5.83-5.73 (rotomers, m, 1H), 5.42-5.25 (m, 1H), 5.24-5.14 (m, 2H), 4.70-4.18 (m, 2H), 4.05-3.98 (m, 1H), 3.38 (app br s, 1H), 2.72 and 2.57 (rotomers, td, J=13, 4.8 Hz, 1H), 2.19-2.16 (m, 1H), 2.10-1.99 (m, 1H), 1.92-1.86 (m, 1H), 1.68-1.63 (m, 1H); $^{13}$C NMR (75 MHz) δ (rotomers) 154.3, 154.1, 148.1, 147.8, 144.1, 143.7, 139.0, 138.8, 137.2, 133.5, 133.1, 129.8, 129.3, 127.9, 126.3, 125.5, 125.4, 122.7, 122.6, 117.9, 117.3, 66.3, 66.1, 56.7, 44.6, 44.3, 40.6, 39.0, 38.7, 31.1, 30.8; IR (thin film, neat) 3052, 2942, 2880, 1705, 1417, 1334, 1128 cm$^{-1}$; mass spectrum (ESI) m/z 388.1521 [C$_{22}$H$_{21}$NO$_2$F$_3$(M+1) requires 388.1524]; LCMS purity 100%.

Preparation of N-Phenethyl-9-(4-(trifluoromethyl)phenyl)-4,5-dihydro-1H-1,5-methanobenzo[c]azepine-2(3H)-carbothioamide (34{3,7,35})

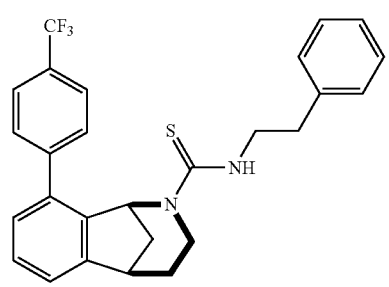

34{3,7,35}

Phenethylisothiocyanate 24{35}(33 mg, 0.20 mmol) was added to a solution of amine 23{3,7}(46 mg, 0.1 mmol) and Et₃N (10 mg, 0.1 mmol) in CH₂Cl₂ (0.75 mL) at room temperature and was stirred for 24 h. The reaction was concentrated, and the residue was purified via radial plc (SiO₂), eluting with hexanes/EtOAc (100:0; 90:10; 80:20) to give 41 mg (89%) of 34{3,7,35} as a white solid: mp (DCM/CH₃CN 3:1) 165-166° C.; $^1$H NMR (400 MHz) δ 7.65 (d, J=8.0 Hz, 2H), 7.41-7.38 (m, 3H), 7.24 (comp, 4H), 7.18 (comp, 3H), 5.24 (t, J=4.8 Hz, 1H), 4.03-3.95 (m, 1H), 3.81-3.75 (m, 1H), 3.43-3.40 (m, 1H), 2.98-2.91 (m, 1H), 2.88-2.74 (comp, 3H), 2.17-2.14 (m, 1H), 2.11-2.03 (m, 1H), 1.89 (d, J=10.8 Hz, 1H), 1.67 (d, J=12.8 Hz, 1H); 13C (125 MHz) δ (rotomers) 13C (125 MHz) δ 180.5, 147.8, 143.5, 138.8, 138.2, 137.0, 129.6 (q, JC-F=32.0 Hz), 129.5, 129.0, 128.7, 128.6, 127.7, 126.6, 125.6 (q, JC-F=3.75 Hz), 124.2 (q, JC-F=270 Hz), 122.4, 59.5, 46.8, 43.4, 40.8, 35.3, 30.9; IR (thin film, neat) 3397, 2973, 2925, 2863, 1542, 1399, 1330, 1269, 1180, 1139 cm$^{-1}$; mass spectrum (ESI) m/z 467.1764 [C₂₇H₂₆N₂F₃S (M+1) requires 467.1691]; LCMS purity 100%.

Preparation of Methyl 3-(8-(m-tolyl)-4,5-dihydro-1H-1,5-methanobenzo[c]azepin-2(3H)-yl)propanoate (35{2,9,40})

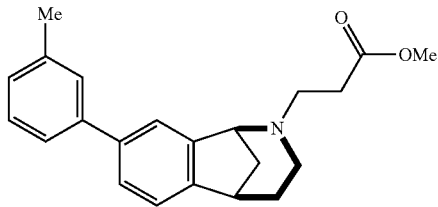

35{2,9,40}

Methyl acrylate 24{40}(25 mg, 0.28 mmol) was added to a solution of amine 23{2,9}(36 mg, 0.14 mmol) and Et₃N (14 mg, 0.14 mmol) in CH₂Cl₂ (3 mL). After stirring for 19 h at room temperature, the reaction was concentrated under reduced pressure, and the crude product purified via radial plc (SiO₂), eluting with hexanes/EtOAc (100:0; 95:0; 90:10) to give 39 mg (83%) of 35{2,9,40} as a white solid: mp 65-66° C.; $^1$H NMR (400 MHz) δ 7.46 (dd, J=7.6, 2.4 Hz, 1H), 7.42-7.38 (comp, 3H), 7.33 (t, J=7.8 Hz, 1H), 7.26 (d, J=7.6 Hz, 1H), 7.18-7.14 (m, 1H), 3.98 (d, J=4.8 Hz, 1H), 3.69 (s, 3H), 3.18-3.14 (m, 1H), 2.82-2.75 (m, 1H), 2.64 (dd, J=11.2, 5.2 Hz, 1H), 2.58-2.53 (m, 2H), 2.43 (s, 3H), 2.45-2.38 (m, 1H), 2.28-2.22 (m, 1H), 2.00 (td, J=15.2, 2.4 Hz, 1H), 1.94 (d, J=10.8 Hz, 1H), 1.59-1.51 (m, 1H), 1.50-1.44 (m, 1H); $^{13}$C NMR (75 MHz) δ 173.3, 145.6, 141.8, 139.9, 139.7, 138.5, 128.9, 128.3, 128.0, 126.9, 124.6, 123.1, 122.9, 64.2, 51.9, 51.7, 46.9, 44.9, 39.8, 33.3, 30.4, 21.8; IR (thin film, neat) 2941, 1732, 1478, 1272, 1203 cm$^{-1}$; mass spectrum (ESI) m/z 336.1963 [C₂₂H₂₆NO₂ (M+1) requires 336.1964]; LCMS purity 98%.

Benzyl 7-morpholino-4,5-dihydro-1H-1,5-methanobenzo[c]azepine-2(3H)-carboxylate (20{1,2})

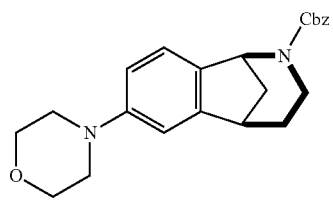

20{1,2}

88%, colorless oil. $^1$H NMR (400 MHz) δ 7.42-7.28 (comp, 5H), 7.23 and 7.12 (rotomers, d, J=7.4 Hz, 1H), 6.83 (d, J=2.4 Hz, 1H), 6.78-6.71 (m, 1H), 5.47-5.44 and 5.36-5.34 (rotomers, m, 1H), 5.21-5.10 (comp, 2H), 3.86 (t, J=4.9 Hz, 4H), 3.86-3.75 (m, 1H), 3.24-3.20 (m, 1H), 3.17 and 3.16 (rotomers, t, J=4.9 Hz, 4H), 2.54-2.38 (m, 1H), 2.26-2.12 (m, 1H), 2.03-1.90 (m, 1H), 1.86 (app d, J=10 Hz, 1H), 1.65-1.50 (m, 1H); $^{13}$C NMR (75 MHz) δ (rotomers) 155.1, 152.2, 148.0, 137.2, 132.9, 132.7, 128.7, 128.2, 128.1, 124.7, 124.6, 114.4, 110.8, 67.2, 67.1, 57.4, 57.1, 50.0, 44.3, 40.5, 38.8, 30.6; IR (thin film, neat) 2956, 2859, 1662, 1424, 1238, 1108 cm$^{-1}$; mass spectrum (ESI) m/z 379.2017 [C₂₃H₂₇N₂O₃(M+1) requires 379.2016]; LCMS purity 97%.

Benzyl 8-(benzo[d][1,3]dioxol-5-yl)-4,5-dihydro-1H-1,5-methanobenzo[c]azepine-2(3H)-carboxylate (20{2,11})

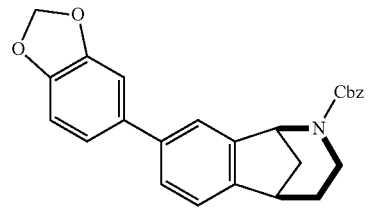

20{2,11}

73%, colorless, viscous oil: $^1$H NMR (400 MHz) δ 7.52-7.28 (comp, 7H), 7.27 (d, J=7.6 Hz, 1H), 7.08-7.01 (comp, 2H), 6.88 (d, J=7.6 Hz, 1H), 6.00 (s, 2H), 5.93-5.89 and 5.47-5.44 (rotomers, m, 1H), 5.29-5.14 (comp, 2H), 3.95-3.80 (m, 1H), 3.31 (app s, 1H), 2.60-2.48 (m, 1H), 2.31-2.18 (m, 1H), 2.07-1.98 (m, 1H), 1.92 (d, J=11.2 Hz, 1H), 1.72-1.58 (m, 1H); $^{13}$C NMR (100 MHz) δ (rotomers) 155.3, 155.1, 148.4, 147.2, 145.3, 142.1, 140.5, 137.3, 135.7, 128.7, 128.2, 127.3, 123.2, 122.6, 122.4, 120.8, 108.8, 107.9, 101.4, 67.3, 57.9, 57.6, 44.0, 39.7, 38.9, 30.5; IR (thin film, neat) 2945, 1696, 1475, 1235 cm$^{-1}$; mass spectrum (ESI) m/z 414.1706 [C₂₆H₂₄NO₄ (M+1) requires 414.1700]; LCMS purity 99%.

Benzyl 9-phenyl-4,5-dihydro-1H-1,5-methanobenzo[c]azepine-2(3H)-carboxylate

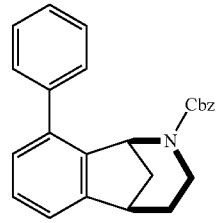

20{3,6}

82%, white solid: mp 97-98° C.; $^1$H NMR (400 MHz) δ 7.39-7.23 (comp, 13H), 5.43 (dd, J=17.0, 3.8 Hz, 1H), 5.27 and 5.00 (rotomers, d, J=12.4 Hz, 1H), 5.11 (dd, J=12.4, 4.4 Hz, 1H), 4.10-3.99 (m, 1H), 3.37 (app s, 1H), 2.75 and 2.64 (rotomers, td, J=12.9, 4.8 Hz, 1H), 2.21-2.13 (m, 1H), 2.11-1.98 (m, 1H), 1.92-1.85 (m, 1H), 1.72-1.58 (m, 1H); $^{13}$C NMR (75 MHz) (rotomers) δ 154.7, 154.6, 147.8, 147.6, 140.5, 140.2, 138.8, 138.6, 137.5, 137.1, 129.1, 128.9, 128.7, 128.6, 128.5, 128.2, 128.1, 128.0, 127.9, 127.6, 127.4, 121.9, 121.7, 67.2, 67.1, 57.0, 56.9, 44.5, 40.7, 39.1, 38.9, 31.2, 30.9; IR (thin film, neat) 3066, 2935, 1698, 1437, 1314, 1259, 1197 cm$^{-1}$; mass spectrum (ESI) m/z 392.1629 [C$_{25}$H$_{23}$NNaO$_2$ (M+Na) requires 392.1626]; LCMS purity 98%.

Benzyl 7-(piperazin-1-yl)-4,5-dihydro-1H-1,5-methanobenzo[c]azepine-2(3H)-carboxylate

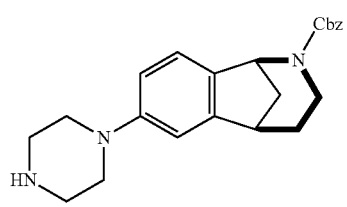

20{1,1}

75%, colorless oil. $^1$H NMR (400 MHz) δ 7.44-7.27 (comp, 5H), 7.21 and 7.09 (rotomers, d, J=7.6 Hz, 1H), 6.83 (d, J=2.4 Hz, 1H), 6.78-6.70 (m, 1H), 5.44-5.42 and 5.34-5.31 (rotomers, m, 1H), 5.22-5.06 (comp, 2H), 3.88-3.73 (m, 1H), 3.22-3.00 (comp, 8H), 2.80-2.68 (m, 1H), 2.52-2.38 (m, 1H), 2.24-2.12 (m, 1H), 2.05-1.90 (m, 1H), 1.84 (d, J=10.4 Hz, 1H), 1.62-1.50 (m, 1H); $^{13}$C NMR (75 MHz) (rotomers) δ 155.1, 152.7, 147.9, 137.4, 137.2, 132.6, 132.3, 128.7, 128.1, 128.0, 124.6, 124.4, 114.7, 111.2, 67.1, 57.4, 57.2, 51.0, 46.5, 44.3, 40.5, 38.8, 30.6; IR (thin film, neat) 2942, 2825, 1692, 1417, 1231, 1101 cm$^{-1}$; mass spectrum (ESI) m/z 378.21766 [C$_{23}$H$_{28}$N$_3$O$_2$ (M+1) requires 378.21815]; LCMS purity 99%.

2-Benzyl-8-(4-(trifluoromethyl)phenyl)-2,3,4,5-tetrahydro-1H-1,5-methanobenzo[c]azepine (21 {2,7})

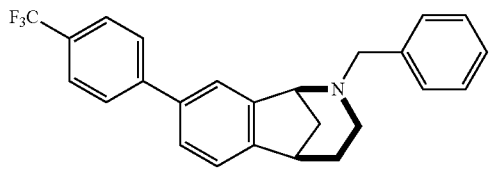

21{2,7}

91%, tan solid: mp 101-103° C.; $^1$H NMR (400 MHz) δ 7.54-7.71 (comp, 4H), 7.50 (d, J=7.6 Hz, 1H), 7.43-7.25 (comp, 7H), 4.00 (d, J=4.8 Hz, 1H), 3.51 (d, J=13.2 Hz, 1H), 3.35 (d, J=13.2 Hz, 1H), 3.23-3.19 (m, 1H), 2.64 (dd, J=10.0, 5.6 Hz, 1H), 2.27-2.20 (m, 1H), 2.11-2.07 (m, 1H), 2.04 (app d, J=11.2 Hz, 1H), 1.62-1.58 (m, 1H), 1.57 (app d, J=9.2 Hz, 1H); $^{13}$C NMR (75 MHz) δ 147.3, 145.4, 138.4, 129.5, 129.2, 128.7, 127.7, 127.4, 127.2, 126.4, 126.1, 126.0, 125.9, 123.3, 122.8, 63.0, 60.4, 47.3, 44.6, 39.8, 29.9; IR (thin film, neat) 2946, 2851, 1321, 1131 cm$^{-1}$; mass spectrum (ESI) m/z 394.17780 [C$_{25}$H$_{23}$F$_3$N (M+1) requires 394.17771]; LCMS purity 96%.

8-(Benzo[d][1,3]dioxol-5-yl)-2,3,4,5-tetrahydro-1H-1,5-methanobenzo[c]azepine (23{2,11})

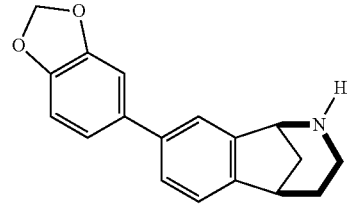

23{2,11}

93%, colorless oil: $^1$H NMR (400 MHz) δ 7.33-7.28 (comp, 2H), 7.14 (d, J=7.8 Hz, 1H), 6.99-6.95 (comp, 2H), 6.78 (d, J=7.8 Hz, 1H), 5.90 (s, 2H), 4.18 (d, J=4.0 Hz, 1H), 3.15-3.09 (m, 1H), 2.65 (dd, J=12.0, 5.6 Hz, 1H), 2.28 (td, J=12.0, 4.7 Hz, 1H), 2.17-2.11 (m, 1H), 2.00 (app s, 1H), 1.95-1.85 (m, 1H), 1.86 (d, J=10.4 Hz, 1H), 1.52-1.44 (m, 1H); IR (thin film, neat) 2951, 1509, 1482, 1228, 1041 cm$^{-1}$; mass spectrum (ESI) m/z 280.1337 [C$_{18}$H$_{18}$NO$_2$ (M+1) requires 280.1332]; LCMS purity 95%.

4-(2-((4-Methoxyphenyl)sulfonyl)-2,3,4,5-tetrahydro-1H-1,5-methanobenzo[c]azepin-8-yl)morpholine (30{2,2,30})

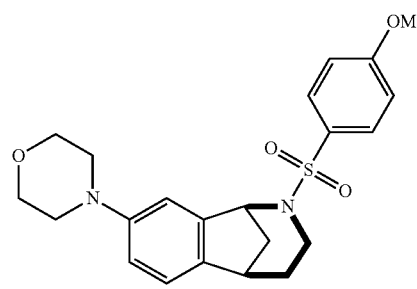

30{2,2,30}

62%, white solid: mp (EtOH) 176-177° C.; $^1$H NMR (400 MHz) δ 7.73 (dd, J=6.8, 2.0 Hz, 2H), 7.03 (d, J=8.0 Hz, 1H), 6.95 (dd, J=6.8, 2.0 Hz, 2H), 6.69 (dd, J=8.0, 2.4 Hz, 1H), 6.07 (d, J=2.4 Hz, 1H), 4.99 (d, J=4.0 Hz, 1H), 3.86 (s, 3H), 3.78 (td, J=4.8, 1.6 Hz, 4H), 3.64 (dd, J=11.9, 6.0 Hz, 1H), 3.15 (br s, 1H), 2.96-2.81 (m, 4H), 2.29 (td, J=11.9, 4.4 Hz, 1H), 2.19-2.11 (m, 1H), 2.10-2.01 (m, 1H), 1.95 (d, J=10.8 Hz, 1H), 1.55 (br d, J=12.4 Hz, 1H); $^{13}$C NMR (75 MHz) δ 162.9, 150.9, 139.6, 138.0, 132.3, 129.7, 123.0, 116.3, 114.4, 112.2, 67.1, 59.9, 55.8, 50.2, 44.7, 40.6, 39.0, 30.6; IR (thin film, neat) 2917, 1593, 1494, 1326, 1253, 1156 cm$^{-1}$; mass spectrum (ESI) m/z 415.1687 [C$_{22}$H$_{27}$N$_2$O$_4$S (M+1) requires 415.1692]; LCMS purity 100%.

8-(Benzo[d][1,3]dioxol-5-yl)-2-(naphthalen-1-ylsulfonyl)-2,3,4,5-tetrahydro-1H-1,5-methanobenzo[c]azepine (30{2,11,24})

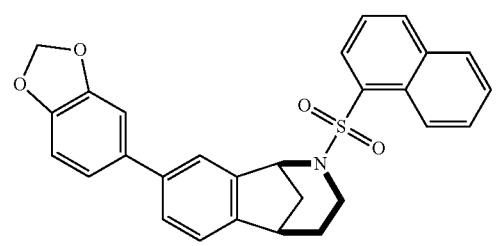

30{2,11,24}

59%, white foam. $^1$H NMR (400 MHz) δ 8.72 (d, J=8.6 Hz, 1H), 8.29 (dd, J=7.5, 1.4 Hz, 1H), 8.02 (d, J=8.6 Hz, 1H), 7.87 (d, J=7.5 Hz, 1H), 7.64-7.59 (m, 1H), 7.57-7.52 (comp, 2H), 7.27 (d, J=8.4 Hz, 1H), 7.14 (d, J=7.6 Hz, 1H), 6.82 (d, J=8.4 Hz, 1H), 6.71 (dd, J=8.4, 1.7 Hz, 1H), 6.66 (d, J=1.7 Hz, 1H), 6.62-6.61 (m, 1H), 6.02 (s, 2H), 5.19 (d, J=4.0 Hz, 1H), 3.65 (dd, J=12.0, 6.0 Hz, 1H), 3.26-3.22 (m, 1H), 2.45 (td, J=12.0, 4.8 Hz, 1H), 2.23-2.16 (m, 1H), 2.08-1.99 (m, 1H), 1.97 (d, J=11.2 Hz, 1H), 1.63-1.56 (m, 1H); $^{13}$C NMR (125 MHz) δ 147.9, 146.9, 144.7, 140.2, 139.5, 135.2, 135.1, 134.4, 134.2, 130.1, 128.9, 128.8, 128.0, 127.2, 126.8, 125.2, 124.3, 122.6, 122.5, 120.5, 108.3, 107.7, 101.1, 58.9, 44.2, 40.2, 39.3, 30.3; IR (thin film, neat) 2969, 2873, 1479, 1341, 1224, 1163 cm$^{-1}$; mass spectrum (ESI) m/z 470.14196 [$C_{28}H_{24}NO_4S$ (M+1) requires 470.14206]; LCMS purity 100%.

8-(4-Fluorophenyl)-2,3,4,5-tetrahydro-1H-1,5-methanobenzo[c]azepine-2-carbonyl)benzonitrile (28{2,10,15})

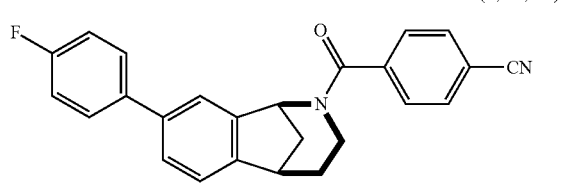

28{2, 10, 15}

82%, pale green gum. $^1$H NMR (400 MHz) δ 7.80 (d, J=8.2 Hz, 1H), 7.66 (d, J=8.2 Hz, 1H) 7.65-7.47 (comp, 5H), 7.46 (d, J=7.6 Hz, 1H), 7.32 (d, J=7.6 Hz, 1H), 7.20-7.09 (comp, 2H), 6.01 and 4.86 (rotomers, d, J=4.2 Hz, 1H), 4.32 and 3.28 (rotomers, dd, J=13.6, 6.4 Hz, 1H), 3.45-3.39 (m, 1H), 2.76 and 2.48 (rotomers, td, J=12.8, 5.2 Hz, 1H), 2.42-2.35 and 2.27-2.20 (rotomers, m, 1H), 2.19-2.10 and 1.98-1.90 (rotomers, m, 1H), 2.00 (d, J=11.6 Hz, 1H), 1.85-1.77 and 1.62-1.54 (rotomers, m, 1H); $^{13}$C NMR (75 MHz) (rotomers) δ 167.9, 163.3 (d, JC-F=245 Hz), 146.0, 145.4, 144.4, 141.2, 140.8, 140.6, 140.2, 137.2, 133.0, 132.6, 128.9, 128.8, 128.4, 128.1, 127.9, 123.6, 123.4, 123.0, 122.2, 118.4, 116.0 (d, JC-F=21.3 Hz), 113.6, 61.4, 55.9, 44.4, 43.0, 40.0, 37.5, 31.5, 30.3; IR (thin film, neat) 2949, 1637, 1437, 1231 cm$^{-1}$; mass spectrum (ESI) m/z 383.15611 [$C_{25}H_{20}FN_{20}$ (M+1) requires 383.15542]; LCMS purity 100%.

Benzyl 8-(4-pivaloylpiperazin-1-yl)-4,5-dihydro-1H-1,5-methanobenzo[c]azepine-2(3H)-carboxylate (38{2,1,9})

38{2,1,9}

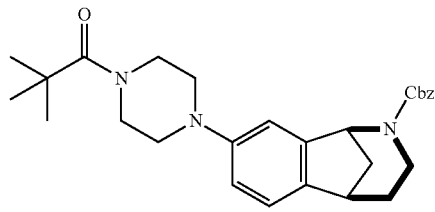

96%, tan semi-solid: $^1$H NMR (400 MHz) δ 7.44-7.26 (m, 5H), 7.12 (d, J=8.0 Hz, 1H), 6.80 (dd, J=8.2, 2.2 Hz, 1H) 6.96 and 6.75 (rotomers, br s, 1H), 5.45 and 5.34 (rotomers, br s, 1H), 5.26-5.07 (comp, 2H), 3.80 (m, 1H), 3.79 (t, J=4.8 Hz, 4H), 3.23-3.19 (m, 1H), 3.15-3.06 (m, 4H), 2.50-2.36 (m, 1H), 2.24-2.12 (m, 1H), 2.02-1.90 (m, 1H), 1.85 (d, J=10.8 Hz, 1H), 1.62-1.50 (m, 1H), 1.31 (s, 9H); $^{13}$C NMR (75 MHz) δ (rotomers) 176.6, 155.3, 155.2, 151.0, 142.6, 142.5, 138.6, 137.4, 137.3, 128.7, 128.2, 123.4, 116.8, 116.6, 112.9, 67.2, 58.1, 57.9, 54.0, 50.4, 45.3, 44.0, 39.2, 38.9, 30.7, 28.7; IR (thin film, neat) 2941, 2880, 2818, 1698, 1630, 1417, 1238, 1183 cm$^{-1}$; (ESI) m/z 462.2753 [$C_{28}H_{36}N_3O_3$ (M+1) requires 462.2751]; LCMS purity 100%.

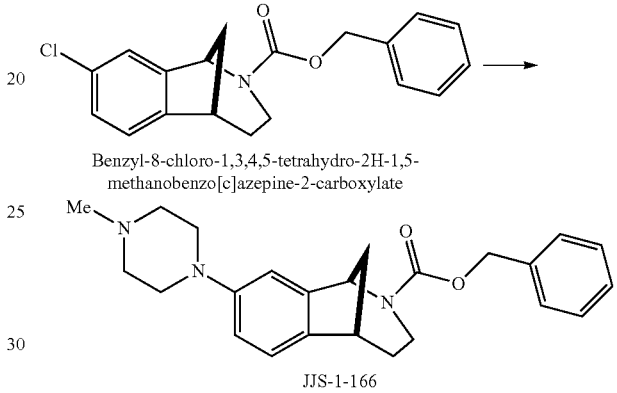

Benzyl-8-chloro-1,3,4,5-tetrahydro-2H-1,5-methanobenzo[c]azepine-2-carboxylate

JJS-1-166

A solution of benzyl-8-chloro-1,3,4,5-tetrahydro-2H-1,5-methanobenzo[c]azepine-2-carboxylate (85.0 mg, 0.259 mmol), sodium tert-butoxide (33 mg, 0.337 mmol) and 1-methylpiperazine (35 μL, 0.311 mmol) in degassed toluene (1.2 mL) was stirred for 5 min at room temp. 325 μL of a freshly prepared stock solution of Pd(OAc)$_2$ and 2-(di-tert-butylphosphino)biphenyl (1:1) in toluene (1.0 mL, 0.04 mM), that had been stirred for 20 min, was added to the reaction mixture via syringe. After heating at 100° C. for 3 h, the reaction was cooled to room temp, poured into water (3 mL) and extracted with CH$_2$Cl$_2$ (3×10 mL). The combined organic extracts were dried (K$_2$CO$_3$), filtered and concentrated under reduced pressure to provide the crude product, which was purified via radial plc (SiO$_2$), eluting with hexanes/EtOAc/triethylamine (100:0:0→80:20:0→50:48:1→23:75:2) to give 56 mg (55%) of JJS-1-166 as a light orange, viscous oil: $^1$H NMR (500 MHz, DMSO d$_6$, as a mixture of rotomers) δ 7.46-7.26 (comp, 5H), 7.10 (d, J=8.5 Hz, 1H), 6.82 (br s, 0.4H), 6.80 (d, J=8.5 Hz, 1H), 6.71 (br s, 0.6H), 5.25 (br s, 1H), 5.17 (br d, J=13.5 Hz, 0.4H), 5.07 (br d, J=13.5 Hz, 0.6H), 3.70-3.59 (m, 1H), 3.17-3.13 (m, 1H), 3.10-2.98 (m, 1H), 2.41 (t, J=5.0 Hz, 4H), 2.33-2.26 (m, 1H), 2.20 (s, 3H), 2.10-2.02 (m, 1H), 1.92-1.83 (m, 1H), 1.74 (d, J=10.5 Hz, 1H), 1.54-1.42 (m, 1H); liquid chromatography (reverse phase, CH$_3$CN/H$_2$O with 0.1% formic acid) retention time 3.0 min; mass spectrum m/z (ESI) 392.2 (M+1).

Biological Activity

Activity of certain compounds of the present disclosure were tested and the results are shown in Table 6. These tests have unveiled some interesting biological activities that have not been previously associated with the norbenzomorphan class of compounds.

TABLE 6

Biological Activity of Select Norbenzomorphans

| Entry | Compound | Activity* | Potency |
|---|---|---|---|
| 1 | <br>28{2, 3, 19} | human $M_1$ muscarinic receptor antagonist[18] | 69% (3 μM) |
| 2 | <br>28{2, 6, 15} | striatal-enriched protein tyrosine phosphatase (STEP) inhibitor[16] | 69% (20 μM) |
| 3 | <br>40{1, 1, 32} | fatty acid synthase inhibitor[17] | 57% (15 μM) |
| 4 | <br>18{3} | Y. pestis topoisomerase I inhibitor[19] | 61% (10 μM) |
| 5 | <br>23{2, 8} | mycobacterium tuberculosis bioA enzyme inhibitor[20] | 91% (10 μM) |
| 6 | <br>20{2, 4} | microphthalmia-associated transcription factor (MITF) activator[21] | 3.3 μM ($AC_{40}$) |

TABLE 6-continued

Biological Activity of Select Norbenzomorphans

| Entry | Compound | Activity* | Potency |
|---|---|---|---|
| 7 | 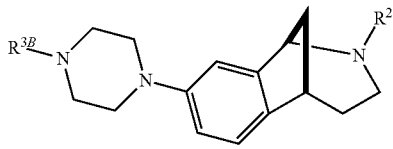 20{2, 3, 4} | serotonin 5A receptor (5HTR5A) inverse agonist[22] | 27% (9.3 µM) |

It is noteworthy that inhibitors of both striatal-enriched protein tyrosine phosphatase (STEP)[16] and fatty acid synthase (FAS)[17] are being investigated as potential therapeutics for the treatment of Alzheimer's Disease (AD) and cancer, respectively (Table 6). STEP is a brain specific tyrosine phosphatase that is elevated in AD patients. Recent work suggests that decreasing STEP levels in the prefrontal cortex can mitigate the cognitive deficits from AD. Furthermore, FAS is overexpressed in many cancers and is believed to be essential for the growth of solid tumors. It has been demonstrated that inhibition of FAS can induce apoptosis in cancer cells. Accordingly, compounds that exhibit selective inhibition of these targets could lead to advances in the development of drugs relevant to these diseases.

IX. References

1. Hardy J, Selkoe D J. The amyloid hypothesis of Alzheimer's disease: progress and problems on the road to therapeutics. Science 2002; 297:353-356.
2. Backman L, Jones S, Berger A K, Laukka E J, Small B J. Multiple cognitive deficits during the transition to Alzheimer's diseases. J Intern Med. 2004; 256(3): 195-204.
3. Faizi M, Bader P L, Saw N, Nguyen T V, Beraki S, Wyss-Coray T, Longo F, Shamloo M. Thy1-hAPPLond/Swe+ mouse model of Alzheimer's disease displays broad behavioral deficits in sensorimotor, cognitive and social function. Brain Behav. 2012. 2(2): 142-154.
4. Rockenstein E, Mallory M, Mante M, Sisk A, Masliaha E. Early formation of mature amyloid-beta protein deposits in a mutant APP transgenic model depends on levels of Abeta(1-42). J. Neurosci. Res. 2001. 66(4): 573-582.

What is claimed is:
1. A compound having the formula:

$R^{3B}$—N\_\_N—[structure]—N—$R^2$ wherein:
$R^2$ is halogen, —$N_3$, —$CF_3$, —$CCl_3$, —$CBr_3$, —$CI_3$, —CN, —C(O)$R^4$, —O$R^4$, —N$R^4R^{4A}$, —C(O)O$R^4$, —C(O)N$R^4R^{4A}$, —$NO_2$, —S$R^4$, —S(O)$_{n2}R^4$, —S(O)$_{n2}$O$R^4$, —S(O)$_{n2}$N$R^4R^{4A}$, —NHN$R^4R^{4A}$, —ON$R^4R^{4A}$, —NHC(O)NHN$R^4R^{4A}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
n2 is 1 or 2;
$R^4$, $R^{4A}$ are independently hydrogen, oxo, halogen, —$CF_3$, —CN, —OH, —$NH_2$, —COOH, —CONH$_2$, —$NO_2$, —SH, —S(O)$_2$Cl, —S(O)$_3$H, —S(O)$_4$H, —S(O)$_2$NH$_2$, —NHNH$_2$, —ONH$_2$, —NHC(O)NHNH$_2$, —NHC(O)NH$_2$, —NHS(O)$_2$H, —NHC(O)H, —NHC(O)—OH, —NHOH, —OCF$_3$, —OCHF$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^{3B}$ is —$CF_3$, —CN, —OH, —$NH_2$, —CONH$_2$, —S(O)$_3$H, —S(O)$_2$NH$_2$, —NHC(O)NH$_2$, —NHC(O)H, —OCHF$_2$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;
with the proviso that the compound is not

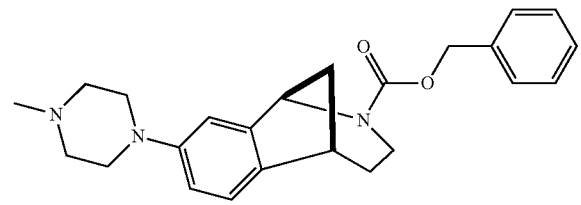

2. The compound of claim 1, wherein
$R^2$ is halogen, —CN, —C(O)$R^4$, —O$R^4$, —N$R^4R^{4A}$, —C(O)O$R^4$, —C(O)N$R^4R^{4A}$, —S(O)$_{n2}R^4$, —S(O)$_{n2}$O$R^4$, —S(O)$_{n2}$N$R^4R^{4A}$, —ON$R^4R^{4A}$, —NHC(O)NHN$R^4R^{4A}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.
3. The compound of claim 1, wherein $R^2$ is —O$R^4$, —N$R^4R^{4A}$, —C(O)O$R^4$, substituted or unsubstituted alkyl, substituted or unsubstituted cycloalkyl, substituted or unsubstituted heterocycloalkyl, substituted or unsubstituted aryl, substituted or unsubstituted heteroaryl.
4. The compound of claim 1, wherein $R^2$ is —O$R^4$, —N$R^4R^{4A}$, —C(O)O$R^4$, substituted or unsubstituted alkyl, substituted or unsubstituted heterocycloalkyl, substituted or unsubstituted aryl, substituted or unsubstituted heteroaryl.

5. The compound of claim 1, wherein $R^2$ is —C(O)OR$^4$, wherein $R^4$ is $R^{4B}$-substituted or unsubstituted aryl, wherein $R^{4B}$ is —CF$_3$, —CN, —OH, unsubstituted alkyl or unsubstituted heteroalkyl.

6. The compound of claim 5, wherein $R^4$ is unsubstituted aryl.

7. The compound of claim 1, wherein $R^2$ is $R^{4B}$-substituted or unsubstituted alkyl, wherein $R^{4B}$ is $R^{4C}$-substituted or unsubstituted aryl, wherein $R^{4C}$ is halogen, —CF$_3$, —CN, —OH, unsubstituted alkyl or unsubstituted heteroalkyl.

8. The compound of claim 7, wherein $R^{4C}$ is unsubstituted aryl.

9. The compound of claim 1, wherein $R^2$ is unsubstituted $C_1$-$C_5$ alkyl.

10. The compound of claim 1, wherein $R^{3B}$ is substituted or unsubstituted alkyl.

11. The compound of claim 1, wherein $R^2$ is —C(O)OR$^4$ or —C(O)R$^4$, wherein $R^4$ is substituted or unsubstituted aryl or heteroaryl, wherein the substituted aryl is substituted with halogen, —CF$_3$, —CN, —OH, unsubstituted alkyl or unsubstituted heteroalkyl.

12. The compound of claim 11, wherein $R^4$ is unsubstituted or substituted phenyl.

13. A pharmaceutical composition comprising a compound of claim 1 and a pharmaceutically acceptable excipient or pharmaceutically acceptable salt.

14. A method of treating a neurodegenerative disease in a subject in need thereof, the method comprising administering an effective amount of the compound of claim 1, wherein the neurodegenerative disease is Alzheimer's disease or Amyotrophic lateral sclerosis.

* * * * *